US010246505B2

(12) United States Patent
Berger et al.

(10) Patent No.: US 10,246,505 B2
(45) Date of Patent: Apr. 2, 2019

(54) CHIMERIC ANTIGEN RECEPTORS TO CONTROL HIV INFECTION

(71) Applicant: The United States of America, as represented by the Secretary, Department of Health and Human Services, Washington, DC (US)

(72) Inventors: Edward A. Berger, Rockville, MD (US); Mustafa H. Ghanem, Brooklyn, NY (US); Barna Dey, Germantown, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/039,384

(22) PCT Filed: Nov. 25, 2014

(86) PCT No.: PCT/US2014/067459
§ 371 (c)(1),
(2) Date: May 25, 2016

(87) PCT Pub. No.: WO2015/077789
PCT Pub. Date: May 28, 2015

(65) Prior Publication Data
US 2017/0267739 A1    Sep. 21, 2017

Related U.S. Application Data

(60) Provisional application No. 61/908,691, filed on Nov. 25, 2013, provisional application No. 62/040,398, filed on Aug. 21, 2014.

(51) Int. Cl.
C07K 14/73      (2006.01)
A61K 48/00      (2006.01)
C07K 14/725     (2006.01)
C07K 14/705     (2006.01)
C07K 16/10      (2006.01)

(52) U.S. Cl.
CPC ...... *C07K 14/70514* (2013.01); *A61K 48/005* (2013.01); *C07K 14/7051* (2013.01); *C07K 14/70521* (2013.01); *C07K 14/70564* (2013.01); *C07K 16/1063* (2013.01); *C07K 2317/622* (2013.01); *C07K 2319/02* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| 5,013,548 A | 5/1991 | Haynes et al. |
| 5,529,774 A | 6/1996 | Barba et al. |
| 5,587,455 A | 12/1996 | Berger et al. |
| 5,637,481 A | 6/1997 | Ledbetter et al. |
| 5,643,756 A | 7/1997 | Kayman et al. |
| 5,695,927 A | 12/1997 | Masuho et al. |
| 5,696,237 A | 12/1997 | Fitzgerald et al. |
| 5,712,149 A | 1/1998 | Roberts |
| 5,767,260 A | 6/1998 | Whitlow et al. |
| 5,843,454 A | 12/1998 | Devico et al. |
| 5,856,456 A | 1/1999 | Whitlow et al. |
| 6,027,890 A | 2/2000 | Ness et al. |
| 6,103,521 A | 8/2000 | Capon et al. |
| 6,117,655 A | 9/2000 | Capon et al. |
| 6,329,202 B1 | 12/2001 | Gershoni |
| 7,115,262 B1 | 10/2006 | Berger et al. |
| 8,420,099 B2 | 4/2013 | Berger et al. |
| 2012/0213783 A1 | 8/2012 | Rosenberg et al. |
| 2012/0321667 A1 | 12/2012 | Sentman |

FOREIGN PATENT DOCUMENTS

| WO | WO 1998/036087 | 8/1998 |
| WO | WO 2012/079000 | 6/2012 |
| WO | WO 2013/059593 | 4/2013 |
| WO | WO 2013/126726 | 8/2013 |
| WO | WO 2014/039523 | 3/2014 |

OTHER PUBLICATIONS

Sahu et al. "Anti-HIV designer T cells progressively eradicate a latently infected cell line by sequentially inducing HIV reactivation then killing the newly gp120-positive cells.", Virology Sep. 2013 (online), vol. 446, No. 1-2, pp. 268-275, XP002736705.*
Grada et al. "TanCAR: A Novel Bispecific Chimeric Antigen Receptor for Cancer Immunotherapy.", Molecular Therapy 2013, vol. 2, Jul. 2013 (online), p. e105, XP002736704.*
Du et al. "Bifunctional CD4-DC-SIGN fusion proteins demonstrate enhanced avidity to gp1 20 and inhibit HIV-1 infection and dissemination.", Antimicrobial Agents and Chemotherapy 2012, vol. 56, pp. 4640-4649, XP002736780.*
Lam et al. "T-cell therapies for HIV.",Immunotherapy Apr. 2013, vol. 5,, pp. 407-414, XP002736706.*

(Continued)

*Primary Examiner* — Maury A Audet
(74) *Attorney, Agent, or Firm* — Klarquist Sparkman, LLP

(57) ABSTRACT

The present disclosure is directed to novel multispecific chimeric antigen receptor (CAR) proteins and DNA sequences encoding these proteins. The CARs comprise at least two extracellular domains fused, via a transmembrane domain to a cytoplasmic signaling domain comprising two signaling domains. The disclosure further relates to nucleic acids encoding the novel CARs, to host cells expressing the novel CARs, and to methods of using the CARs to co-stimulate effector functions in the cells and for using cells expressing the receptors for treatment of disease and viral infections. The disclosure also relates to methods of generating a recombinant T cell with reduced susceptibility to HIV infection.

17 Claims, 15 Drawing Sheets

Specification includes a Sequence Listing.

(56) References Cited

OTHER PUBLICATIONS

Almeida et al. "Antigen sensitivity is a major determinant of CD8+ T-cell polyfunctionality and HIV-suppressive activity." *Blood* 113, No. 25 (2009): 6351-6360.
Anderluh, et al. *DC-SIGN Antagonists—A Paradigm of C-Type Lectin Binding Inhibition*. INTECH Open Access Publisher, 2012.
Berger. "Targeted cytotoxic therapy: adapting a rapidly progressing anti-cancer paradigm for depletion of persistent HIV-infected cell reservoirs," *Current Opinion in HIV and AIDS* 6, No. 1 (2011): 80.
Bitton et al. "Characterization of T cell-expressed chimeric receptors with antibody-type specificity for the CD4 binding site of HIV-1 gp120." *European Journal of Immunology* 28, No. 12 (1998): 4177-4187.
Brentjens et al. "Treatment of chronic lymphocytic leukemia with genetically targeted autologous T cells: case report of an unforeseen adverse event in a phase I clinical trial." *Molecular Therapy* 18, No. 4 (2010): 666-668.
Carter et al. "Humanization of an anti-p185HER2 antibody for human cancer therapy." *Proceedings of the National Academy of Sciences* 89, No. 10 (1992): 4285-4289.
de Fougerolles et al. "Intercellular adhesion molecule 3, a third adhesion counter-receptor for lymphocyte function-associated molecule 1 on resting lymphocytes." *The Journal of Experimental Medicine* 175, No. 1 (1992): 185-190.
Deeks et al. "A phase II randomized study of HIV-specific T-cell gene therapy in subjects with undetectable plasma viremia on combination antiretroviral therapy." *Molecular Therapy* 5, No. 6 (2002): 788-797.
Dey et al. "Neutralization of human immunodeficiency virus type 1 by sCD4-17b, a single-chain chimeric protein, based on sequential interaction of gp120 with CD4 and coreceptor." *Journal of Virology* 77, No. 5 (2003): 2859-2865.
Drickamer. "Engineering galactose-binding activity into a C-type mannose-binding protein." *Nature* (1992): 183-186.
Du et al. "Bifunctional CD4—DC-SIGN fusion proteins demonstrate enhanced avidity to gp120 and inhibit HIV-1 infection and dissemination." *Antimicrobial Agents and Chemotherapy* 56, No. 9 (2012): 4640-4649.
Feinberg et al. "Multiple modes of binding enhance the affinity of DC-SIGN for high mannose N-linked glycans found on viral glycoproteins." *Journal of Biological Chemistry* 282, No. 6 (2007): 4202-4209.
Feinberg et al. "Structural basis for selective recognition of oligosaccharides by Dc-Sign and Dc-Signr." *Science* 294, No. 5549 (2001): 2163-2166.
Gershoni et al. "HIV binding to its receptor creates specific epitopes for the CD4/gp120 complex." *The Faseb Journal* 7, No. 12 (1993): 1185-1187.
Grada et al. "TanCAR: a novel bispecific chimeric antigen receptor for cancer immunotherapy," *Molecular Therapy Nucleic Acids* 2, No. 7 (2013): e105.
Grupp et al. "Chimeric antigen receptor—modified T cells for acute lymphoid leukemia." *New England Journal of Medicine* 368, No. 16 (2013): 1509-1518.
Han et al. "Chimeric antigen receptor-engineered T cells for cancer immunotherapy: progress and challenges." *J Hematol Oncol* 6, No. 1 (2013): 47.
Haso et al. "Anti-CD22—chimeric antigen receptors targeting B-cell precursor acute lymphoblastic leukemia." *Blood* 121, No. 7 (2013): 1165-1174.
Hennecke et al. "Non-repetitive single-chain Fv linkers selected by selectively infective phage (SIP) technology." *Protein Engineering* 11, No. 5 (1998): 405-410.
Herschhorn et al. "An inducible cell-cell fusion system with integrated ability to measure the efficiency and specificity of HIV-1 entry inhibitors." *PloS one* 6, No. 11 (2011): e26731.
Jameson et al. "Expression of DC-SIGN by dendritic cells of intestinal and genital mucosae in humans and rhesus macaques," *Journal of Virology* 76, No. 4 (2002): 1866-1875.

Jones et al. "Lentiviral vector design for optimal T cell receptor gene expression in the transduction of peripheral blood lymphocytes and tumor-infiltrating lymphocytes." *Human Gene Therapy* 20, No. 6 (2009): 630-640.
Kumaresan et al. "Bioengineering T cells to target carbohydrate to treat opportunistic fungal infection." *Proceedings of the National Academy of Sciences USA* 111, No. 29 (2014): 10660-10665.
Kwong et al. "Structure of an HIV gp120 envelope glycoprotein in complex with the CD4 receptor and a neutralizing human antibody." *Nature* 393, No. 6686 (1998): 648-659.
Kwong et al. "Probability analysis of variational crystallization and its application to gp120, the exterior envelope glycoprotein of type I human immunodeficiency virus (HIV-1)." *Journal of Biological Chemistry* 274, No. 7 (1999): 4115-4123.
Lagenaur et al. "sCD4-17b bifunctional protein: extremely broad and potent neutralization of HIV-1 Env pseudotyped viruses from genetically diverse primary isolates." *Retrovirology* 7, No. 1 (2010): 1.
Lam et al. "T-cell: therapies for HIV." *Immunotherapy* 5, No. 4 (2013): 407-414.
Lamers, et al. "Immune responses to transgene and retroviral vector in patients treated with ex vivo—engineered T cells." *Blood* 117, No. 1 (2011): 72-82.
Mitsuyasu et al. "Prolonged survival and tissue trafficking following adoptive transfer of CD4ζ, gene-modified autologous CD4+ and CD8+ T cells in human immunodeficiency virus—infected subjects." *Blood* 96, No. 3 (2000): 785-793.
Mondor et al. "Human immunodeficiency virus type 1 attachment to HeLa CD4 cells is CD4 independent and gp120 dependent and requires cell surface heparans." *Journal of Virology* 72, No. 5 (1998): 3623-3634.
Morgan et al. "Case report of a serious adverse event following the administration of T cells transduced with a chimeric antigen receptor recognizing ERBB2." *Molecular Therapy* 18, No. 4 (2010): 843-851.
Mothe et al. "CTL responses of high functional avidity and broad, variant cross-reactivity are associated with HIV control." *PloS One* 7, No. 1 (2012): e29717.
Moulard et al. "Broadly cross-reactive HIV-1-neutralizing human monoclonal Fab selected for binding to gp120-CD4-CCR5 complexes." *Proceedings of the National Academy of Sciences* 99, No. 10 (2002): 6913-6918.
Nora et al. "Functional diversity of HIV-1 envelope proteins expressed by contemporaneous plasma viruses." *Retrovirology* 5, No. 1 (2008): 23.
Nussbaum et al. "Fusogenic mechanisms of enveloped-virus glycoproteins analyzed by a novel recombinant vaccinia virus-based assay quantitating cell fusion-dependent reporter gene activation." *Journal of Virology* 68, No. 9 (1994): 5411-5422.
Park et al. "Treating cancer with genetically engineered T cells," *Trends in Biotechnology* 29, No. 11 (2011):550-557.
Reeves et al. "Enfuvirtide resistance mutations: impact on human immunodeficiency virus envelope function, entry inhibitor sensitivity, and virus neutralization." *Journal of Virology* 79, No. 8 (2005): 4991-4999.
Reiter et al. "Engineering interchain disulfide bonds into conserved framework regions of Fv fragments: improved biochemical characteristics of recombinant immunotoxins containing disulfide-stabilized Fv." *Protein Engineering* 7, No. 5 (1994): 697-704.
Sakihama et al. "Oligomerization of CD4 is required for stable binding to class II major histocompatibility complex proteins but not for interaction with human immunodeficiency virus gp120." *Proceedings of the National Academy of Sciences* 92, No. 14 (1995): 6444-6448.
Sahu et al. "Anti-HIV designer T cells progressively eradicate a latently infected cell line by sequentially inducing HIV reactivation then killing the newly gp120-positive cells." *Virology* 446, No. 1 (2013): 268-275.
Salzwedel et al. "Sequential CD4-coreceptor interactions in human immunodeficiency virus type 1 Env function: soluble CD4 activates Env for coreceptor-dependent fusion and reveals blocking activities of antibodies against cryptic conserved epitopes on gp120." *Journal of Virology* 74, No. 1 (2000): 326-333.

(56) References Cited

OTHER PUBLICATIONS

Sattentau. "The direct passage of animal viruses between cells." *Current Opinion in Virology* 1, No. 5, (2011): 396-402.

Scholler et al. "Decade-long safety and function of retroviral-modified chimeric antigen receptor T cells." *Science Translational Medicine* 4, No. 132 (2012): 132ra53-132ra53.

Sheriff et al. "Human mannose-binding protein carbohydrate recognition domain trimerizes through a triple α-helical coiled-coil." *Nature Structural & Molecular Biology* 1, No. 11 (1994): 789-794.

Snyder et al. "Molecular mechanisms and biological significance of CTL avidity." *Current HIV Research* 1, No. 3 (2003): 287-294.

Thali et al. "Characterization of conserved human immunodeficiency virus type 1 gp120 neutralization epitopes exposed upon gp120-CD4 binding." *Journal of Virology* 67, No. 7 (1993): 3978-3988.

Till et al. "Adoptive immunotherapy for indolent non-Hodgkin lymphoma and mantle cell lymphoma using genetically modified autologous CD20-specific T cells." *Blood* 112, No. 6 (2008): 2261-2271.

Trkola et al. "Cross-clade neutralization of primary isolates of human immunodeficiency virus type 1 by human monoclonal antibodies and tetrameric CD4-IgG." *Journal of Virology* 69, No. 11 (1995): 6609-6617.

Tumaini et al. "Simplified process for the production of anti—CD19-CAR—engineered T cells." *Cytotherapy* 15, No. 11 (2013): 1406-1415.

Walker et al. "Broad and potent neutralizing antibodies from an African donor reveal a new HIV-1 vaccine target." *Science* 326, No. 5950 (2009): 285-289.

Walker et al. "Broad neutralization coverage of HIV by multiple highly potent antibodies." *Nature* 477, No. 7365 (2011): 466-470.

Walker et al. "Long-term in vivo survival of receptor-modified syngeneic T cells in patients with human immunodeficiency virus infection." *Blood* 96, No. 2 (2000): 467-474.

Watkins et al. "An anti-HIV-1 V3 loop antibody fully protects cross-clade and elicits T-cell immunity in macaques mucosally challenged with an R5 clade C SHIV." *PloS One* 6, No. 3 (2011): e18207.

Xiang et al. "Functional mimicry of a human immunodeficiency virus type 1 coreceptor by a neutralizing monoclonal antibody." *Journal of Virology* 79, No. 10 (2005): 6068-6077.

Zhao et al. "A herceptin-based chimeric antigen receptor with modified signaling domains leads to enhanced survival of transduced T lymphocytes and antitumor activity." *The Journal of Immunology* 183, No. 9 (2009): 5563-5574.

\* cited by examiner

```
                        SEQUENCE LISTING

<160> NUMBER OF SEQ ID NOS: 59

<210> SEQ ID NO 1
<211> LENGTH: 5
<212> TYPE: PRT
<213> ORGANISM: artificial sequence
<220> FEATURE:
<223> OTHER INFORMATION: Synthetic construct

<400> SEQUENCE: 1

Gly Gly Gly Gly Ser
1               5

<210> SEQ ID NO 2
<211> LENGTH: 35
<212> TYPE: PRT
<213> ORGANISM: artificial sequence
<220> FEATURE:
<223> OTHER INFORMATION: Synthetic construct

<400> SEQUENCE: 2

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 3
<211> LENGTH: 10
<212> TYPE: PRT
<213> ORGANISM: artificial sequence
<220> FEATURE:
<223> OTHER INFORMATION: Synthetic construct

<400> SEQUENCE: 3

Gly Gly Gly Gly Ser Gly Gly Gly Gly Ser
1               5                   10

<210> SEQ ID NO 4
<211> LENGTH: 2154
<212> TYPE: DNA
```

<213> ORGANISM: artificial sequence
<220> FEATURE:
<223> OTHER INFORMATION: Synthetic construct

<400> SEQUENCE: 4

| | | | | | |
|---|---|---|---|---|---|
| atggttcgag | gcgtgccctt | ccggcatctg | ctgctggtgc | tgcagctggc | tctcctgcct | 60 |
| gccgccaccc | agggcaagaa | agtggtgctg | ggcaaaaagg | gcgacaccgt | ggaactgacc | 120 |
| tgcaccgcca | gccagaagaa | gtccatccag | ttccactgga | gaacagcaa | ccagatcaag | 180 |
| atcctgggca | accagggcag | cttcctgacc | aagggcccca | gcaagctgaa | cgaccgggcc | 240 |
| gatagccggc | ggagcctgtg | ggaccagggc | aatttcccac | tgatcatcaa | gaacctgaag | 300 |
| atcgaggaca | gcgacaccta | catctgcgag | gtcgaagatc | agaaagaaga | ggtgcagctg | 360 |
| ctggtgttcg | gcctgaccgc | caactccgac | acccatctgc | tgcagggcca | gagcctgacc | 420 |
| ctcaccctgg | aaagcccccc | tggcagcagc | cccagcgtgc | agtgcagaag | ccccagaggc | 480 |
| aagaacatcc | agggcggcaa | gaccctgagc | gtgtcccagc | tggaactgca | ggactccggc | 540 |
| acctggacct | gtaccgtgct | gcagaaccag | aaaaaggtcg | agttcaagat | cgacatcgtg | 600 |
| gtgctggcct | tccagaaggc | ctctggcggc | ggaggatctg | gcggaggtgg | aagtggcggg | 660 |
| ggaggtagtg | gcggaggcgg | atcaggtggc | ggaggttcag | gcggtggcgg | aagcggaggc | 720 |
| ggtggatctc | aggtccagct | gctcgaatct | ggcgccgaag | tgaagaaacc | cggcagcagc | 780 |
| gtgaaagtgt | cctgcaaggc | cagcggcgac | accttcatcc | ggtacagctt | cacatgggtc | 840 |
| cgacaggccc | ctgggcaggg | cctggaatgg | atgggccgga | tcatcaccat | cctggacgtg | 900 |
| gcccactacg | ccccacatct | gcagggcaga | gtgaccatca | ccgccgacaa | gagcaccagc | 960 |
| accgtgtacc | tggaactgcg | gaacctgcgg | agcgacgata | ccgccgtcta | cttctgtgcc | 1020 |
| ggcgtgtacg | agggcgaggc | cgatgagggc | gagtacgaca | caacggcttc | ctgaagcac | 1080 |
| tggggccagg | gcaccctcgt | caccgtgacc | agcggcggcg | gaggatctgg | cggaggtgga | 1140 |
| agtggcgggg | gaggtagtga | gctggaactc | acccagagcc | ccgccaccct | gtccgtgtct | 1200 |
| ccaggcgaga | gagccaccct | gagctgcaga | gccagcgaga | gcgtgtccag | cgacctggcc | 1260 |
| tggtatcagc | agaagcccgg | ccaggccccc | agactgctga | tctacggcgc | cagcaccaga | 1320 |
| gccacaggcg | tgccagccag | attcagcggc | agcggtagcg | gagccgagtt | caccctgacc | 1380 |
| atcagcagcc | tgcagagcga | ggactttgcc | gtgtactact | gccagcagta | caacaactgg | 1440 |
| ccccccagat | acaccttcgg | ccagggaacc | cggctggaaa | tcaaggcggc | cgcaattgaa | 1500 |
| gttatgtatc | ctcctcctta | cctagacaat | gagaagagca | atggaaccat | tatccatgtg | 1560 |
| aaagggaaac | acctttgtcc | aagtcccta | tttcccggac | cttctaagcc | cttttgggtg | 1620 |
| ctggtggtgg | ttggtggagt | cctggcttgc | tatagcttgc | tagtaacagt | ggcctttatt | 1680 |
| attttctggg | tgaggagtaa | gaggagcagg | ctcctgcaca | gtgactacat | gaacatgact | 1740 |
| ccccgccgcc | ccgggcccac | ccgcaagcat | taccagccct | atgccccacc | acgcgacttc | 1800 |
| gcagcctatc | gctccagagt | gaagttcagc | aggagcgcag | acgcccccgc | gtaccagcag | 1860 |
| ggccagaacc | agctctataa | cgagctcaat | ctaggacgaa | gagaggagta | cgatgttttg | 1920 |
| gacaagagac | gtggccggga | ccctgagatg | gggggaaagc | cgagaaggaa | gaaccctcag | 1980 |
| gaaggcctgt | acaatgaact | gcagaaagat | aagatggcgg | aggcctacag | tgagattggg | 2040 |
| atgaaaggcg | agcgccggag | ggggcaaggg | cacgatggcc | tttaccaggg | tctcagtaca | 2100 |
| gccaccaagg | acacctacga | cgcccttcac | atgcaggccc | tgccccctcg | ctaa | 2154 |

```
<210> SEQ ID NO 5
<211> LENGTH: 717
<212> TYPE: PRT
<213> ORGANISM: artificial sequence
<220> FEATURE:
<223> OTHER INFORMATION: Synthetic construct

<400> SEQUENCE: 5
```

| | | | | | | | | | | | | | | |
|---|---|---|---|---|---|---|---|---|---|---|---|---|---|---|
| Met | Val | Arg | Gly | Val | Pro | Phe | Arg | His | Leu | Leu | Val | Leu | Gln | Leu |
| 1 | | | | 5 | | | | | 10 | | | | | 15 |
| Ala | Leu | Leu | Pro | Ala | Ala | Thr | Gln | Gly | Lys | Lys | Val | Val | Leu | Gly |
| | | | 20 | | | | | 25 | | | | | 30 | |
| Lys | Lys | Gly | Asp | Thr | Val | Glu | Leu | Thr | Cys | Thr | Ala | Ser | Gln | Lys |
| | | | 35 | | | | | 40 | | | | | 45 | |
| Lys | Ser | Ile | Gln | Phe | His | Trp | Lys | Asn | Ser | Asn | Gln | Ile | Lys | Ile |
| | | 50 | | | | | 55 | | | | | 60 | | |
| Leu | Gly | Asn | Gln | Gly | Ser | Phe | Leu | Thr | Lys | Gly | Pro | Ser | Lys | Leu |
| 65 | | | | | 70 | | | | | 75 | | | | 80 |
| Asn | Asp | Arg | Ala | Asp | Ser | Arg | Arg | Ser | Leu | Trp | Asp | Gln | Gly | Asn |
| | | | | 85 | | | | | 90 | | | | | 95 |
| Phe | Pro | Leu | Ile | Ile | Lys | Asn | Leu | Lys | Ile | Glu | Asp | Ser | Asp | Thr |
| | | | | 100 | | | | | 105 | | | | | |
| Tyr | Ile | Cys | Glu | Val | Glu | Asp | Gln | Lys | Glu | Glu | Val | Gln | Leu | Leu |
| | 110 | | | | | 115 | | | | | 120 | | | |
| Val | Phe | Gly | Leu | Thr | Ala | Asn | Ser | Asp | Thr | His | Leu | Leu | Gln | Gly |
| | | 125 | | | | | 130 | | | | | 135 | | |
| Gln | Ser | Leu | Thr | Leu | Thr | Leu | Glu | Ser | Pro | Pro | Gly | Ser | Ser | Pro |
| | 140 | | | | | 145 | | | | | 150 | | | |
| Ser | Val | Gln | Cys | Arg | Ser | Pro | Arg | Gly | Lys | Asn | Ile | Gln | Gly | Gly |
| | | 155 | | | | | 160 | | | | | 165 | | |
| Lys | Thr | Leu | Ser | Val | Ser | Gln | Leu | Glu | Leu | Gln | Asp | Ser | Gly | Thr |
| | 170 | | | | | 175 | | | | | 180 | | | |
| Trp | Thr | Cys | Thr | Val | Leu | Gln | Asn | Gln | Lys | Lys | Val | Glu | Phe | Lys |
| | 185 | | | | | 190 | | | | | 195 | | | |
| Ile | Asp | Ile | Val | Val | Leu | Ala | Phe | Gln | Lys | Ala | Ser | Gly | Gly | Gly |
| | 200 | | | | | 205 | | | | | 210 | | | |
| Gly | Ser | Gly | Gly | Gly | Ser | Gly | Gly | Gly | Ser | Gly | Gly | Gly | Ser | Gly |
| | | 215 | | | | | 220 | | | | | 225 | | |
| Gly | Gly | Ser | Gly | Gly | Gly | Ser | Gly | Gly | Gly | Ser | Gly | Gly | | |
| | | 230 | | | | | 235 | | | | | 240 | | |
| Gly | Gly | Ser | Gln | Val | Gln | Leu | Leu | Glu | Ser | Gly | Ala | Glu | Val | Lys |
| | | | 245 | | | | | 250 | | | | | 255 | |
| Lys | Pro | Gly | Ser | Ser | Val | Lys | Val | Ser | Cys | Lys | Ala | Ser | Gly | Asp |
| | | | 260 | | | | | 265 | | | | | 270 | |
| Thr | Phe | Ile | Arg | Tyr | Ser | Phe | Thr | Trp | Val | Arg | Gln | Ala | Pro | Gly |
| | | | 275 | | | | | 280 | | | | | 285 | |
| Gln | Gly | Leu | Glu | Trp | Met | Gly | Arg | Ile | Ile | Thr | Ile | Leu | Asp | Val |
| | | | 290 | | | | | 295 | | | | | 300 | |
| Ala | His | Tyr | Ala | Pro | His | Leu | Gln | Gly | Arg | Val | Thr | Ile | Thr | Ala |
| 305 | | | | | 310 | | | | | 315 | | | | 320 |
| Asp | Lys | Ser | Thr | Ser | Thr | Val | Tyr | Leu | Glu | Leu | Arg | Asn | Leu | Arg |
| | | | | 325 | | | | | 330 | | | | | 335 |
| Ser | Asp | Asp | Thr | Ala | Val | Tyr | Phe | Cys | Ala | Gly | Val | Tyr | Glu | Gly |
| | | | | 340 | | | | | 345 | | | | | 350 |
| Glu | Ala | Asp | Glu | Gly | Glu | Tyr | Asp | Asn | Asn | Gly | Phe | Leu | Lys | His |
| | | | | 355 | | | | | 360 | | | | | 365 |
| Trp | Gly | Gln | Gly | Thr | Leu | Val | Thr | Val | Thr | Ser | Gly | Gly | Gly | Gly |
| | | | | | | | | | | | | | | |
| Ser | Gly | Gly | Gly | | | | | | | | | | | |

370                 375                 380
Gly Ser Glu Leu Glu Leu Thr Gln Ser Pro Ala Thr Leu Ser Val Ser
385                 390                 395                 400

Pro Gly Glu Arg Ala Thr Leu Ser Cys Arg Ala Ser Glu Ser Val Ser
                405                 410                 415

Ser Asp Leu Ala Trp Tyr Gln Gln Lys Pro Gly Gln Ala Pro Arg Leu
            420                 425                 430

Leu Ile Tyr Gly Ala Ser Thr Arg Ala Thr Gly Val Pro Ala Arg Phe
        435                 440                 445

Ser Gly Ser Gly Ser Gly Ala Glu Phe Thr Leu Thr Ile Ser Ser Leu
    450                 455                 460

Gln Ser Glu Asp Phe Ala Val Tyr Tyr Cys Gln Gln Tyr Asn Asn Trp
465                 470                 475                 480

Pro Pro Arg Tyr Thr Phe Gly Gln Gly Thr Arg Leu Glu Ile Lys Ala
                485                 490                 495

Ala Ala Ile Glu Val Met Tyr Pro Pro Pro Tyr Leu Asp Asn Glu Lys
            500                 505                 510

Ser Asn Gly Thr Ile Ile His Val Lys Gly Lys His Leu Cys Pro Ser
        515                 520                 525

Pro Leu Phe Pro Gly Pro Ser Lys Pro Phe Trp Val Leu Val Val Val
    530                 535                 540

Gly Gly Val Leu Ala Cys Tyr Ser Leu Leu Val Thr Val Ala Phe Ile
545                 550                 555                 560

Ile Phe Trp Val Arg Ser Lys Arg Ser Arg Leu Leu His Ser Asp Tyr
                565                 570                 575

Met Asn Met Thr Pro Arg Arg Pro Gly Pro Thr Arg Lys His Tyr Gln
            580                 585                 590

Pro Tyr Ala Pro Pro Arg Asp Phe Ala Ala Tyr Arg Ser Arg Val Lys
        595                 600                 605

Phe Ser Arg Ser Ala Asp Ala Pro Ala Tyr Gln Gln Gly Gln Asn Gln
    610                 615                 620

Leu Tyr Asn Glu Leu Asn Leu Gly Arg Arg Glu Glu Tyr Asp Val Leu
625                 630                 635                 640

Asp Lys Arg Arg Gly Arg Asp Pro Glu Met Gly Gly Lys Pro Arg Arg
                645                 650                 655

Lys Asn Pro Gln Glu Gly Leu Tyr Asn Glu Leu Gln Lys Asp Lys Met
            660                 665                 670

Ala Glu Ala Tyr Ser Glu Ile Gly Met Lys Gly Glu Arg Arg Arg Gly
        675                 680                 685

Lys Gly His Asp Gly Leu Tyr Gln Gly Leu Ser Thr Ala Thr Lys Asp
    690                 695                 700

Thr Tyr Asp Ala Leu His Met Gln Ala Leu Pro Pro Arg
705                 710                 715

<210> SEQ ID NO 6
<211> LENGTH: 2079
<212> TYPE: DNA
<213> ORGANISM: artificial sequence
<220> FEATURE:
<223> OTHER INFORMATION: Synthetic construct

<400> SEQUENCE: 6
atggttcgag gcgtgccctt ccggcatctg ctgctggtgc tgcagctggc tctcctgcct    60
gccgccaccc agggcaagaa agtggtgctg ggcaaaaagg gcgacaccgt ggaactgacc   120

| | | |
|---|---|---|
| tgcaccgcca gccagaagaa gtccatccag ttccactgga agaacagcaa ccagatcaag | 180 | |
| atcctgggca accagggcag cttcctgacc aagggcccca gcaagctgaa cgaccgggcc | 240 | |
| gatagccggc ggagcctgtg ggaccagggc aatttcccac tgatcatcaa gaacctgaag | 300 | |
| atcgaggaca gcgacaccta catctgcgag gtcgaagatc agaaagaaga ggtgcagctg | 360 | |
| ctggtgttcg gcctgaccgc caactccgac acccatctgc tgcagggcca gagcctgacc | 420 | |
| ctcaccctgg aaagcccccc tggcagcagc cccagcgtgc agtgcagaag ccccagaggc | 480 | |
| aagaacatcc agggcggcaa gaccctgagc gtgtcccagc tggaactgca ggactccggc | 540 | |
| acctggacct gtaccgtgct gcagaaccag aaaaaggtcg agttcaagat cgacatcgtg | 600 | |
| gtgctggcct tccagaaggc ctctggcggt ggcggaagcg gaggcggtgg atctcaggtc | 660 | |
| cagctgctcg aatctggcgc cgaagtgaag aaacccggca gcagcgtgaa agtgtcctgc | 720 | |
| aaggccagcg gcgacaccct catccggtac agcttcacat gggtccgaca ggcccctggg | 780 | |
| cagggcctgg aatggatggg ccggatcatc accatcctgg acgtggccca ctacgcccca | 840 | |
| catctgcagg gcagagtgac catcaccgcc gacaagagca ccagcaccgt gtacctggaa | 900 | |
| ctgcggaacc tgcggagcga cgataccgcc gtctacttct gtgccggcgt gtacgagggc | 960 | |
| gaggccgatg agggcgagta cgacaacaac ggcttcctga gcactggggg ccagggcacc | 1020 | |
| ctcgtcaccg tgaccagcgg cggcggagga tctggcggag gtggaagtgg cggggaggt | 1080 | |
| agtgagctga aactcaccca gagccccgcc accctgtccg tgtctccagg cgagagagcc | 1140 | |
| accctgagct gcagagccag cgagagcgtg tccagcgacc tggcctggta tcagcagaag | 1200 | |
| cccggccagg cccccagact gctgatctac ggcgccagca ccagagccac aggcgtgcca | 1260 | |
| gccagattca gcggcagcgg tagcggagcc gagttcaccc tgaccatcag cagcctgcag | 1320 | |
| agcgaggact tgccgtgta ctactgccag cagtacaaca ctggcccccc agatacacc | 1380 | |
| ttcggccagg gaacccggct ggaaatcaag gcggccgcaa ttgaagttat gtatcctcct | 1440 | |
| ccttacctag acaatgagaa gagcaatgga accattatcc atgtgaaagg gaaacacctt | 1500 | |
| tgtccaagtc ccctatttcc cggaccttct aagccctttt gggtgctggt ggtggttggt | 1560 | |
| ggagtcctgg cttgctatag cttgctagta acagtggcct ttattatttt ctgggtgagg | 1620 | |
| agtaagagga gcaggctcct gcacagtgac tacatgaaca tgactccccg ccgccccggg | 1680 | |
| cccacccgca agcattacca gccctatgcc ccaccacgcg acttcgcagc ctatcgctcc | 1740 | |
| agagtgaagt tcagcaggag cgcagacgcc cccgcgtacc agcagggcca gaaccagctc | 1800 | |
| tataacgagc tcaatctagg acgaagagag gagtacgatg ttttggacaa gagacgtggc | 1860 | |
| cgggaccctg agatgggggg aaagccgaga aggaagaacc tcaggaagg cctgtacaat | 1920 | |
| gaactgcaga aagataagat ggcggaggcc tacagtgaga ttgggatgaa aggcgagcgc | 1980 | |
| cggaggggca aggggcacga tggcctttac cagggtctca gtacagccac caaggacacc | 2040 | |
| tacgacgccc ttcacatgca ggccctgccc cctcgctaa | 2079 | |

<210> SEQ ID NO 7
<211> LENGTH: 692
<212> TYPE: PRT
<213> ORGANISM: artificial sequence
<220> FEATURE:
<223> OTHER INFORMATION: Synthetic construct

<400> SEQUENCE: 7

Met Val Arg Gly Val Pro Phe Arg His Leu Leu Leu Val Leu Gln Leu
1               5                   10                  15

-continued

```
Ala Leu Leu Pro Ala Ala Thr Gln Gly Lys Lys Val Leu Gly Lys
             20                  25                  30
Lys Gly Asp Thr Val Glu Leu Thr Cys Thr Ala Ser Gln Lys Ser
         35                  40                  45
Ile Gln Phe His Trp Lys Asn Ser Asn Gln Ile Lys Ile Leu Gly Asn
 50                  55                  60
Gln Gly Ser Phe Leu Thr Lys Gly Pro Ser Lys Leu Asn Asp Arg Ala
 65                  70                  75                  80
Asp Ser Arg Arg Ser Leu Trp Asp Gln Gly Asn Phe Pro Leu Ile Ile
                 85                  90                  95
Lys Asn Leu Lys Ile Glu Asp Ser Asp Thr Tyr Ile Cys Glu Val Glu
                 100                 105                 110
Asp Gln Lys Glu Glu Val Gln Leu Leu Val Phe Gly Leu Thr Ala Asn
                 115                 120                 125
Ser Asp Thr His Leu Leu Gln Gly Gln Ser Leu Thr Leu Thr Leu Glu
 130                 135                 140
Ser Pro Pro Gly Ser Ser Pro Ser Val Gln Cys Arg Ser Pro Arg Gly
 145                 150                 155                 160
Lys Asn Ile Gln Gly Gly Lys Thr Leu Ser Val Ser Gln Leu Glu Leu
                 165                 170                 175
Gln Asp Ser Gly Thr Trp Thr Cys Thr Val Leu Gln Asn Gln Lys Lys
                 180                 185                 190
Val Glu Phe Lys Ile Asp Ile Val Val Leu Ala Phe Gln Lys Ala Ser
                 195                 200                 205
Gly Gly Gly Gly Ser Gly Gly Gly Ser Gln Val Gln Leu Leu Glu
 210                 215                 220
Ser Gly Ala Glu Val Lys Lys Pro Gly Ser Ser Val Lys Val Ser Cys
 225                 230                 235                 240
Lys Ala Ser Gly Asp Thr Phe Ile Arg Tyr Ser Phe Thr Trp Val Arg
                 245                 250                 255
Gln Ala Pro Gly Gln Gly Leu Glu Trp Met Gly Arg Ile Ile Thr Ile
                 260                 265                 270
Leu Asp Val Ala His Tyr Ala Pro His Leu Gln Gly Arg Val Thr Ile
                 275                 280                 285
Thr Ala Asp Lys Ser Thr Ser Thr Val Tyr Leu Glu Leu Arg Asn Leu
 290                 295                 300
Arg Ser Asp Asp Thr Ala Val Tyr Phe Cys Ala Gly Val Tyr Glu Gly
 305                 310                 315                 320
Glu Ala Asp Glu Gly Glu Tyr Asp Asn Asn Gly Phe Leu Lys His Trp
                 325                 330                 335
Gly Gln Gly Thr Leu Val Thr Val Thr Ser Gly Gly Gly Ser Gly
                 340                 345                 350
Gly Gly Gly Ser Gly Gly Gly Ser Glu Leu Glu Leu Thr Gln Ser
                 355                 360                 365
Pro Ala Thr Leu Ser Val Ser Pro Gly Glu Arg Ala Thr Leu Ser Cys
 370                 375                 380
Arg Ala Ser Glu Ser Val Ser Ser Asp Leu Ala Trp Tyr Gln Gln Lys
 385                 390                 395                 400
Pro Gly Gln Ala Pro Arg Leu Leu Ile Tyr Gly Ala Ser Thr Arg Ala
                 405                 410                 415
Thr Gly Val Pro Ala Arg Phe Ser Gly Ser Gly Ser Gly Ala Glu Phe
                 420                 425                 430
Thr Leu Thr Ile Ser Ser Leu Gln Ser Glu Asp Phe Ala Val Tyr Tyr
```

```
            435              440              445
Cys Gln Gln Tyr Asn Asn Trp Pro Pro Arg Tyr Thr Phe Gly Gln Gly
    450              455              460

Thr Arg Leu Glu Ile Lys Ala Ala Ile Glu Val Met Tyr Pro Pro
465              470              475              480

Pro Tyr Leu Asp Asn Glu Lys Ser Asn Gly Thr Ile Ile His Val Lys
            485              490              495

Gly Lys His Leu Cys Pro Ser Pro Leu Phe Pro Gly Pro Ser Lys Pro
            500              505              510

Phe Trp Val Leu Val Val Gly Gly Val Leu Ala Cys Tyr Ser Leu
            515              520              525

Leu Val Thr Val Ala Phe Ile Ile Phe Trp Val Arg Ser Lys Arg Ser
    530              535              540

Arg Leu Leu His Ser Asp Tyr Met Asn Met Thr Pro Arg Arg Pro Gly
545              550              555              560

Pro Thr Arg Lys His Tyr Gln Pro Tyr Ala Pro Pro Arg Asp Phe Ala
            565              570              575

Ala Tyr Arg Ser Arg Val Lys Phe Ser Arg Ser Ala Asp Ala Pro Ala
            580              585              590

Tyr Gln Gln Gly Gln Asn Gln Leu Tyr Asn Glu Leu Asn Leu Gly Arg
            595              600              605

Arg Glu Glu Tyr Asp Val Leu Asp Lys Arg Arg Gly Arg Asp Pro Glu
    610              615              620

Met Gly Gly Lys Pro Arg Arg Lys Asn Pro Gln Glu Gly Leu Tyr Asn
625              630              635              640

Glu Leu Gln Lys Asp Lys Met Ala Glu Ala Tyr Ser Glu Ile Gly Met
            645              650              655

Lys Gly Glu Arg Arg Arg Gly Lys Gly His Asp Gly Leu Tyr Gln Gly
            660              665              670

Leu Ser Thr Ala Thr Lys Asp Thr Tyr Asp Ala Leu His Met Gln Ala
            675              680              685

Leu Pro Pro Arg
    690

<210> SEQ ID NO 8
<211> LENGTH: 2127
<212> TYPE: DNA
<213> ORGANISM: artificial sequence
<220> FEATURE:
<223> OTHER INFORMATION: Synthetic construct

<400> SEQUENCE: 8
atggttcgag gcgtgccctt ccggcatctg ctgctggtgc tgcagctggc tctcctgcct      60
gccgccaccc agggcaagaa agtggtgctg ggcaaaaagg gcgacaccgt ggaactgacc     120
tgcaccgcca gccagaagaa gtccatccag ttccactgga gaacagcaa ccagatcaag      180 atcctgggca accagggcag cttcctgacc aagggcccca gcaagctgaa cgaccgggcc     240
gatagccggc ggagcctgtg ggaccagggc aatttcccac tgatcatcaa gaacctgaag     300
atcgaggaca gcgacaccta catctgcgag gtcgaagatc agaaagaaga ggtgcagctg     360
ctggtgttcg gcctgaccgc caactccgac acccatctgc tgcagggcca gagcctgacc     420
ctcacccctg gaaagccccc tggcagcagc cccagcgtgc agtgcagaag ccccagaggc     480
aagaacatcc agggcggcaa gaccctgagc gtgtcccagc tggaactgca ggactccggc     540
acctggacct gtaccgtgct gcagaaccag aaaaaggtcg agttcaagat cgacatcgtg     600
```

```
gtgctggcct tccagaaggc ctctggcggc ggaggatctg gcggaggtgg aagtggcggg    660
ggaggtagtg gcggaggcgg atcaggtggc ggaggttcag gcggtggcgg aagcggaggc    720
ggtggatctg aagtgcagct ggtgcagtct ggcgccgaag tgaagaaacc tggcgccacc    780
gtgaagatca gctgcaaggt gtccggctac accttcaccg actactacat gcactgggtg    840
cagcaggccc ctggcaaggg cctggaatgg atgggactgg tggaccccga ggacggcgag    900
acaatctacg ccgagaagtt ccagggcaga gtgaccatca ccgccgatac cagcaccgac    960
accgcctaca tggaactgag cagcctgcgg agcgaggaca ccgccgtgta ctactgtgcc   1020
accgagcgga ccgattactg gggccaggga acactcgtga ccgtgtcaag tggcggcgga   1080
ggatctggcg gaggtggaag tggcggggga ggtagtgaga tcgtgctgac ccagagcccc   1140
ctgtccctgt ctgtgacacc tggcgagcct gccagcatct cctgcagaag cagccagagc   1200
ctgctggact ccgacgacgg caacacctac ctggactggt atctgcagaa acccggccag   1260 tcccccccagc tgctgatcta cgaggtgtcc aaccggttca gcggcgtgcc cgatagattt   1320
tccggctctg gcagcggcac cgacttcacc ctgaagatta gccgggtgga agccgaggac   1380
gtgggcgtgt actattgcat gcagagcatc cagctgcctt ggaccttcgg ccagggcacc   1440
aagctggaaa tcaagagagc ggccgcaatt gaagttatgt atcctcctcc ttacctagac   1500
aatgagaaga gcaatggaac cattatccat gtgaaaggga aacacctttg tccaagtccc   1560
ctatttcccg accttctaa gccctttttgg gtgctggtgg tggttggtgg agtcctggct   1620
tgctatagct tgctagtaac agtggccttt attattttct gggtgaggag taagaggagc   1680
aggctcctgc acagtgacta catgaacatg actccccgcc gccccgggcc cacccgcaag   1740
cattaccagc cctatgcccc accacgcgac ttcgcagcct atcgctccag agtgaagttc   1800
agcaggagcg cagacgcccc cgcgtaccag cagggccaga accagctcta taacgagctc   1860
aatctaggac gaagagagga gtacgatgtt ttggacaaga cgtggccg ggaccctgag    1920 atggggggaa agccgagaag gaagaaccct caggaaggcc tgtacaatga actgcagaaa   1980
gataagatgg cggaggccta cagtgagatt gggatgaaag cgagcgccg gaggggcaag   2040 gggcacgatg gcctttacca gggtctcagt acagccacca aggacaccta cgacgccctt   2100
cacatgcagg ccctgccccc tcgctaa                                        2127
```

<210> SEQ ID NO 9
<211> LENGTH: 708
<212> TYPE: PRT
<213> ORGANISM: artificial sequence
<220> FEATURE:
<223> OTHER INFORMATION: Synthetic construct

<400> SEQUENCE: 9

Met Val Arg Gly Val Pro Phe Arg His Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile

-continued

```
                85                  90                  95
Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
                115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
                195                 200                 205

Gly Gly Gly Gly Ser Gly Gly Gly Ser Gly Gly Gly Gly Ser Gly
                210                 215                 220

Gly Gly Ser Gly Gly Gly Ser Gly Gly Gly Ser Gly Gly
225                 230                 235                 240

Gly Gly Ser Glu Val Gln Leu Val Gln Ser Gly Ala Glu Val Lys Lys
                245                 250                 255

Pro Gly Ala Thr Val Lys Ile Ser Cys Lys Val Ser Gly Tyr Thr Phe
                260                 265                 270

Thr Asp Tyr Tyr Met His Trp Val Gln Gln Ala Pro Gly Lys Gly Leu
                275                 280                 285

Glu Trp Met Gly Leu Val Asp Pro Glu Asp Gly Glu Thr Ile Tyr Ala
                290                 295                 300

Glu Lys Phe Gln Gly Arg Val Thr Ile Thr Ala Asp Thr Ser Thr Asp
305                 310                 315                 320

Thr Ala Tyr Met Glu Leu Ser Ser Leu Arg Ser Glu Asp Thr Ala Val
                325                 330                 335

Tyr Tyr Cys Ala Thr Glu Arg Thr Asp Tyr Trp Gly Gln Gly Thr Leu
                340                 345                 350

Val Thr Val Ser Ser Gly Gly Gly Ser Gly Gly Gly Gly Ser Gly
                355                 360                 365

Gly Gly Ser Glu Ile Val Leu Thr Gln Ser Pro Leu Ser Leu
                370                 375                 380

Val Thr Pro Gly Glu Pro Ala Ser Ile Ser Cys Arg Ser Ser Gln Ser
385                 390                 395                 400

Leu Leu Asp Ser Asp Asp Gly Asn Thr Tyr Leu Asp Trp Tyr Leu Gln
                405                 410                 415

Lys Pro Gly Gln Ser Pro Gln Leu Leu Ile Tyr Glu Val Ser Asn Arg
                420                 425                 430

Phe Ser Gly Val Pro Asp Arg Phe Ser Gly Ser Gly Ser Gly Thr Asp
                435                 440                 445

Phe Thr Leu Lys Ile Ser Arg Val Glu Ala Glu Asp Val Gly Val Tyr
                450                 455                 460

Tyr Cys Met Gln Ser Ile Gln Leu Pro Trp Thr Phe Gly Gln Gly Thr
465                 470                 475                 480

Lys Leu Glu Ile Lys Arg Ala Ala Ala Ile Glu Val Met Tyr Pro Pro
                485                 490                 495

Pro Tyr Leu Asp Asn Glu Lys Ser Asn Gly Thr Ile Ile His Val Lys
                500                 505                 510
```

Gly Lys His Leu Cys Pro Ser Pro Leu Phe Pro Gly Pro Ser Lys Pro
            515                 520                 525

Phe Trp Val Leu Val Val Gly Gly Val Leu Ala Cys Tyr Ser Leu
530                 535                 540

Leu Val Thr Val Ala Phe Ile Ile Phe Trp Val Arg Ser Lys Arg Ser
545                 550                 555                 560

Arg Leu Leu His Ser Asp Tyr Met Asn Met Thr Pro Arg Arg Pro Gly
            565                 570                 575

Pro Thr Arg Lys His Tyr Gln Pro Tyr Ala Pro Arg Asp Phe Ala
            580                 585                 590

Ala Tyr Arg Ser Arg Val Lys Phe Ser Arg Ser Ala Asp Ala Pro Ala
            595                 600                 605

Tyr Gln Gln Gly Gln Asn Gln Leu Tyr Asn Glu Leu Asn Leu Gly Arg
            610                 615                 620

Arg Glu Glu Tyr Asp Val Leu Asp Lys Arg Arg Gly Arg Asp Pro Glu
625                 630                 635                 640

Met Gly Gly Lys Pro Arg Arg Lys Asn Pro Gln Glu Gly Leu Tyr Asn
            645                 650                 655

Glu Leu Gln Lys Asp Lys Met Ala Glu Ala Tyr Ser Glu Ile Gly Met
            660                 665                 670

Lys Gly Glu Arg Arg Arg Gly Lys Gly His Asp Gly Leu Tyr Gln Gly
            675                 680                 685

Leu Ser Thr Ala Thr Lys Asp Thr Tyr Asp Ala Leu His Met Gln Ala
            690                 695                 700

Leu Pro Pro Arg
705

<210> SEQ ID NO 10
<211> LENGTH: 110
<212> TYPE: PRT
<213> ORGANISM: artificial sequence
<220> FEATURE:
<223> OTHER INFORMATION: Synthetic construct

<400> SEQUENCE: 10

Gln Ser Ala Leu Thr Gln Pro Ala Ser Val Ser Gly Ser Pro Gly Gln
1               5                   10                  15

Ser Ile Thr Ile Ser Cys Asn Gly Thr Ser Asn Asp Val Gly Gly Tyr
            20                  25                  30

Glu Ser Val Ser Trp Tyr Gln Gln His Pro Gly Lys Ala Pro Lys Val
        35                  40                  45

Val Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Gly Asp Tyr Tyr Cys Lys Ser Leu Thr Ser Thr
                85                  90                  95

Arg Arg Arg Val Phe Gly Thr Gly Thr Lys Leu Thr Val Leu
            100                 105                 110

<210> SEQ ID NO 11
<211> LENGTH: 136
<212> TYPE: PRT
<213> ORGANISM: artificial sequence
<220> FEATURE:
<223> OTHER INFORMATION: Synthetic construct

```
<400> SEQUENCE: 11

Gln Arg Leu Val Glu Ser Gly Gly Val Val Gln Pro Gly Ser Ser
1               5                   10                  15

Leu Arg Leu Ser Cys Ala Ala Ser Gly Phe Asp Phe Ser Arg Gln Gly
                20                  25                  30

Met His Trp Val Arg Gln Ala Pro Gly Gln Gly Leu Glu Trp Val Ala
            35                  40                  45

Phe Ile Lys Tyr Asp Gly Ser Glu Lys Tyr His Ala Asp Ser Val Trp
        50                  55                  60

Gly Arg Leu Ser Ile Ser Arg Asp Asn Ser Lys Asp Thr Leu Tyr Leu
65                  70                  75                  80

Gln Met Asn Ser Leu Arg Val Glu Asp Thr Ala Thr Tyr Phe Cys Val
                85                  90                  95

Arg Glu Ala Gly Gly Pro Asp Tyr Arg Asn Gly Tyr Asn Tyr Tyr Asp
            100                 105                 110

Phe Tyr Asp Gly Tyr Tyr Asn Tyr His Tyr Met Asp Val Trp Gly Lys
        115                 120                 125

Gly Thr Thr Val Thr Val Ser Ser
    130                 135

<210> SEQ ID NO 12
<211> LENGTH: 110
<212> TYPE: PRT
<213> ORGANISM: artificial sequence
<220> FEATURE:
<223> OTHER INFORMATION: Synthetic construct

<400> SEQUENCE: 12

Gln Ser Ala Leu Thr Gln Pro Ala Ser Val Ser Gly Ser Pro Gly Gln
1               5                   10                  15

Thr Ile Thr Ile Ser Cys Asn Gly Thr Ser Ser Asp Val Gly Gly Phe
                20                  25                  30

Asp Ser Val Ser Trp Tyr Gln Gln Ser Pro Gly Lys Ala Pro Lys Val
            35                  40                  45

Met Val Phe Asp Val Ser His Arg Pro Ser Gly Ile Ser Asn Arg Phe
        50                  55                  60

Ser Gly Ser Lys Ser Gly Asn Thr Ala Ser Leu Thr Ile Ser Gly Leu
65                  70                  75                  80

His Ile Glu Asp Glu Gly Asp Tyr Phe Cys Ser Ser Leu Thr Asp Arg
                85                  90                  95

Ser His Arg Ile Phe Gly Gly Thr Lys Val Thr Val Leu
            100                 105                 110

<210> SEQ ID NO 13
<211> LENGTH: 137
<212> TYPE: PRT
<213> ORGANISM: artificial sequence
<220> FEATURE:
<223> OTHER INFORMATION: Synthetic construct

<400> SEQUENCE: 13

Gln Glu Gln Leu Val Glu Ser Gly Gly Gly Val Val Gln Pro Gly Gly
1               5                   10                  15

Ser Leu Arg Leu Ser Cys Leu Ala Ser Gly Phe Thr Phe His Lys Tyr
                20                  25                  30

Gly Met His Trp Val Arg Gln Ala Pro Gly Lys Gly Leu Glu Trp Val
            35                  40                  45
```

```
Ala Leu Ile Ser Asp Asp Gly Met Arg Lys Tyr His Ser Asp Ser Met
    50                  55                  60

Trp Gly Arg Val Thr Ile Ser Arg Asp Asn Ser Lys Asn Thr Leu Tyr
65                  70                  75                  80

Leu Gln Phe Ser Ser Leu Lys Val Glu Asp Thr Ala Met Phe Phe Cys
                85                  90                  95

Ala Arg Glu Ala Gly Gly Pro Ile Trp His Asp Asp Val Lys Tyr Tyr
            100                 105                 110

Asp Phe Asn Asp Gly Tyr Tyr Asn Tyr His Tyr Met Asp Val Trp Gly
        115                 120                 125

Lys Gly Thr Thr Val Thr Val Ser Ser
    130                 135
```

<210> SEQ ID NO 14
<211> LENGTH: 112
<212> TYPE: PRT
<213> ORGANISM: artificial sequence
<220> FEATURE:
<223> OTHER INFORMATION: Synthetic construct

<400> SEQUENCE: 14

```
Asp Thr Val Val Thr Gln Ser Pro Leu Ser Leu Pro Val Thr Pro Gly
1               5                   10                  15

Glu Ala Ala Ser Met Ser Cys Ser Ser Thr Gln Ser Leu Arg His Ser
                20                  25                  30

Asn Gly Ala Asn Tyr Leu Ala Trp Tyr Gln His Lys Pro Gly Gln Ser
            35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Ala Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110
```

<210> SEQ ID NO 15
<211> LENGTH: 141
<212> TYPE: PRT
<213> ORGANISM: artificial sequence
<220> FEATURE:
<223> OTHER INFORMATION: Synthetic construct

<400> SEQUENCE: 15

```
Gln Val Gln Leu Val Gln Ser Gly Pro Glu Val Lys Lys Pro Gly Ser
1               5                   10                  15

Ser Val Lys Val Ser Cys Lys Ala Ser Gly Asn Thr Phe Ser Lys Tyr
                20                  25                  30

Asp Val His Trp Val Arg Gln Ala Thr Gly Gln Gly Leu Glu Trp Val
            35                  40                  45

Gly Trp Met Ser His Glu Gly Asp Lys Thr Glu Ser Ala Gln Arg Phe
    50                  55                  60

Lys Gly Arg Val Thr Phe Thr Arg Asp Thr Ser Ala Ser Thr Ala Tyr
65                  70                  75                  80

Met Glu Leu Arg Gly Leu Thr Ser Asp Asp Thr Ala Ile Tyr Tyr Cys
                85                  90                  95

Thr Arg Gly Ser Lys His Arg Leu Arg Asp Tyr Val Leu Tyr Asp Asp
            100                 105                 110
```

Tyr Gly Leu Ile Asn Tyr Gln Glu Trp Asn Asp Tyr Leu Glu Phe Leu
        115                 120                 125

Asp Val Trp Gly His Gly Thr Ala Val Thr Val Ser Ser
    130                 135                 140

<210> SEQ ID NO 16
<211> LENGTH: 112
<212> TYPE: PRT
<213> ORGANISM: artificial sequence
<220> FEATURE:
<223> OTHER INFORMATION: Synthetic construct

<400> SEQUENCE: 16

Asp Thr Val Val Thr Gln Ser Pro Leu Ser Leu Pro Val Thr Pro Gly
1               5                   10                  15

Glu Ala Ala Ser Met Ser Cys Ser Ser Thr Gln Ser Leu Arg His Ser
            20                  25                  30

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Ala Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110

<210> SEQ ID NO 17
<211> LENGTH: 141
<212> TYPE: PRT
<213> ORGANISM: artificial sequence
<220> FEATURE:
<223> OTHER INFORMATION: Synthetic construct

<400> SEQUENCE: 17

Gln Val Gln Leu Val Gln Ser Gly Pro Glu Val Lys Lys Pro Gly Ser
1               5                   10                  15

Ser Val Lys Val Ser Cys Lys Ala Ser Gly Asn Thr Phe Ser Lys Tyr
            20                  25                  30

Asp Val His Trp Val Arg Gln Ala Thr Gly Gln Gly Leu Glu Trp Val
        35                  40                  45

Gly Trp Ile Ser His Glu Arg Asp Lys Thr Glu Ser Ala Gln Arg Phe
    50                  55                  60

Lys Gly Arg Val Thr Phe Thr Arg Asp Thr Ser Ala Thr Thr Ala Tyr
65                  70                  75                  80

Met Glu Leu Arg Gly Leu Thr Ser Asp Asp Thr Ala Ile Tyr Tyr Cys
                85                  90                  95

Thr Arg Gly Ser Lys His Arg Leu Arg Asp Tyr Val Leu Tyr Asp Asp
            100                 105                 110

Tyr Gly Leu Ile Asn Tyr Gln Glu Trp Asn Asp Tyr Leu Glu Phe Leu
        115                 120                 125

Asp Val Trp Gly His Gly Thr Ala Val Thr Val Ser Ser
    130                 135                 140

<210> SEQ ID NO 18
<211> LENGTH: 112
<212> TYPE: PRT

<213> ORGANISM: artificial sequence
<220> FEATURE:
<223> OTHER INFORMATION: Synthetic construct

<400> SEQUENCE: 18

```
Asp Thr Val Val Thr Gln Ser Pro Leu Ser Leu Pro Val Thr Pro Gly
1               5                   10                  15

Glu Ala Ala Ser Met Ser Cys Thr Ser Thr Gln Ser Leu Arg His Ser
            20                  25                  30

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
    50                  55                  60

Asp Arg Phe Ser Gly Ser Gly Ser Gly Thr His Phe Thr Leu Lys Ile
65                  70                  75                  80

Ser Arg Val Glu Pro Glu Asp Ala Ala Ile Tyr Tyr Cys Met Gln Gly
                85                  90                  95

Leu Asn Arg Pro Trp Thr Phe Gly Lys Gly Thr Lys Leu Glu Ile Lys
            100                 105                 110
```

<210> SEQ ID NO 19
<211> LENGTH: 141
<212> TYPE: PRT
<213> ORGANISM: artificial sequence
<220> FEATURE:
<223> OTHER INFORMATION: Synthetic construct

<400> SEQUENCE: 19

```
Gln Val Gln Leu Glu Gln Ser Gly Ala Glu Val Lys Lys Pro Gly Ser
1               5                   10                  15

Ser Val Lys Val Ser Cys Lys Ala Ser Gly Asn Thr Phe Ser Lys Tyr
            20                  25                  30

Asp Val His Trp Val Arg Gln Ala Thr Gly Gln Gly Leu Glu Trp Val
        35                  40                  45

Gly Trp Met Ser His Glu Gly Asp Lys Thr Glu Ser Ala Gln Arg Phe
    50                  55                  60

Lys Gly Arg Val Thr Phe Thr Arg Asp Thr Ser Ala Ser Thr Ala Tyr
65                  70                  75                  80

Met Glu Leu Arg Gly Leu Thr Ser Asp Thr Ala Ile Tyr Tyr Cys
                85                  90                  95

Thr Arg Gly Ser Lys His Arg Leu Arg Asp Tyr Val Leu Tyr Asp Asp
            100                 105                 110

Tyr Gly Leu Ile Asn Tyr Gln Glu Trp Asn Asp Tyr Leu Glu Phe Leu
        115                 120                 125

Asp Val Trp Gly His Gly Thr Ala Val Thr Val Ser Ser
    130                 135                 140
```

<210> SEQ ID NO 20
<211> LENGTH: 112
<212> TYPE: PRT
<213> ORGANISM: artificial sequence
<220> FEATURE:
<223> OTHER INFORMATION: Synthetic construct

<400> SEQUENCE: 20

```
Asp Thr Val Val Thr Gln Ser Pro Leu Ser Leu Ser Val Thr Pro Gly
1               5                   10                  15

Glu Ala Ala Ser Met Ser Cys Thr Ser Thr Gln Ser Leu Arg His Ser
            20                  25                  30
```

Asn Gly Ala Asn Tyr Leu Ala Trp Tyr Gln His Lys Pro Gly Gln Ser
        35                  40                  45

Pro Arg Leu Leu Ile Arg Leu Gly Ser Gln Arg Ala Ser Gly Val Pro
 50                  55                  60

Asp Arg Phe Ser Gly Ser Gly Ser Gly Thr His Phe Thr Leu Lys Ile
 65                  70                  75                  80

Ser Arg Val Glu Ala Asp Asp Ala Ala Ile Tyr Tyr Cys Met Gln Gly
                 85                  90                  95

Leu Asn Arg Pro Trp Thr Phe Gly Lys Gly Thr Lys Leu Glu Ile Lys
            100                 105                 110

<210> SEQ ID NO 21
<211> LENGTH: 141
<212> TYPE: PRT
<213> ORGANISM: artificial sequence
<220> FEATURE:
<223> OTHER INFORMATION: Synthetic construct

<400> SEQUENCE: 21

Gln Val Gln Leu Val Gln Ser Gly Ala Glu Val Lys Lys Pro Gly Ser
1               5                   10                  15

Ser Val Lys Val Ser Cys Lys Ala Ser Gly Asn Thr Phe Arg Lys Tyr
                20                  25                  30

Asp Val His Trp Val Arg Gln Ala Thr Gly Gln Gly Leu Glu Trp Val
            35                  40                  45

Gly Trp Met Ser His Glu Gly Asp Lys Thr Glu Ser Ala Gln Arg Phe
        50                  55                  60

Lys Gly Arg Val Ser Phe Thr Arg Asp Asn Ser Ala Ser Thr Ala Tyr
65                  70                  75                  80

Ile Glu Leu Arg Gly Leu Thr Ser Asp Asp Thr Ala Ile Tyr Tyr Cys
                85                  90                  95

Thr Gly Gly Ser Lys His Arg Leu Arg Asp Tyr Val Leu Tyr Asp Asp
            100                 105                 110

Tyr Gly Leu Ile Asn Gln Gln Glu Trp Asn Asp Tyr Leu Glu Phe Leu
        115                 120                 125

Asp Val Trp Gly His Gly Thr Ala Val Thr Val Ser Ser
            130                 135                 140

<210> SEQ ID NO 22
<211> LENGTH: 112
<212> TYPE: PRT
<213> ORGANISM: artificial sequence
<220> FEATURE:
<223> OTHER INFORMATION: Synthetic construct

<400> SEQUENCE: 22

Glu Val Val Ile Thr Gln Ser Pro Leu Phe Leu Pro Val Thr Pro Gly
1               5                   10                  15

Glu Ala Ala Ser Leu Ser Cys Lys Cys Ser His Ser Leu Gln His Ser
                20                  25                  30

Thr Gly Ala Asn Tyr Leu Ala Trp Tyr Leu Gln Arg Pro Gly Gln Thr
            35                  40                  45

Pro Arg Leu Leu Ile His Leu Ala Thr His Arg Ala Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ser Asp Asp Val Gly Thr Tyr Tyr Cys Met Gln Gly

```
                    85                  90                  95

Leu His Ser Pro Trp Thr Phe Gly Gln Gly Thr Lys Val Glu Ile Lys
                100                 105                 110

<210> SEQ ID NO 23
<211> LENGTH: 140
<212> TYPE: PRT
<213> ORGANISM: artificial sequence
<220> FEATURE:
<223> OTHER INFORMATION: Synthetic construct

<400> SEQUENCE: 23

Gln Val Gln Leu Val Gln Ser Gly Ala Glu Val Lys Lys Pro Gly Ser
1               5                   10                  15

Ser Val Lys Val Ser Cys Lys Ala Ser Gly Asn Ser Phe Ser Asn His
                20                  25                  30

Asp Val His Trp Val Arg Gln Ala Thr Gly Gln Gly Leu Glu Trp Met
            35                  40                  45

Gly Trp Met Ser His Glu Gly Asp Lys Thr Gly Leu Ala Gln Lys Phe
    50                  55                  60

Gln Gly Arg Val Thr Ile Thr Arg Asp Ser Gly Ala Ser Thr Val Tyr
65                  70                  75                  80

Met Glu Leu Arg Gly Leu Thr Ala Asp Asp Thr Ala Ile Tyr Tyr Cys
                85                  90                  95

Leu Thr Gly Ser Lys His Arg Leu Arg Asp Tyr Phe Leu Tyr Asn Glu
                100                 105                 110

Tyr Gly Pro Asn Tyr Glu Glu Trp Gly Asp Tyr Leu Ala Thr Leu Asp
            115                 120                 125

Val Trp Gly His Gly Thr Ala Val Thr Val Ser Ser
    130                 135                 140

<210> SEQ ID NO 24
<211> LENGTH: 212
<212> TYPE: PRT
<213> ORGANISM: artificial sequence
<220> FEATURE:
<223> OTHER INFORMATION: Synthetic construct

<400> SEQUENCE: 24

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Thr Trp
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
    50                  55                  60

Ser Gly Ser Gly Thr Asp Phe Ser Leu Thr Ile Asn Ser Leu Gln Pro
65                  70                  75                  80

Glu Asp Phe Ala Thr Tyr Tyr Cys Gln Gln Ala Asn Ser Phe Phe Thr
                85                  90                  95

Phe Gly Gly Gly Thr Lys Val Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
    130                 135                 140
```

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Leu Tyr Ala
            180                 185                 190

Cys Glu Val Thr His Gln Gly Leu Ser Ser Pro Val Thr Lys Ser Phe
            195                 200                 205

Asn Arg Gly Glu
    210

<210> SEQ ID NO 25
<211> LENGTH: 215
<212> TYPE: PRT
<213> ORGANISM: artificial sequence
<220> FEATURE:
<223> OTHER INFORMATION: Synthetic construct

<400> SEQUENCE: 25

Glu Val Gln Leu Val Gln Ser Gly Ala Glu Val Lys Lys Pro Gly Ala
1               5                   10                  15

Thr Val Lys Ile Ser Cys Lys Ala Ser Gly Tyr Thr Phe Ser Asp Phe
            20                  25                  30

Tyr Met Tyr Trp Val Arg Gln Ala Pro Gly Lys Gly Leu Glu Trp Met
        35                  40                  45

Gly Leu Ile Asp Pro Glu Asp Ala Asp Thr Met Tyr Ala Glu Lys Phe
    50                  55                  60

Arg Gly Arg Val Thr Ile Thr Ala Asp Thr Ser Thr Asp Thr Gly Tyr
65                  70                  75                  80

Leu Glu Leu Ser Ser Leu Arg Ser Glu Asp Thr Ala Val Tyr Tyr Cys
                85                  90                  95

Ala Ala Asp Pro Trp Glu Leu Asn Ala Phe Asn Val Trp Gly Gln Gly
            100                 105                 110

Thr Leu Val Ser Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys
    210                 215

<210> SEQ ID NO 26
<211> LENGTH: 193
<212> TYPE: PRT
<213> ORGANISM: artificial sequence
<220> FEATURE:
<223> OTHER INFORMATION: Synthetic construct

<400> SEQUENCE: 26

Ser Val Gly Asp Arg Val Thr Ile Thr Cys Arg Ala Ser Gln Ser Ile
1               5                   10                  15

```
Ser Asn Trp Leu Ala Trp Tyr Gln Gln Lys Pro Gly Arg Ala Pro Lys
            20                  25                  30

Leu Leu Met Tyr Lys Ala Ser Ser Leu Lys Ser Gly Val Pro Ser Arg
        35                  40                  45

Phe Ser Gly Ser Gly Ser Gly Thr Glu Phe Thr Leu Thr Ile Ser Ser
 50                  55                  60

Leu Gln Ser Asp Asp Phe Ala Thr Tyr Tyr Cys Gln Gln His Asp Ser
65                  70                  75                  80

Ser Pro Tyr Thr Phe Gly Gln Gly Thr Lys Leu Glu Ile Lys Arg Thr
                85                  90                  95

Val Ala Ala Pro Ser Val Phe Ile Phe Pro Pro Ser Asp Glu Gln Leu
            100                 105                 110

Lys Ser Gly Thr Ala Ser Val Val Cys Leu Leu Asn Asn Phe Tyr Pro
        115                 120                 125

Arg Glu Ala Lys Val Gln Trp Lys Val Asp Asn Ala Leu Gln Ser Gly
    130                 135                 140

Asn Ser Gln Glu Ser Val Thr Glu Gln Asp Ser Lys Asp Ser Thr Tyr
145                 150                 155                 160

Ser Leu Ser Ser Thr Leu Thr Leu Ser Lys Ala Asp Tyr Glu Lys His
                165                 170                 175

Lys Val Tyr Ala Cys Glu Val Thr His Gln Gly Leu Ser Ser Pro Val
            180                 185                 190

Thr

<210> SEQ ID NO 27
<211> LENGTH: 215
<212> TYPE: PRT
<213> ORGANISM: artificial sequence
<220> FEATURE:
<223> OTHER INFORMATION: Synthetic construct

<400> SEQUENCE: 27

Ala Glu Val Lys Lys Pro Gly Ser Ser Val Lys Val Ser Cys Lys Ala
1               5                   10                  15

Ser Gly Gly Thr Phe Ser Asn Tyr Ala Ile Asn Trp Val Arg Gln Ala
            20                  25                  30

Pro Gly Gln Gly Leu Glu Trp Met Gly Gly Ile Ile Pro Ile Phe Asn
        35                  40                  45

Ile Ala His Tyr Ala Gln Arg Phe Gln Gly Arg Val Ser Ile Thr Ala
 50                  55                  60

Asp Glu Ser Thr Ser Thr Ala Tyr Met Glu Leu Ser Ser Leu Arg Ser
65                  70                  75                  80

Glu Asp Thr Ala Val Phe Tyr Cys Ala Ser Pro Tyr Pro Asn Asp Tyr
                85                  90                  95

Asn Asp Tyr Ala Pro Glu Glu Gly Met Ser Trp Tyr Phe Asp Leu Trp
            100                 105                 110

Gly Arg Gly Thr Leu Val Thr Val Ser Pro Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175
```

```
Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
            195                 200                 205

His Lys Pro Ser Asn Thr Lys
        210                 215

<210> SEQ ID NO 28
<211> LENGTH: 190
<212> TYPE: PRT
<213> ORGANISM: artificial sequence
<220> FEATURE:
<223> OTHER INFORMATION: Synthetic construct

<400> SEQUENCE: 28

Ser Val Gly Asp Arg Val Thr Ile Thr Cys Arg Ala Ser Gln Asn Ile
1               5                   10                  15

Asn Asn Tyr Leu Asn Trp Tyr Gln Gln Lys Pro Gly Lys Ala Pro Lys
            20                  25                  30

Leu Leu Ile Tyr Ala Ala Ser Ser Leu Gln Ser Gly Val Pro Ser Arg
        35                  40                  45

Phe Gly Gly Ser Gly Ser Gly Thr Asp Phe Thr Leu Thr Ile Ser Ser
    50                  55                  60

Leu Gln Pro Glu Asp Phe Ala Thr Tyr Tyr Cys Gln His Ser Tyr Thr
65                  70                  75                  80

Ser Phe Gly Gly Gly Thr Lys Val Glu Ile Lys Arg Thr Val Ala Ala
                85                  90                  95

Pro Ser Val Phe Ile Phe Pro Pro Ser Asp Glu Gln Leu Lys Ser Gly
            100                 105                 110

Thr Ala Ser Val Val Cys Leu Leu Asn Asn Phe Tyr Pro Arg Glu Ala
        115                 120                 125

Lys Val Gln Trp Lys Val Asp Asn Ala Leu Gln Ser Gly Asn Ser Gln
    130                 135                 140

Glu Ser Val Thr Glu Gln Asp Ser Lys Asp Ser Thr Tyr Ser Leu Ser
145                 150                 155                 160

Ser Thr Leu Thr Leu Ser Lys Ala Asp Tyr Glu Lys His Lys Val Tyr
                165                 170                 175

Ala Cys Glu Val Thr His Gln Gly Leu Ser Ser Pro Val Thr
            180                 185                 190

<210> SEQ ID NO 29
<211> LENGTH: 198
<212> TYPE: PRT
<213> ORGANISM: artificial sequence
<220> FEATURE:
<223> OTHER INFORMATION: Synthetic construct

<400> SEQUENCE: 29

Pro Gly Ala Thr Val Lys Ile Ser Cys Lys Val Ser Gly Tyr Pro Phe
1               5                   10                  15

Gly Asp Tyr Tyr Leu His Trp Val Gln Gln Ala Pro Gly Lys Gly Leu
            20                  25                  30

Glu Trp Met Gly Leu Val Tyr Pro Glu Asp Gly Glu Thr Ile Leu Ala
        35                  40                  45

Glu Arg Phe Gln Gly Arg Val Thr Ile Thr Ala Asp Ser Ser Thr Asp
    50                  55                  60

Thr Ala Tyr Met Glu Leu Asn Gly Leu Arg Tyr Ala Asp Thr Ala Val
65                  70                  75                  80
```

```
Tyr Tyr Cys Ala Thr Glu Pro Ile Pro Leu Ser Gly Asn Arg Gly Tyr
                85                  90                  95

Phe Asp Tyr Trp Gly Gln Gly Thr Leu Val Thr Val Ser Ser Ala Ser
            100                 105                 110

Thr Lys Gly Pro Ser Val Phe Pro Leu Ala Pro Ser Ser Lys Ser Thr
        115                 120                 125

Ser Gly Gly Thr Ala Ala Leu Gly Cys Leu Val Lys Asp Tyr Phe Pro
    130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
            165                 170                 175

Ser Val Val Thr Val Pro Ser Ser Ser Leu Gly Thr Gln Thr Tyr Ile
            180                 185                 190

Cys Asn Val Asn His Lys
            195

<210> SEQ ID NO 30
<211> LENGTH: 184
<212> TYPE: PRT
<213> ORGANISM: artificial sequence
<220> FEATURE:
<223> OTHER INFORMATION: Synthetic construct

<400> SEQUENCE: 30

Thr Ala Arg Ile Thr Cys Gly Gly Asn Asn Ile Gly Asn Lys Asn Val
1               5                   10                  15

His Trp Tyr Gln Gln Lys Pro Gly Gln Ala Pro Val Leu Val Val Tyr
            20                  25                  30

Asp Asp Ser Asp Arg Pro Ser Gly Ile Pro Glu Arg Phe Ser Gly Ser
        35                  40                  45

Asn Ser Gly Asn Thr Ala Thr Leu Thr Ile Ser Arg Val Glu Ala Gly
    50                  55                  60

Asp Glu Ala Asp Tyr Tyr Cys Gln Leu Trp Asp Asn Ser Asp His
65                  70                  75                  80

Trp Val Phe Gly Gly Gly Thr Lys Leu Thr Val Leu Gly Gln Pro Lys
                85                  90                  95

Ala Ala Pro Ser Val Thr Leu Phe Pro Pro Ser Ser Glu Glu Leu Gln
            100                 105                 110

Ala Asn Lys Ala Thr Leu Val Cys Leu Ile Ser Asp Phe Tyr Pro Gly
        115                 120                 125

Ala Val Thr Val Ala Trp Lys Ala Asp Ser Ser Pro Val Lys Ala Gly
    130                 135                 140

Val Glu Thr Thr Thr Pro Ser Lys Gln Ser Asn Asn Lys Tyr Ala Ala
145                 150                 155                 160

Ser Ser Tyr Leu Ser Leu Thr Pro Glu Gln Trp Lys Ser His Lys Ser
                165                 170                 175

Tyr Ser Cys Gln Val Thr His Glu
            180

<210> SEQ ID NO 31
<211> LENGTH: 216
<212> TYPE: PRT
<213> ORGANISM: artificial sequence
<220> FEATURE:
<223> OTHER INFORMATION: Synthetic construct
```

<400> SEQUENCE: 31

Gly Ala Glu Val Lys Lys Pro Gly Ser Val Lys Val Ser Cys Lys
1               5                   10                  15

Ala Ser Gly Gly Thr Phe Ser Ser Asp Ala Ile Tyr Trp Val Arg Gln
            20                  25                  30

Ala Pro Gly Gln Gly Leu Glu Trp Met Gly Gly Val Ile Pro Ile Phe
        35                  40                  45

Gln Thr Ser Lys Tyr Ala Pro Lys Phe Gln Gly Arg Val Thr Val Thr
    50                  55                  60

Ala Asp Lys Ser Thr Ser Thr Ala Tyr Leu Gln Leu Ser Ser Leu Arg
65                  70                  75                  80

Ser Glu Asp Thr Ala Val Tyr Tyr Cys Ala Arg Gly Gly Pro Val Leu
                85                  90                  95

Gln Ser Asp Asp Phe Trp Asn Gly Tyr Pro Pro Met Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp
    210                 215

<210> SEQ ID NO 32
<211> LENGTH: 111
<212> TYPE: PRT
<213> ORGANISM: artificial sequence
<220> FEATURE:
<223> OTHER INFORMATION: Synthetic construct

<400> SEQUENCE: 32

Gln Ser Pro Ala Thr Leu Ser Val Ser Pro Gly Glu Arg Ala Thr Leu
1               5                   10                  15

Ser Cys Arg Ala Ser Gln Ser Val Ser Ser Asp Leu Ala Trp Tyr Gln
            20                  25                  30

Gln Lys Pro Gly Gln Gly Pro Arg Leu Leu Val Tyr Gly Ala Ser Thr
        35                  40                  45

Arg Ala Thr Ala Ile Pro Ala Arg Tyr Ser Gly Gly Ser Gly Thr
    50                  55                  60

Ala Phe Thr Leu Thr Ile Ser Ser Leu Gln Ser Glu Asp Phe Ala Val
65                  70                  75                  80

Tyr Tyr Cys Gln Gln Tyr His Ile Trp Pro Pro Thr Phe Gly Gln Gly
                85                  90                  95

Thr Lys Val Glu Ile Lys Arg Thr Val Ala Ala Pro Ser Val Phe
            100                 105                 110

<210> SEQ ID NO 33
<211> LENGTH: 204
<212> TYPE: PRT

```
<213> ORGANISM: artificial sequence
<220> FEATURE:
<223> OTHER INFORMATION: Synthetic construct

<400> SEQUENCE: 33

Ala Glu Val Lys Lys Pro Gly Ala Ser Val Lys Val Ser Cys Lys Val
1               5                   10                  15

Ser Gly Tyr Ser Leu Ser Ala Phe Thr Met His Trp Val Arg Gln Ala
            20                  25                  30

Pro Gly Lys Gly Leu Glu Trp Met Gly Gly Phe Asp Pro Glu Asp Gly
        35                  40                  45

Glu Thr Leu Tyr Ala Gln Lys Phe Gln Gly Arg Val Ser Met Thr Glu
    50                  55                  60

Asp Thr Ser Ser Asp Thr Ala Tyr Met Glu Leu Ser Ser Leu Arg Ser
65                  70                  75                  80

Asp Asp Thr Ala Val Tyr Tyr Cys Ala Ser Gly Gly Ile Val Ala
                85                  90                  95

Ala Pro Phe Asp Tyr Trp Gly Gln Gly Thr Leu Val Thr Val Ser Ser
            100                 105                 110

Ala Ser Thr Lys Gly Pro Ser Val Phe Pro Leu Ala Pro Ser Ser Lys
        115                 120                 125

Ser Thr Ser Gly Gly Thr Ala Ala Leu Gly Cys Leu Val Lys Asp Tyr
    130                 135                 140

Phe Pro Glu Pro Val Thr Val Ser Trp Asn Ser Gly Ala Leu Thr Ser
145                 150                 155                 160

Gly Val His Thr Phe Pro Ala Val Leu Gln Ser Ser Gly Leu Tyr Ser
                165                 170                 175

Leu Ser Ser Val Val Thr Val Pro Ser Ser Ser Leu Gly Thr Gln Thr
            180                 185                 190

Tyr Ile Cys Asn Val Asn His Lys Pro Ser Asn Thr
        195                 200

<210> SEQ ID NO 34
<211> LENGTH: 114
<212> TYPE: PRT
<213> ORGANISM: artificial sequence
<220> FEATURE:
<223> OTHER INFORMATION: Synthetic construct

<400> SEQUENCE: 34

Met Ala Glu Ile Val Leu Thr Gln Ser Pro Gly Thr Gln Ser Leu Ser
1               5                   10                  15

Pro Gly Glu Arg Ala Thr Leu Ser Cys Arg Ala Ser Gln Ser Val Gly
            20                  25                  30

Asn Asn Lys Leu Ala Trp Tyr Gln Gln Arg Pro Gly Gln Ala Pro Arg
        35                  40                  45

Leu Leu Ile Tyr Gly Ala Ser Ser Arg Pro Ser Gly Val Ala Asp Arg
    50                  55                  60

Phe Ser Gly Ser Gly Ser Gly Thr Asp Phe Thr Leu Thr Ile Ser Arg
65                  70                  75                  80

Leu Glu Pro Glu Asp Phe Ala Val Tyr Tyr Cys Gln Gln Tyr Gly Gln
                85                  90                  95

Ser Leu Ser Thr Phe Gly Gln Gly Thr Lys Val Glu Val Lys Leu Val
            100                 105                 110

Pro Arg
```

```
<210> SEQ ID NO 35
<211> LENGTH: 137
<212> TYPE: PRT
<213> ORGANISM: artificial sequence
<220> FEATURE:
<223> OTHER INFORMATION: Synthetic construct

<400> SEQUENCE: 35

Gly Ser Gln Val Gln Leu Val Gln Ser Gly Ala Glu Val Lys Arg Pro
1               5                   10                  15

Gly Ser Ser Val Thr Val Ser Cys Lys Ala Ser Gly Gly Ser Phe Ser
            20                  25                  30

Thr Tyr Ala Leu Ser Trp Val Arg Gln Ala Pro Gly Arg Gly Leu Glu
        35                  40                  45

Trp Met Gly Gly Val Ile Pro Leu Leu Thr Ile Thr Asn Tyr Ala Pro
    50                  55                  60

Arg Phe Gln Gly Arg Ile Thr Ile Thr Ala Asp Arg Ser Thr Ser Thr
65                  70                  75                  80

Ala Tyr Leu Glu Leu Asn Ser Leu Arg Pro Glu Asp Thr Ala Val Tyr
                85                  90                  95

Tyr Cys Ala Arg Glu Gly Thr Thr Gly Ala Gly Trp Leu Gly Lys Pro
            100                 105                 110

Ile Gly Ala Phe Ala His Trp Gly Gln Gly Thr Leu Val Thr Val Ser
        115                 120                 125

Ser Leu Glu His His His His His His
    130                 135

<210> SEQ ID NO 36
<211> LENGTH: 214
<212> TYPE: PRT
<213> ORGANISM: artificial sequence
<220> FEATURE:
<223> OTHER INFORMATION: Synthetic construct

<400> SEQUENCE: 36

Ala Leu Gln Leu Thr Gln Ser Pro Ser Ser Leu Ser Ala Ser Val Gly
1               5                   10                  15

Asp Arg Ile Thr Ile Thr Cys Arg Ala Ser Gln Gly Val Thr Ser Ala
            20                  25                  30

Leu Ala Trp Tyr Arg Gln Lys Pro Gly Ser Pro Pro Gln Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Thr Leu Arg Pro
65                  70                  75                  80

Glu Asp Phe Ala Thr Tyr Tyr Cys Gln Gln Leu His Phe Tyr Pro His
                85                  90                  95

Thr Phe Gly Gly Gly Thr Arg Val Asp Val Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Glu Cys Glu Val Thr His Gln Gly Leu Ser Ser Pro Val Thr Lys Ser
        195                 200                 205

Phe Asn Arg Gly Glu Cys
    210

<210> SEQ ID NO 37
<211> LENGTH: 235
<212> TYPE: PRT
<213> ORGANISM: artificial sequence
<220> FEATURE:
<223> OTHER INFORMATION: Synthetic construct

<400> SEQUENCE: 37

Arg Ile Thr Leu Lys Glu Ser Gly Pro Pro Leu Val Lys Pro Thr Gln
1               5                   10                  15

Thr Leu Thr Leu Thr Cys Ser Phe Ser Gly Phe Ser Leu Ser Asp Phe
            20                  25                  30

Gly Val Gly Val Gly Trp Ile Arg Gln Pro Pro Gly Lys Ala Leu Glu
        35                  40                  45

Trp Leu Ala Ile Ile Tyr Ser Asp Asp Lys Arg Tyr Ser Pro Ser
    50                  55                  60

Leu Asn Thr Arg Leu Thr Ile Thr Lys Asp Thr Ser Lys Asn Gln Val
65                  70                  75                  80

Val Leu Val Met Thr Arg Val Ser Pro Val Asp Thr Ala Thr Tyr Phe
                85                  90                  95

Cys Ala His Arg Arg Gly Pro Thr Thr Leu Phe Gly Val Pro Ile Ala
            100                 105                 110

Arg Gly Pro Val Asn Ala Met Asp Val Trp Gly Gln Gly Ile Thr Val
        115                 120                 125

Thr Ile Ser Ser Thr Ser Thr Lys Gly Pro Ser Val Phe Pro Leu Ala
130                 135                 140

Pro Ser Ser Lys Ser Thr Ala Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
        195                 200                 205

Gly Thr Gln Thr Tyr Thr Cys Asn Val Asn His Lys Pro Ser Asn Thr
    210                 215                 220

Lys Val Asp Lys Arg Val Glu Pro Lys Ser Cys
225                 230                 235

<210> SEQ ID NO 38
<211> LENGTH: 225
<212> TYPE: PRT
<213> ORGANISM: artificial sequence
<220> FEATURE:
<223> OTHER INFORMATION: Synthetic construct

<400> SEQUENCE: 38

Glu Val Gln Leu Val Glu Ser Gly Gly Gly Leu Val Lys Ala Gly Gly
1               5                   10                  15

Ser Leu Ile Leu Ser Cys Gly Val Ser Asn Phe Arg Ile Ser Ala His
            20                  25                  30
```

```
Thr Met Asn Trp Val Arg Arg Val Pro Gly Gly Gly Leu Glu Trp Val
         35                  40                  45

Ala Ser Ile Ser Thr Ser Ser Thr Tyr Arg Asp Tyr Ala Asp Ala Val
 50                  55                  60

Lys Gly Arg Phe Thr Val Ser Arg Asp Asp Leu Glu Asp Phe Val Tyr
 65                  70                  75                  80

Leu Gln Met His Lys Met Arg Val Glu Asp Thr Ala Ile Tyr Tyr Cys
                 85                  90                  95

Ala Arg Lys Gly Ser Asp Arg Leu Ser Asp Asn Asp Pro Phe Asp Ala
                100                 105                 110

Trp Gly Pro Gly Thr Val Val Thr Val Ser Pro Ala Ser Thr Lys Gly
                115                 120                 125

Pro Ser Val Phe Pro Leu Ala Pro Ser Ser Lys Ser Thr Ser Gly Gly
                130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser
225

<210> SEQ ID NO 39
<211> LENGTH: 212
<212> TYPE: PRT
<213> ORGANISM: artificial sequence
<220> FEATURE:
<223> OTHER INFORMATION: Synthetic construct

<400> SEQUENCE: 39

Val Val Met Thr Gln Ser Pro Ser Thr Leu Ser Ala Ser Val Gly Asp
  1               5                  10                  15

Thr Ile Thr Ile Thr Cys Arg Ala Ser Gln Ser Ile Glu Thr Trp Leu
                 20                  25                  30

Ala Trp Tyr Gln Gln Lys Pro Gly Lys Ala Pro Lys Leu Leu Ile Tyr
             35                  40                  45

Lys Ala Ser Thr Leu Lys Thr Gly Val Pro Ser Arg Phe Ser Gly Ser
 50                  55                  60

Gly Ser Gly Thr Glu Phe Thr Leu Thr Ile Ser Gly Leu Gln Phe Asp
 65                  70                  75                  80

Asp Phe Ala Thr Tyr His Cys Gln His Tyr Ala Gly Tyr Ser Ala Thr
                 85                  90                  95

Phe Gly Gln Gly Thr Arg Val Glu Ile Lys Arg Thr Val Ala Ala Pro
                100                 105                 110

Ser Val Phe Ile Phe Pro Pro Ser Asp Glu Gln Leu Lys Ser Gly Thr
                115                 120                 125

Ala Ser Val Val Cys Leu Leu Asn Asn Phe Tyr Pro Arg Glu Ala Lys
                130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu
        210

<210> SEQ ID NO 40
<211> LENGTH: 212
<212> TYPE: PRT
<213> ORGANISM: artificial sequence
<220> FEATURE:
<223> OTHER INFORMATION: Synthetic construct

<400> SEQUENCE: 40

Val Val Met Thr Gln Ser Pro Ser Thr Leu Ser Ala Ser Val Gly Asp
1               5                  10                  15

Thr Ile Thr Ile Thr Cys Arg Ala Ser Gln Ser Ile Glu Thr Trp Leu
            20                  25                  30

Ala Trp Tyr Gln Gln Lys Pro Gly Lys Ala Pro Lys Leu Leu Ile Tyr
        35                  40                  45

Lys Ala Ser Thr Leu Lys Thr Gly Val Pro Ser Arg Phe Ser Gly Ser
 50                 55                  60

Gly Ser Gly Thr Glu Phe Thr Leu Thr Ile Ser Gly Leu Gln Phe Asp
65                  70                  75                  80

Asp Phe Ala Thr Tyr His Cys Gln His Tyr Ala Gly Tyr Ser Ala Thr
                85                  90                  95

Phe Gly Gln Gly Thr Arg Val Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu
        210

<210> SEQ ID NO 41
<211> LENGTH: 156
<212> TYPE: PRT
<213> ORGANISM: artificial sequence
<220> FEATURE:
<223> OTHER INFORMATION: Synthetic construct

<400> SEQUENCE: 41

Leu Tyr Leu Glu Met Asn Asn Leu Arg Met Glu Asp Ser Gly Leu Tyr
1               5                  10                  15

Phe Cys Ala Arg Thr Gly Lys Tyr Tyr Asp Phe Trp Ser Gly Tyr Pro
```

```
                    20                  25                  30
Pro Gly Glu Glu Tyr Phe Gln Asp Trp Gly Arg Gly Thr Leu Val Thr
                35                  40                  45
Val Ser Ser Ala Ser Thr Lys Gly Pro Ser Val Phe Pro Leu Ala Pro
            50                  55                  60
Ser Ser Lys Ser Thr Ser Gly Gly Thr Ala Ala Leu Gly Cys Leu Val
65                  70                  75                  80
Lys Asp Tyr Phe Pro Glu Pro Val Thr Val Ser Trp Asn Ser Gly Ala
                85                  90                  95
Leu Thr Ser Gly Val His Thr Phe Pro Ala Val Leu Gln Ser Ser Gly
                100                 105                 110
Leu Tyr Ser Leu Ser Ser Val Val Thr Val Pro Ser Ser Ser Leu Gly
            115                 120                 125
Thr Gln Thr Tyr Ile Cys Asn Val Asn His Lys Pro Ser Asn Thr Lys
        130                 135                 140
Val Asp Lys Arg Val Glu Pro Lys Ser Cys Asp Lys
145                 150                 155

<210> SEQ ID NO 42
<211> LENGTH: 212
<212> TYPE: PRT
<213> ORGANISM: artificial sequence
<220> FEATURE:
<223> OTHER INFORMATION: Synthetic construct

<400> SEQUENCE: 42

Glu Leu Thr Gln Ser Pro Ala Thr Leu Ser Leu Ser Pro Gly Glu Arg
1               5                   10                  15
Ala Thr Leu Ser Cys Arg Ala Ser Gln Ser Val Gly Arg Asn Leu Gly
                20                  25                  30
Trp Tyr Gln Gln Lys Pro Gly Gln Ala Pro Arg Leu Leu Ile Tyr Asp
                35                  40                  45
Ala Ser Asn Arg Ala Thr Gly Ile Pro Ala Arg Phe Ser Gly Ser Gly
            50                  55                  60
Ser Gly Thr Asp Phe Thr Leu Thr Ile Ser Ser Leu Glu Pro Glu Asp
65                  70                  75                  80
Phe Ala Val Tyr Tyr Cys Gln Ala Arg Leu Leu Leu Pro Gln Thr Phe
                85                  90                  95
Gly Gln Gly Thr Lys Val Glu Ile Lys Arg Thr Val Ala Ala Pro Ser
                100                 105                 110
Val Phe Ile Phe Pro Pro Ser Asp Glu Gln Leu Lys Ser Gly Thr Ala
            115                 120                 125
Ser Val Val Cys Leu Leu Asn Asn Phe Tyr Pro Arg Glu Ala Lys Val
        130                 135                 140
Gln Trp Lys Val Asp Asn Ala Leu Gln Ser Gly Asn Ser Gln Glu Ser
145                 150                 155                 160
Val Thr Glu Gln Asp Ser Lys Asp Ser Thr Tyr Ser Leu Ser Ser Thr
                165                 170                 175
Leu Thr Leu Ser Lys Ala Asp Tyr Glu Lys His Lys Val Tyr Ala Cys
                180                 185                 190
Glu Val Thr His Gln Gly Leu Ser Ser Pro Val Thr Lys Ser Phe Asn
            195                 200                 205
Arg Gly Glu Cys
210
```

```
<210> SEQ ID NO 43
<211> LENGTH: 231
<212> TYPE: PRT
<213> ORGANISM: artificial sequence
<220> FEATURE:
<223> OTHER INFORMATION: Synthetic construct

<400> SEQUENCE: 43
```

Ser Glu Val Gln Leu Leu Glu Ser Gly Pro Gly Leu Leu Lys Pro Ser
1               5                   10                  15

Glu Thr Leu Ser Leu Thr Cys Thr Val Ser Gly Gly Ser Met Ile Asn
            20                  25                  30

Tyr Tyr Trp Ser Trp Ile Arg Gln Pro Pro Gly Glu Arg Pro Gln Trp
        35                  40                  45

Leu Gly His Ile Ile Tyr Gly Gly Thr Thr Lys Tyr Asn Pro Ser Leu
    50                  55                  60

Glu Ser Arg Ile Thr Ile Ser Arg Asp Ile Ser Lys Asn Gln Phe Ser
65                  70                  75                  80

Leu Arg Leu Asn Ser Val Thr Ala Ala Asp Thr Ala Ile Tyr Tyr Cys
                85                  90                  95

Ala Arg Val Ala Ile Gly Val Ser Gly Phe Leu Asn Tyr Tyr Tyr Tyr
            100                 105                 110

Met Asp Val Trp Gly Ser Gly Thr Ala Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys
225                 230

```
<210> SEQ ID NO 44
<211> LENGTH: 215
<212> TYPE: PRT
<213> ORGANISM: artificial sequence
<220> FEATURE:
<223> OTHER INFORMATION: Synthetic construct

<400> SEQUENCE: 44
```

Glu Leu Val Leu Thr Gln Ser Pro Gly Thr Leu Ser Leu Ser Ala Gly
1               5                   10                  15

Glu Arg Ala Thr Leu Ser Cys Arg Ala Ser Gln Ser Val Ser Ser Gly
            20                  25                  30

Ser Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Gly Arg Leu Glu
65                  70                  75                  80

```
Pro Glu Asp Leu Ala Val Tyr Tyr Cys Gln Gln Tyr Gly Thr Ser Pro
                85                  90                  95

Tyr Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Arg Asp Ser Thr Tyr Ser Leu
                165                 170                 175

Gly Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
            210             215

<210> SEQ ID NO 45
<211> LENGTH: 239
<212> TYPE: PRT
<213> ORGANISM: artificial sequence
<220> FEATURE:
<223> OTHER INFORMATION: Synthetic construct

<400> SEQUENCE: 45

Glu Val Gln Leu Leu Glu Gln Ser Gly Ala Glu Val Lys Lys Pro Gly
1               5                   10                  15

Ser Ser Val Gln Val Ser Cys Lys Ala Ser Gly Gly Thr Phe Ser Met
            20                  25                  30

Tyr Gly Phe Asn Trp Val Arg Gln Ala Pro Gly His Gly Leu Glu Trp
        35                  40                  45

Met Gly Gly Ile Ile Pro Ile Phe Gly Thr Ser Asn Tyr Ala Gln Lys
    50                  55                  60

Phe Arg Gly Arg Val Thr Phe Thr Ala Asp Gln Ala Ser Thr Ala
65                  70                  75                  80

Tyr Met Glu Leu Thr Asn Leu Arg Ser Asp Asp Thr Ala Val Tyr Tyr
                85                  90                  95

Cys Ala Arg Asp Phe Gly Pro Asp Trp Glu Asp Gly Asp Ser Tyr Asp
            100                 105                 110

Gly Ser Gly Arg Gly Phe Phe Asp Phe Trp Gly Gln Gly Thr Leu Val
            115                 120                 125

Thr Val Ser Ser Ala Ser Thr Lys Gly Pro Ser Val Phe Pro Leu Ala
            130                 135                 140

Pro Ser Ser Lys Ser Thr Ser Gly Gly Thr Ala Ala Leu Gly Cys Leu
145                 150                 155                 160

Val Lys Asp Tyr Phe Pro Glu Pro Val Thr Val Ser Trp Asn Ser Gly
                165                 170                 175

Ala Leu Thr Ser Gly Val His Thr Phe Pro Ala Val Leu Gln Ser Ser
            180                 185                 190

Gly Leu Tyr Ser Leu Ser Ser Val Val Thr Val Pro Ser Ser Ser Leu
            195                 200                 205

Gly Thr Gln Thr Tyr Ile Cys Asn Val Asn His Lys Pro Ser Asn Thr
            210                 215                 220
```

Lys Val Asp Lys Lys Val Glu Pro Lys Ser Cys Asp Lys Thr Ser
225                 230                 235

<210> SEQ ID NO 46
<211> LENGTH: 1140
<212> TYPE: DNA
<213> ORGANISM: artificial sequence
<220> FEATURE:
<223> OTHER INFORMATION: Synthetic construct

<400> SEQUENCE: 46

```
atggttcggg gggtgccctt ccgacatctg ctgctggtcc tgcagctggc tctgctgcct      60
gccgctactc aggggaaaaa agtcgtgctg gggaagaaag cgacacagt ggagctgacc      120
tgcacagctt ctcagaagaa aagtatccag ttccactgga agaactctaa tcagatcaaa     180
attctgggaa accagggcag ctttctgact aagggcccat ccaaactgaa tgaccgcgca     240
gatagtcgga gatcactgtg ggatcagggg aacttccccc tgatcattaa gaatctgaaa     300
atcgaagaca gtgatacata catttgtgag gtggaagacc agaaggagga agtgcagctg     360
ctggtctttg gactgacagc caactccgat actcatctgc tgcagggcca gtctctgact     420
ctgaccctgg agagtccacc tggaagctcc ccatcagtgc agtgcaggag ccctcgagga     480
aagaacatcc agggcgggaa accctgtca gtcagccagc tggaactgca ggactccggg      540
acatggactt gtaccgtgct gcagaatcag aagaaagtcg agttcaagat cgatattgtg     600
gtcctggctt ttcagaaagc ttccggaggc gggggatcta tctaccagga gctgactcag    660
ctgaaggccg ctgtggaaag actgtgccac ccatgtccct gggagtggac cttctttcag    720
ggaaactgct atttcatgtc caactctcag aggaattggc atgactccat caccgcctgt   780
aaggaagtgg cgctcagct ggtggtcatc aagtctgctg aggaacagaa cttcctgcag     840
ctgcagtcta gtcgatcaaa tcggtttacc tggatgggcc tgagcgacct gaaccaggag    900
ggcacatggc agtgggtgga tgggagtcct ctgctgcctt cattcaagca gtattggaat   960
cgaggggaac taacaatgt cggagaggaa gattgcgcag agttcagcgg caacgggtgg    1020
aatgacgata gtgtaatct ggccaaattt tggatctgca agaaaagcgc agcctcctgt    1080
agtcgggacg aggagcagtt tctgagccca gcaccagcaa cacccaaccc accaccagcc   1140
```

<210> SEQ ID NO 47
<211> LENGTH: 380
<212> TYPE: PRT
<213> ORGANISM: artificial sequence
<220> FEATURE:
<223> OTHER INFORMATION: Synthetic construct

<400> SEQUENCE: 47

Met Val Arg Gly Val Pro Phe Arg His Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

| | | | | | | | | | | | |
|---|---|---|---|---|---|---|---|---|---|---|---|
|Lys|Asn|Leu|Lys|Ile|Glu|Asp|Ser|Asp|Thr|Tyr|Ile|Cys|Glu|Val|Glu|
| | | |100| | | |105| | | |110| | | | |

```
Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
            115                 120                 125

Ser Asp Thr His Leu Leu Gln Gly Gln Ser Leu Thr Leu Thr Leu Glu
        130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Gly Gly Gly Gly Ser Ile Tyr Gln Glu Leu Thr Gln Leu Lys Ala Ala
    210                 215                 220

Val Glu Arg Leu Cys His Pro Cys Pro Trp Glu Trp Thr Phe Phe Gln
225                 230                 235                 240

Gly Asn Cys Tyr Phe Met Ser Asn Ser Gln Arg Asn Trp His Asp Ser
                245                 250                 255

Ile Thr Ala Cys Lys Glu Val Gly Ala Gln Leu Val Val Ile Lys Ser
            260                 265                 270

Ala Glu Glu Gln Asn Phe Leu Gln Leu Gln Ser Ser Arg Ser Asn Arg
        275                 280                 285

Phe Thr Trp Met Gly Leu Ser Asp Leu Asn Gln Glu Gly Thr Trp Gln
    290                 295                 300

Trp Val Asp Gly Ser Pro Leu Leu Pro Ser Phe Lys Gln Tyr Trp Asn
305                 310                 315                 320

Arg Gly Glu Pro Asn Asn Val Gly Glu Glu Asp Cys Ala Glu Phe Ser
                325                 330                 335

Gly Asn Gly Trp Asn Asp Asp Lys Cys Asn Leu Ala Lys Phe Trp Ile
            340                 345                 350

Cys Lys Lys Ser Ala Ala Ser Cys Ser Arg Asp Glu Glu Gln Phe Leu
        355                 360                 365

Ser Pro Ala Pro Ala Thr Pro Asn Pro Pro Ala
    370                 375                 380
```

<210> SEQ ID NO 48
<211> LENGTH: 1086
<212> TYPE: DNA
<213> ORGANISM: artificial sequence
<220> FEATURE:
<223> OTHER INFORMATION: Synthetic construct

<400> SEQUENCE: 48

```
atggttcggg gggtgccctt ccgacatctg ctgctggtcc tgcagctggc tctgctgcct    60
gccgctactc agggaaaaaa agtcgtgctg gggaagaaag cgacacagt ggagctgacc    120 tgcacagctt ctcagaagaa agtatccag ttccactgga agaactctaa tcagatcaaa    180
attctgggaa accagggcag ctttctgact aagggcccat ccaaactgaa tgaccgcgca    240
gatagtcgga gatcactgtg gatcagggg aacttccccc tgatcattaa gaatctgaaa    300
atcgaagaca gtgatacata catttgtgag gtggaagacc agaaggagga agtgcagctg    360
ctggtctttg gactgacagc caactccgat actcatctgc tgcagggcca gtctctgact    420
ctgaccctgg agagtccacc tggaagctcc ccatcagtgc agtgcaggag ccctcgagga    480
```

-continued

```
aagaacatcc agggcgggaa aaccctgtca gtcagccagc tggaactgca ggactccggg    540
acatggactt gtaccgtgct gcagaatcag aagaaagtcg agttcaagat cgatattgtg    600
gtcctggctt ttcagaaagc ttccggaggc gggggatcta tctaccagga gctgaccgac    660
ctgaagaccg ccttcgagag gctgtgcagg cactgcccca aggactggac cttcttccag    720
ggcaactgct acttcatgag caacagccag aggaactggc acgacagcgt gaccgcctgc    780
cagggagtga gggcccagct ggtggtcatc aagaccgccg aggagcagaa cttcctgcag    840
ctgcagacca gcaggagcaa caggttcagc tggatgggcc tgagcgacct gaaccaggag    900
ggcacctggc agtgggtgga cggcagcccc ctgagcccca gcttccagag gtactggaac    960
agcggcgagc ccaacaacag cggcaacgag gactgcgccg agttcagcgg cagcggctgg   1020
aacgacaaca ggtgcgacgt ggacaactac tggatctgca agaagcccgc cgcctgcttc   1080
agggac                                                              1086
```

<210> SEQ ID NO 49
<211> LENGTH: 362
<212> TYPE: PRT
<213> ORGANISM: artificial sequence
<220> FEATURE:
<223> OTHER INFORMATION: Synthetic construct

<400> SEQUENCE: 49

```
Met Val Arg Gly Val Pro Phe Arg His Leu Leu Val Leu Gln Leu
1               5                   10                  15

Ala Leu Leu Pro Ala Ala Thr Gln Gly Lys Lys Val Val Leu Gly Lys
            20                  25                  30

Lys Gly Asp Thr Val Glu Leu Thr Cys Thr Ala Ser Gln Lys Lys Ser
        35                  40                  45

Ile Gln Phe His Trp Lys Asn Ser Asn Gln Ile Lys Ile Leu Gly Asn
    50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190

Val Glu Phe Lys Ile Asp Ile Val Val Leu Ala Phe Gln Lys Ala Ser
        195                 200                 205

Gly Gly Gly Gly Ser Ile Tyr Gln Glu Leu Thr Asp Leu Lys Thr Ala
    210                 215                 220

Phe Glu Arg Leu Cys Arg His Cys Pro Lys Asp Trp Thr Phe Phe Gln
225                 230                 235                 240

Gly Asn Cys Tyr Phe Met Ser Asn Ser Gln Arg Asn Trp His Asp Ser
```

```
                    245                 250                 255
Val Thr Ala Cys Gln Glu Val Arg Ala Gln Leu Val Val Ile Lys Thr
                260                 265                 270
Ala Glu Glu Gln Asn Phe Leu Gln Leu Gln Thr Ser Arg Ser Asn Arg
            275                 280                 285
Phe Ser Trp Met Gly Leu Ser Asp Leu Asn Gln Glu Gly Thr Trp Gln
        290                 295                 300
Trp Val Asp Gly Ser Pro Leu Ser Pro Ser Phe Gln Arg Tyr Trp Asn
305                 310                 315                 320
Ser Gly Glu Pro Asn Asn Ser Gly Asn Glu Asp Cys Ala Glu Phe Ser
                325                 330                 335
Gly Ser Gly Trp Asn Asp Asn Arg Cys Asp Val Asp Asn Tyr Trp Ile
            340                 345                 350
Cys Lys Lys Pro Ala Ala Cys Phe Arg Asp
        355                 360

<210> SEQ ID NO 50
<211> LENGTH: 1062
<212> TYPE: DNA
<213> ORGANISM: artificial sequence
<220> FEATURE:
<223> OTHER INFORMATION: Synthetic construct

<400> SEQUENCE: 50
atggttcggg gggtgccctt ccgacatctg ctgctggtcc tgcagctggc tctgctgcct      60
gccgctactc aggggaaaaa agtcgtgctg gggaagaaag cgacacagt ggagctgacc     120 tgcacagctt ctcagaagaa aagtatccag ttccactgga agaactctaa tcagatcaaa     180
attctgggaa accagggcag ctttctgact aagggcccat ccaaactgaa tgaccgcgca     240
gatagtcgga gatcactgtg ggatcagggg aacttccccc tgatcattaa gaatctgaaa     300
atcgaagaca gtgatacata catttgtgag gtggaagacc agaaggagga agtgcagctg     360
ctggtctttg gactgacagc caactccgat actcatctgc tgcagggcca gtctctgact     420
ctgaccctgg agagtccacc tggaagctcc ccatcagtgc agtgcaggag ccctcgagga     480
aagaacatcc agggcgggaa aaccctgtca gtcagccagc tggaactgca ggactccggg     540
acatggactt gtaccgtgct gcagaatcag aagaaagtcg agttcaagat cgatattgtg     600
gtcctggctt ttcagaaagc ttccggaggc ggggatctc agaatgatat cctgcaggtg     660
gtgagccagg gctggaagta cttcaaaggg aatttctact attttttccct gattcctaag     720 acatggtatt ctgccgagca gttctgcgtg tcaaggaaca gccacctgac ctccgtgaca     780
tctgagagtg aacaggagtt tctgtacaag accgccggcg gactgatcta ttggattggg     840
ctgacaaaag ctggaatgga gggcgactgg agttgggtgg acgataccc attcaataag     900 gtgcagtcag tgcggttttg gatccccgga gaacctaaca atgccggcaa caatgagcat     960
tgcgggaaca tcaaggctcc tagcctgcag gcctggaatg acgctccatg cgataagaca    1020
ttcctgttta tctgtaaaag gccatatgtg ccctccgaac ct                       1062

<210> SEQ ID NO 51
<211> LENGTH: 354
<212> TYPE: PRT
<213> ORGANISM: artificial sequence
<220> FEATURE:
<223> OTHER INFORMATION: Synthetic construct

<400> SEQUENCE: 51
```

```
Met Val Arg Gly Val Pro Phe Arg His Leu Leu Val Leu Gln Leu
1               5                   10                  15

Ala Leu Leu Pro Ala Ala Thr Gln Gly Lys Lys Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
50                  55                      60

Gln Gly Ser Phe Leu Thr Lys Gly Pro Ser Lys Leu Asn Asp Arg Ala
65                      70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
                100                 105                 110

Asp Gln Lys Glu Glu Val Gln Leu Leu Val Phe Gly Leu Thr Ala Asn
                115                 120                 125

Ser Asp Thr His Leu Leu Gln Gly Gln Ser Leu Thr Leu Thr Leu Glu
                130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
                180                 185                 190

Val Glu Phe Lys Ile Asp Ile Val Val Leu Ala Phe Gln Lys Ala Ser
                195                 200                 205

Gly Gly Gly Gly Ser Gln Asn Asp Ile Leu Gln Val Val Ser Gln Gly
                210                 215                 220

Trp Lys Tyr Phe Lys Gly Asn Phe Tyr Tyr Phe Ser Leu Ile Pro Lys
225                 230                 235                 240

Thr Trp Tyr Ser Ala Glu Gln Phe Cys Val Ser Arg Asn Ser His Leu
                245                 250                 255

Thr Ser Val Thr Ser Glu Ser Glu Gln Glu Phe Leu Tyr Lys Thr Ala
                260                 265                 270

Gly Gly Leu Ile Tyr Trp Ile Gly Leu Thr Lys Ala Gly Met Glu Gly
                275                 280                 285

Asp Trp Ser Trp Val Asp Asp Thr Pro Phe Asn Lys Val Gln Ser Val
290                 295                 300

Arg Phe Trp Ile Pro Gly Glu Pro Asn Asn Ala Gly Asn Asn Glu His
305                 310                 315                 320

Cys Gly Asn Ile Lys Ala Pro Ser Leu Gln Ala Trp Asn Asp Ala Pro
                325                 330                 335

Cys Asp Lys Thr Phe Leu Phe Ile Cys Lys Arg Pro Tyr Val Pro Ser
                340                 345                 350

Glu Pro

<210> SEQ ID NO 52
<211> LENGTH: 990
<212> TYPE: DNA
<213> ORGANISM: artificial sequence
<220> FEATURE:
<223> OTHER INFORMATION: Synthetic construct

<400> SEQUENCE: 52
atggttcggg gggtgccctt ccgacatctg ctgctggtcc tgcagctggc tctgctgcct    60
```

```
gccgctactc agggggaaaaa agtcgtgctg gggaagaaag cgacacagt ggagctgacc    120 tgcacagctt ctcagaagaa aagtatccag ttccactgga agaactctaa tcagatcaaa    180
attctgggaa accagggcag ctttctgact aagggcccat ccaaactgaa tgaccgcgca    240
gatagtcgga gatcactgtg ggatcagggg aacttccccc tgatcattaa gaatctgaaa    300
atcgaagaca gtgatacata catttgtgag gtggaagacc agaaggagga agtgcagctg    360
ctggtctttg gactgacagc caactccgat actcatctgc tgcagggcca gtctctgact    420
ctgaccctgg agagtccacc tggaagctcc ccatcagtgc agtgcaggag ccctcgagga    480
aagaacatcc agggcgggaa aaccctgtca gtcagccagc tggaactgca ggactccggg    540
acatggactt gtaccgtgct gcagaatcag aagaaagtcg agttcaagat cgatattgtg    600
gtcctggctt tcagaaagc ttccggaggc gggggatcta agcaagtggg aaacaaattc    660
tttctgacca atggcgagat tatgacattc gaaaaggtga agctctgtg cgtcaagttt    720 caggcctccg tggctacccc tcgaaacgca gccgagaatg gggctatcca gaacctgatt    780
aaggaggaag cattcctggg catcacagac gagaaaactg aaggccagtt tgtggatctg    840
acaggaaata ggctgactta caccaactgg aatgagggg aaccaaacaa tgccggttcc    900
gacgaggatt gcgtgctgct gctgaagaac ggccagtgga atgacgtgcc ctgcagcacc    960
tctcacctgg ctgtctgtga gttccctatt                                     990
```

```
<210> SEQ ID NO 53
<211> LENGTH: 330
<212> TYPE: PRT
<213> ORGANISM: artificial sequence
<220> FEATURE:
<223> OTHER INFORMATION: Synthetic construct

<400> SEQUENCE: 53

Met Val Arg Gly Val Pro Phe Arg His Leu Leu Val Leu Gln Leu
1               5                   10                  15

Ala Leu Leu Pro Ala Ala Thr Gln Gly Lys Lys Val Val Leu Gly Lys
                20                  25                  30

Lys Gly Asp Thr Val Glu Leu Thr Cys Thr Ala Ser Gln Lys Lys Ser
            35                  40                  45

Ile Gln Phe His Trp Lys Asn Ser Asn Gln Ile Lys Ile Leu Gly Asn
        50                  55                  60

Gln Gly Ser Phe Leu Thr Lys Gly Pro Ser Lys Leu Asn Asp Arg Ala
65                  70                  75                  80

Asp Ser Arg Arg Ser Leu Trp Asp Gln Gly Asn Phe Pro Leu Ile Ile
                85                  90                  95

Lys Asn Leu Lys Ile Glu Asp Ser Asp Thr Tyr Ile Cys Glu Val Glu
            100                 105                 110

Asp Gln Lys Glu Glu Val Gln Leu Leu Val Phe Gly Leu Thr Ala Asn
        115                 120                 125

Ser Asp Thr His Leu Leu Gln Gly Gln Ser Leu Thr Leu Thr Leu Glu
    130                 135                 140

Ser Pro Pro Gly Ser Ser Pro Ser Val Gln Cys Arg Ser Pro Arg Gly
145                 150                 155                 160

Lys Asn Ile Gln Gly Gly Lys Thr Leu Ser Val Ser Gln Leu Glu Leu
                165                 170                 175

Gln Asp Ser Gly Thr Trp Thr Cys Thr Val Leu Gln Asn Gln Lys Lys
            180                 185                 190
```

```
Val Glu Phe Lys Ile Asp Ile Val Leu Ala Phe Gln Lys Ala Ser
    195                 200                 205
Gly Gly Gly Ser Lys Gln Val Gly Asn Lys Phe Leu Thr Asn
210                 215                 220
Gly Glu Ile Met Thr Phe Glu Lys Val Lys Ala Leu Cys Val Lys Phe
225                 230                 235                 240
Gln Ala Ser Val Ala Thr Pro Arg Asn Ala Glu Asn Gly Ala Ile
                245                 250                 255
Gln Asn Leu Ile Lys Glu Glu Ala Phe Leu Gly Ile Thr Asp Glu Lys
                260                 265                 270
Thr Glu Gly Gln Phe Val Asp Leu Thr Gly Asn Arg Leu Thr Tyr Thr
            275                 280                 285
Asn Trp Asn Glu Gly Glu Pro Asn Asn Ala Gly Ser Asp Glu Asp Cys
        290                 295                 300
Val Leu Leu Leu Lys Asn Gly Gln Trp Asn Asp Val Pro Cys Ser Thr
305                 310                 315                 320
Ser His Leu Ala Val Cys Glu Phe Pro Ile
                325                 330

<210> SEQ ID NO 54
<211> LENGTH: 69
<212> TYPE: PRT
<213> ORGANISM: Homo sapiens

<400> SEQUENCE: 54

Thr Thr Thr Pro Ala Pro Arg Pro Pro Thr Pro Ala Pro Thr Ile Ala
1               5                   10                  15
Ser Gln Pro Leu Ser Leu Arg Pro Glu Ala Cys Arg Pro Ala Ala Gly
                20                  25                  30
Gly Ala Val His Thr Arg Gly Leu Asp Phe Ala Cys Asp Ile Tyr Ile
            35                  40                  45
Trp Ala Pro Leu Ala Gly Thr Cys Gly Val Leu Leu Leu Ser Leu Val
        50                  55                  60
Ile Thr Leu Tyr Cys
65

<210> SEQ ID NO 55
<211> LENGTH: 67
<212> TYPE: PRT
<213> ORGANISM: Homo sapiens

<400> SEQUENCE: 55

Ile Glu Val Met Tyr Pro Pro Pro Tyr Leu Asp Asn Glu Lys Ser Asn
1               5                   10                  15
Gly Thr Ile Ile His Val Lys Gly Lys His Leu Cys Pro Ser Pro Leu
                20                  25                  30
Phe Pro Gly Pro Ser Lys Pro Phe Trp Val Leu Val Val Val Gly Gly
            35                  40                  45
Val Leu Ala Cys Tyr Ser Leu Leu Val Thr Val Ala Phe Ile Ile Phe
        50                  55                  60
Trp Val Arg
65

<210> SEQ ID NO 56
<211> LENGTH: 112
<212> TYPE: PRT
<213> ORGANISM: Homo sapiens
```

```
<400> SEQUENCE: 56

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
                100                 105                 110

<210> SEQ ID NO 57
<211> LENGTH: 84
<212> TYPE: PRT
<213> ORGANISM: Homo sapiens

<400> SEQUENCE: 57

Phe Val Pro Val Phe Leu Pro Ala Lys Pro Thr Thr Thr Pro Ala Pro
1               5                   10                  15

Arg Pro Pro Thr Pro Ala Pro Thr Ile Ala Ser Gln Pro Leu Ser Leu
            20                  25                  30

Arg Pro Glu Ala Cys Arg Pro Ala Ala Gly Gly Ala Val His Thr Arg
        35                  40                  45

Gly Leu Asp Phe Ala Cys Asp Ile Tyr Ile Trp Ala Pro Leu Ala Gly
    50                  55                  60

Thr Cys Gly Val Leu Leu Leu Ser Leu Val Ile Thr Leu Tyr Cys Asn
65                  70                  75                  80

His Arg Asn Arg

<210> SEQ ID NO 58
<211> LENGTH: 40
<212> TYPE: PRT
<213> ORGANISM: Homo sapiens

<400> SEQUENCE: 58

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
        35                  40

<210> SEQ ID NO 59
<211> LENGTH: 47
<212> TYPE: PRT
<213> ORGANISM: Homo sapiens

<400> SEQUENCE: 59

Arg Phe Ser Val Val Lys Arg Gly Arg Lys Lys Leu Leu Tyr Ile Phe
1               5                   10                  15

Lys Gln Pro Phe Met Arg Pro Val Gln Thr Thr Gln Glu Glu Asp Gly
            20                  25                  30
```

```
Cys Ser Cys Arg Phe Pro Glu Glu Glu Gly Gly Cys Glu Leu
    35                  40                  45
```

CHIMERIC ANTIGEN RECEPTORS TO CONTROL HIV INFECTION

CROSS REFERENCE TO RELATED APPLICATIONS

This is the U.S. National Stage of International Application No. PCT/US2014/067459, filed Nov. 25, 2014, which was published in English under PCT Article 21(2), which in turn claims the benefit of U.S. Provisional Application Nos. 62/040,398, filed Aug. 21, 2014, and 61/908,691, filed Nov. 25, 2013. Each of the provisional applications is incorporated by reference herein in its entirety.

FIELD

This disclosure relates to proteins useful in the treatment of human immunodeficiency virus (HIV) infection. More specifically, it relates to chimeric antigen receptor fusion proteins that include a multispecific targeting segment linked to a transmembrane domain and intracellular domains involved in $CD8^+$ T cell signaling. This disclosure also relates to genetically engineered immune cells.

BACKGROUND $CD8^+$ cytotoxic T lymphocytes (CTL) are immunologic effector cells that have the capacity to specifically recognize and directly kill specific target cells, via interaction of the T cell receptor (TCR) on the CTL surface with peptide/HLA Class 1 complexes on the target cell surface. Beyond relying on naturally elicited CTL, gene transfer of cDNA constructs encoding engineered antigen receptors is an alternate strategy for generating CTL that can be adoptively transferred back to the patient for highly specific therapy. A particularly effective engineered antigen receptor is known as a chimeric antigen receptor (CAR) which directly binds native antigen on the target cell surface and transduces activation signals via immunoreceptor tyrosine-based activation motifs present in the cytoplasmic tails. CAR constructs utilizing an antigen-binding moiety generated from single chain antibodies (scFv) afford the major advantage of being "universal" in that they are HLA class I independent. Most importantly, $CD8^+$ T cells expressing CARs can be adoptively transferred back to the patient where they provide persistent targeted killing of target cells.

Antiretroviral therapy has improved the quality of life for $HIV^+$ individuals and can durably suppress HIV-1 replication. However, efficacy requires strict adherence to treatment regimens and despite undetectable levels of virus in patients' plasma, replication-competent virus persists in chronically infected, long-lived reservoirs in patients. Thus, antiretroviral therapy alone is not curative. This, coupled with the lifelong costs and potential for undesired side effects, have created an impetus for devising a treatment that enables cessation of antiretroviral therapy and there is therefore a need to identify alternative therapies.

SUMMARY

This disclosure provides chimeric antigen receptor (CAR) proteins, including multispecific CAR proteins. The multispecific CAR proteins can bind to HIV Env, or a fragment thereof, such a gp120, and are useful for controlling HIV infection. In several embodiments, the multispecific CAR proteins can be used to make a CAR T cell that is not susceptible to HIV infection.

In some embodiments, a multispecific chimeric antigen receptor protein comprises an N-terminal extracellular targeting segment comprising a first targeting domain comprising a CD4 derived domain that binds to HIV Env, and a second targeting domain comprising a carbohydrate recognition domain (CRD) derived from a human C-type lectin that binds to HIV Env. The first and second targeting domains bind to different sites on HIV Env, and the multispecific chimeric antigen receptor protein binds to HIV Env. In some embodiments, the multispecific chimeric antigen receptor comprises a linker connecting the first targeting domain to the second targeting domain. In additional embodiments, the CD4 derived domain and the carbohydrate recognition domain (CRD) of the multispecific chimeric antigen receptor protein bind to different sites on HIV Env. In additional embodiments, the multispecific chimeric antigen receptor protein further comprises a linker connecting the extracellular targeting moiety to a transmembrane domain, the transmembrane domain, a cytoplasmic co-stimulatory signaling domain, and a cytoplasmic effector function signaling domain.

In other embodiments, a multispecific chimeric antigen receptor protein comprises an N-terminal extracellular targeting segment comprising a first targeting domain comprising a CD4 derived domain that binds to gp120, and a second targeting domain comprising a scFv17b derived domain that binds to gp120. The first and second targeting domains of the multispecific chimeric antigen receptor protein bind to different sites on gp120. Additionally, the first targeting domain can be connected to the second targeting domain by a linker that is sufficiently short so that the first and second targeting domains do not bind to the same gp120 protein molecule simultaneously. In additional embodiments, the multispecific chimeric antigen receptor protein further comprises a transmembrane domain, a cytoplasmic co-stimulatory signaling domain, and a cytoplasmic effector function signaling domain. In several embodiments, the linker connecting the first targeting domain to the second targeting domain is no more than 20 amino acids long.

In some embodiments, the CAR proteins provided herein can have a transmembrane domain from CD28, a cytoplasmic co-stimulatory signaling domain from CD28, or a cytoplasmic signaling domain from CD3 zeta, or a combination thereof.

Specific examples of chimeric antigen receptor proteins, and recombinant proteins, are or comprise SEQ ID NO: 7 (CD4-10-17b); SEQ ID NO: 47 (CD4-DCSIGN CAR ectodomain), SEQ ID NO: 49 (CD4-LSIGN CAR ectodomain), SEQ ID NO: 51 (CD4-Langerin CAR ectodomain), or SEQ ID NO: 53 (CD4-MBL2 CAR ectodomain).

In additional embodiments, the multispecific CAR proteins provided herein can be expressed on a host cell, such as a T cell, for example a $CD8^+$ T cell and/or a $CD4^+$ T cell.

Also provided herein are nucleic acid molecules encoding the disclosed CAR proteins. In one embodiment the nucleic acid sequence encoding the disclosed multispecific CAR protein (or recombinant protein) is at least 80% identical to the nucleic acid sequence as set forth in SEQ ID NO: 6, SEQ ID NO: 46, SEQ ID NO: 48, SEQ ID NO: 50, or SEQ ID NO: 52. Isolated vectors comprising a nucleic acid sequence encoding a disclosed CAR protein are also envisioned. A recombinant cell can comprise the vector. The recombinant cell can be a human cell, such as a T cell. Also envisioned is a composition comprising the recombinant cell. In certain embodiments, the cell is an autologous cell, which can be used in treating the subject who is the source of the cell.

The herein disclosed CAR proteins are useful for binding an effector cell to an HIV-infected cell. They are further useful, when expressed in host T cells (such as autologous T cells), for killing HIV-infected cells or reducing the level of HIV infected cells in a subject infected with HIV. The CAR proteins are also useful for generating a CAR-expressing recombinant CD8 T cell that is not susceptible to HIV infection The foregoing and other objects, features, and advantages of the invention will become more apparent from the following detailed description, which proceeds with reference to the accompanying figures.

BRIEF DESCRIPTION OF THE DRAWINGS

FIG. 14A shows regulation of HIV-1 Env expression by doxycycline treatment. HeLa-TetOff cells were transfected with the inducible Env plasmid pGL4.22-JRFL under the indicated amounts of dox and assayed for Env expression by WB on cell lysates (top) and flow cytometry with live cells (bottom). FIG. 14B shows that CD4-based CARs render T cells highly responsive to target cells expressing Env, even at very low expression levels. The HeLa-Tet-Off system was used to vary expression levels of HIV-1 Env (JR-FL) as in FIG. 14A. During a 4 hr coculture, the CD4 and CD4-DCSIGN CARs induced IFN-γ secretion from target cells expressing varying levels of Env. The level of IFN-γ secretion was quite robust (~30%) even at the lowest JR-FL expression level, indicating the high responsiveness of the CAR-expressing T cells.

FIG. 15A 293T cells were individually transfected with expression constructs encoding ICAM-2 (left), ICAM-3 (middle), or HIV-1 Env (gp160, right) and analyzed for surface expression of the transgene by flow cytometry. FIG. 15B shows the amount of IFN-γ expressed by transfected 293T cells. 293T cells were seeded at $10^4$/well in a 96-well plate overnight and transfected the following day using FugeneHD with the indicated genes. After two days, the media was aspirated from each well and replaced with 100 μL fresh media containing $10^3$ effectors. The plate was incubated overnight, and the following day the media was analyzed using IFN-γELISA (Thermo EHIFNG kit).

FIG. 16A HOS.CCR5 cells were transduced with the indicated CAR gene and analyzed for CAR surface expression by flow cytometry using anti-CD4 (RPA-T4). FIG. 16B CAR-transduced HOS.CCR5 cells were cultured in 96-well white wall plates in the presence of varying dilutions of either of two HIV-Luc pseudovirus particles (BaL and YU2 envelopes) and assayed for luciferase activity 48 hrs post-infection. Untransduced HOS.CCR5 and HOS.CD4.CCR5 cells are included as negative and positive controls, respectively.

FIG. 17 shows results of FACS indicating that the "standard" CD4 CAR did confer HIV-1 susceptibility, whereas the CD4-DCSIGN CAR did not. CD8+ T-cells were isolated from PBMCs by MACS negative selection (Miltenyi Biotec). The cells were activated and transduced with the indicated CAR genes. Cell free HIV (BaL isolate) was added to the cultures and the cells were analyzed for infection by intracellular p24 staining three days later.

SEQUENCE LISTING

Figure 1:
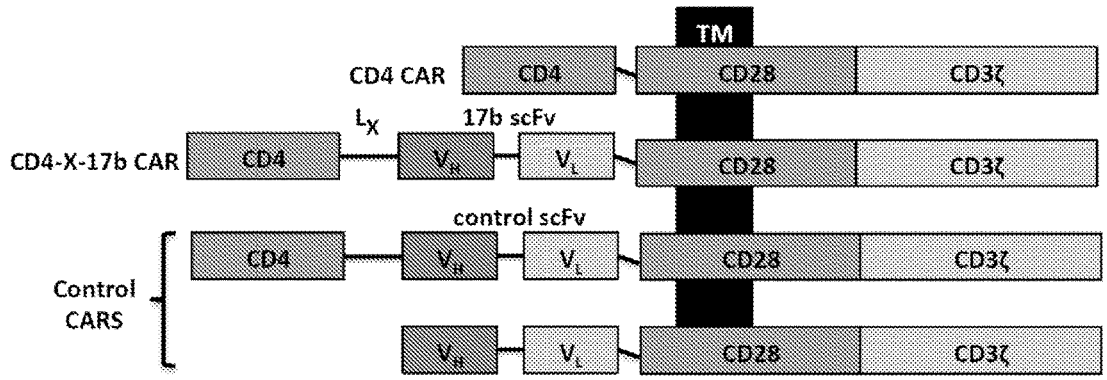
FIG. 1 is a schematic representation of various anti-HIV chimeric antigen receptors (CARs) expressed in a cell. CARs contain targeting (extracellular), transmembrane (TM) and intracellular (signaling) domains. Multispecific CARs contain two functional elements in the targeting extracellular domain, such as CD4 and 17b scFV moieties targeting HIV gp120 (e.g., CD4-X-17b CAR), in addition to a small extracellular segment of CD28, whereas monofunctional CARs (e.g., CD4 CAR) contain only a single functional element (in the targeting extracellular domain) and a small segment of CD28. The Lx linker attaches the CD4 moiety to the 17b scFv moiety and consists of repeats of the 5 amino acid sequence motif $G_4S$. Control CARs employ a control scFv, either alone or linked to CD4, directed against an antigen unrelated to HIV. All CARs contain a transmembrane segment plus intracellular signaling motifs, e.g. from CD28 and CD3-zeta.
Figure 2:
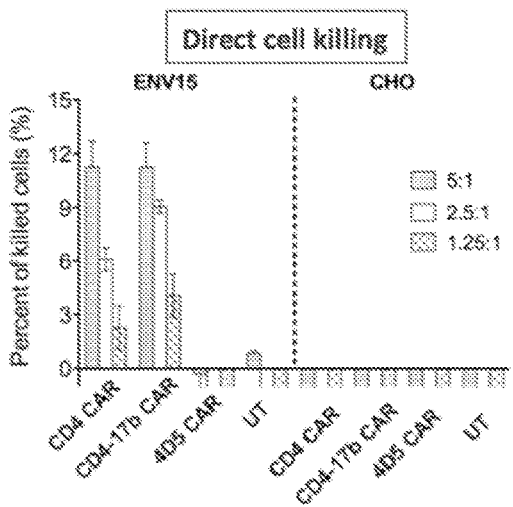
FIG. 2 is a bar graph illustrating direct killing of cells expressing HIV-1 Env by $CD8^+$ T cells expressing CAR molecules ($CAR^+$). Monospecific or multispecific CARP effector T cells were mixed with target cells (wildtype (WT) Chinese hamster ovary cells (CHO) or CHO cells expressing HIV-1 Env (Env15; also referred to as CHO/Env or CHO/Env15) at the indicated effector:target ratios. The CD4-17b CAR used in these studies was CD4-35-17b CAR, and included 7 repeats of the 5 amino acid sequence motif $G_4S$, which links the CD4 and 17b moieties. 4D5 CAR are $CD8^+$ T cells expressing a negative control CAR targeting an irrelevant antigen that is not expressed in this experimental system. This negative control CAR has identical transmembrane and intracellular signaling motifs (CD28+CD3ζ) as the CD4-CAR and CD4-17b-CAR. The extracellular domain of 4D5-CAR is composed of a scFv derived from a humanized mAb 4D5 (Herceptin). The target of 4D5 scFV is ErbB2, which is overexpressed on tumors such as breast cancer (Zhao et al., *J. Immunol.,* 183:5563-5574, 2009; Carter et al., *Proc. Natl. Acad. Sci.,* 89:4285-4289, 1992, both of which are incorporated herein by reference). Cytotoxicity was measured based on lactate dehydrogenase (LDH) release. Both monospecific and multispecific CD4-based CARs directly killed the Env15 cells, and had no effect on the CHO cells. In the illustrated experiment, the CD4-35-17b CAR was no more potent (in fact, somewhat less potent) than the CD4 CAR at the 5:1 effector:target ratio. However, at the 2.5:1 and 1.25:1 ratios, the CD4-35-17b CAR was more potent than the CD4 CAR in this experiment. In other experiments, the CD4-35-17b CAR was somewhat less potent than the CD4 CAR. UT: untransfected effector T cell (cells with no CAR).
Figure 3:
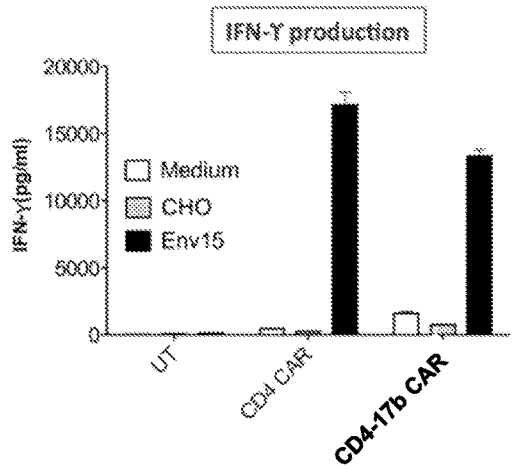
FIG. 3 is a bar graph illustrating interferon-gamma (IFN-γ) production from $CD8^+$ T cells expressing various CAR molecules upon interaction with cells expressing HIV-1 Env. Monospecific or multispecific $CAR^+$ effector T cells were cultured with either WT CHO or Env15 target cells in a 1:1 effector/target ratio. Supernatant was isolated after 18 hours of co-culture and interferon-γ secretion measured via ELISA. Both monofunctional and multispecific CD4-based CARs induced IFN-γ secretion upon interaction with Env 15 cells (but not control CHO cells). The CD4-35-17b CAR was no more potent (perhaps a bit less potent) than the CD4 CAR. UT: untransfected effector T cell (cells with no CAR).
Figure 4:
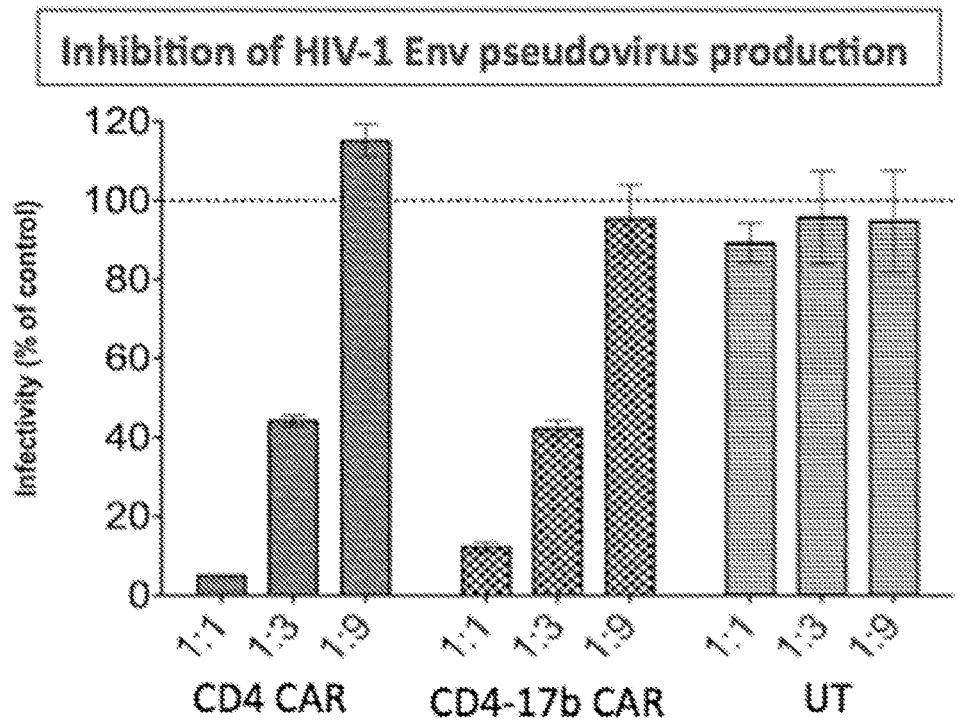
FIG. 4 is a bar graph illustrating the inhibition of HIV-1 Env pseudovirus production by $CD8^+$ T cells expressing various CAR molecules. Effector T cells (E) expressing the indicated CAR molecules were incubated with HIV particle producing 293T target cells (T) to measure inhibition of pseudotyped HIV production via CAR mediated killing of producer cells. Monospecific or multispecific $CAR^+$ effector T cells or control untransduced T cells (UT) were mixed with HIV particle producing 293T target cells at the indicated effector/target (E/T) ratios. Supernatants were isolated and viral titers were measured on SupT1 cells. Both CD4-based CARs suppressed HIV-1 Env pseudovirus production in dose-dependent fashion. The CD4-35-17b CAR was no more potent than the CD4 CAR.
Figure 5:
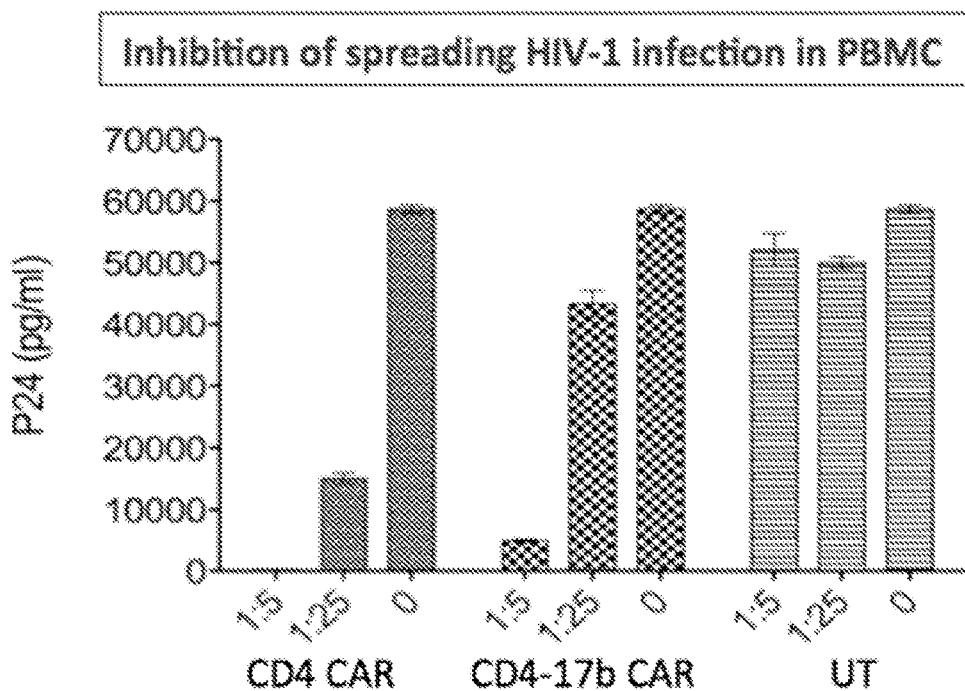
FIG. 5 is a bar graph illustrating the inhibition of spreading of HIV-1 infection in peripheral blood mononuclear cells (PBMC) by $CD8^+$ T cells expressing various CAR molecules. Monospecific or multispecific $CAR^+$ effector T cells were incubated with HIV-infected human PBMCs for 8 days. Supernatants were collected and p24 was quantified via ELISA as a measurement of HIV spread within the culture. Both monospecific and multispecific CD4-based CARs suppressed HIV-1 infection in PBMC. The CD4-35-17b CAR was no more potent (in fact, somewhat less potent) than the CD4 CAR. UT: untransfected effector T cells (cells with no CAR).

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named Sequence_Listing.txt, created on May 13, 2016, ~108 KB, which is incorporated by reference herein. In the accompanying sequence listing:

SEQ ID NO: 1 shows a representative basic repeat cassette for a linker polypeptide. The amino acid sequence of the basic repeat cassette is: GGGGS.

SEQ ID NO: 2 shows a representative seven-repeat polypeptide linker. The sequence of the seven-repeat polypeptide linker is: GGGGSGGGGSGGGGSGGGGSGGGGS GGGGSGGGGS.

SEQ ID NO: 3 shows a representative two-repeat polypeptide linker. The sequence of the two-repeat polypeptide linker is: GGGGSGGGGS.

SEQ ID NO: 4 shows the nucleic acid sequence of CD4-35-17b CAR, including the following features:
CD4 (D1, D2)—nucleotides 1-624;
$(G_4S)_7$ 35 amino acid linker—nucleotides 625-729;
17b scFv—nucleotides 730-1485, where nucleotides 1,114-1,158 correspond to a $(G_4S)_3$ linker between the $V_H$ and $V_L$ regions of scFv;
CD28—nucleotides 1489-1815, where nucleotides 1612-1692 correspond to the transmembrane region;
CD3ζ chain—nucleotides 1816-2154.
The nucleic acid sequence of CD4-35-17b CAR is:

atggttcgaggcgtgcccttccggcatctgctgctggtgctgcagctggc tctcctgcctgccgccacccagggcaagaaagtggtgctgggcaaaaagg gcgacaccgtgaactgacctgcaccgccagccagaagaagtccatccag ttccactggaagaacagcaaccagatcaagatcctgggcaaccagggcag cttcctgaccaagggccccagcaagctgaacgaccgggccgatagccggc ggagcctgtgggaccagggcaatttcccactgatcatcaagaacctgaag atcgaggacagcgacacctacatctgcgaggtcgaagatcagaaagaaga ggtgcagctgctggtgttcggcctgaccgccaactccgacacccatctgc tgcagggccagagcctgaccctcaccctggaaagcccccctggcagcagc cccagcgtgcagtgcagaagcccagaggcaagaacatccagggcggcaa gaccctgagcgtgtcccagctggaactgcaggactccggcacctggacct gtaccgtgctgcagaaccagaaaaaggtcgagttcaagatcgacatcgtg gtgctggccttccagaaggcctctggcggcggaggatctggcggaggtgg aagtggcggggaggtagtggcggaggcggatcaggtggcggaggttcag gcggtggcggaagcggaggcggtggatctcaggtccagctgctcgaatct ggcgccgaagtgaagaaacccggcagcagcgtgaaagtgtcctgcaaggc cagcggcgacaccttcatccggtacagcttcacatgggtccgacaggccc ctgggcagggcctggaatggatgggccggatcatcaccatcctggacgtg gcccactacgccccacatctgcagggcagagtgaccatcaccgccgacaa gagcaccagcaccgtgtacctggaactgcggaacctgcggagcgacgata ccgccgtctacttctgtgccgcgtgtacgagggcgaggccgatgagggc gagtacgacaacaacggcttcctgaagcactgggccagggcaccctcgt caccgtgaccagcggcggcggaggatctggcggaggtggaagtggcgggg gaggtagtgagctggaactcacccagagccccgccaccctgtccgtgtct ccaggcgagagagccaccctgagctgcagagccagcgagagcgtgtccag cgacctggcctggtatcagcagaagcccggccaggcccccagactgctga tctacggcgccagcaccagagccacaggcgtgccagccagattcagcggc agcggtagcggagccgagttcaccctgaccatcagcagcctgcagagcga ggactttgccgtgtactactgccagcagtacaacaactggccccccagat acaccttcggccagggaacccggctggaaatcaaggcggccgcaattgaa gttatgtatcctcctccttacctagacaatgagaagagcaatggaaccat tatccatgtgaaagggaaacacctttgtccaagtcccctatttcccggac cttctaagcccttttgggtgctggtggtggttggtggagtcctggcttgc tatagcttgctagtaacagtggcctttattatttttctgggtgaggagtaa gaggagcaggctcctgcacagtgactacatgaacatgactccccgccgcc ccgggcccacccgcaagcattaccagccctatgccccaccacgcgacttc gcagcctatcgctccagagtgaagttcagcaggagcgcagacgcccccgc gtaccagcagggccagaaccagctctataacgagctcaatctaggacgaa gagaggagtacgatgttttggacaagagacgtggccgggaccctgagatg ggggaaagccgagaaggaagaaccctcaggaaggcctgtacaatgaact gcagaaagataagatggcggaggcctacagtgagattgggatgaaaggcg agcgccggagggggcaaggggcacgatggcctttaccagggtctcagtaca gccaccaaggacacctacgacgcccttcacatgcaggccctgccccctcg ctaa SEQ ID NO: 5 shows the amino acid sequence of the CD4-35-17b CAR chimeric protein, including the following features:
CD4 (D1, D2)—amino acids 1-208;
$(G_4S)_7$ 35 amino acid linker—amino acids 209-243;
17b scFv—amino acids 244-495, where amino acids 372-386 correspond to a $(G_4S)_3$ linker between the $V_H$ and $V_L$ regions of scFv;
CD28—amino acids 497-605, where amino acids 538-564 correspond to the transmembrane region;
CD3ζ chain—amino acids 606-717.
The amino acid sequence of CD4-35-17b CAR is:

MVRGVPFRHLLLVLQLALLPAATQGKKVVLGKKGDTVELTCTASQKKSIQ
FHWKNSNQIKILGNQGSFLTKGPSKLNDRADSRRSLWDQGNFPLIIKNLK
IEDSDTYICEVEDQKEEVQLLVFGLTANSDTHLLQGQSLTLTLESPPGSS
PSVQCRSPRGKNIQGGKTLSVSQLELQDSGTWTCTVLQNQKKVEFKIDIV
VLAFQKASGGGGSGGGGSGGGGSGGGGSGGGGSGGGGSGGGGSQVQLLES
GAEVKKPGSSVKVSCKASGDTFIRYSFTWVRQAPGQGLEWMGRIITILDV
AHYAPHLQGRVTITADKSTSTVYLELRNLRSDDTAVYFCAGVYEGEADEG
EYDNNGFLKHWGQGTLVTVTSGGGGSGGGGSGGGGSELELTQSPATLSVS
PGERATLSCRASESVSSDLAWYQQKPGQAPRLLIYGASTRATGVPARFSG
SGSGAEFTLTISSLQSEDFAVYYCQQYNNWPPRYTFGQGTRLEIKAAAIE
VMYPPPYLDNEKSNGTIIHVKGKHLCPSPLFPGPSKPFWVLVVVGGVLAC
YSLLVTVAFIIFWVRSKRSRLLHSDYMNMTPRRPGPTRKHYQPYAPPRDF
AAYRSRVKFSRSADAPAYQQGQNQLYNELNLGRREEYDVLDKRRGRDPEM
GGKPRRKNPQEGLYNELQKDKMAEAYSEIGMKGERRRGKGHDGLYQGLST
ATKDTYDALHMQALPPR.

SEQ ID NO: 6 shows the nucleic acid sequence of CD4-10-17b CAR, including the following features:
CD4 (D1, D2)—nucleotides 1-624;
$(G_4S)_2$ 10 amino acid linker—nucleotides 625-654;
17b scFv—nucleotides 654-1410, where nucleotides 1,039-1,083 correspond to a $(G_4S)_3$ linker between the $V_H$ and $V_L$ regions of scFv;
CD28—nucleotides 1414-1740, where nucleotides 1537-1617 correspond to the transmembrane region;
CD3ζ chain—nucleotides 1741-2079.
The nucleic acid sequence of CD4-10-17b CAR is:

atggttcgaggcgtgcccttccggcatctgctgctggtgctgcagctggc
tctcctgcctgccgccacccagggcaagaaagtggtgctgggcaaaaagg
gcgacaccgtggaactgacctgcaccgccagccagaagaagtccatccag
ttccactggaagaacagcaaccagatcaagatcctgggcaaccaggggcag
cttcctgaccaagggccccagcaagctgaacgaccgggccgatagccggc
ggagcctgtgggaccagggcaatttcccactgatcatcaagaacctgaag
atcgaggacagcgacacctacatctgcgaggtcgaagatcagaaagaaga
ggtgcagctgctggtgttcggcctgaccgccaactccgacacccatctgc
tgcagggccagagcctgaccctcaccctggaaagcccccctggcagcagc
cccagcgtgcagtgcagaagcccagaggcaagaacatccagggcggcaa gaccctgagcgtgtcccagctggaactgcaggactccggcacctggacct
gtaccgtgctgcagaaccagaaaaaggtcgagttcaagatcgacatcgtg
gtgctggccttccagaaggcctctggcggtggcggaagcggaggcggtgg
atctcaggtccagctgctcgaatctggcgccgaagtgaagaaacccggca
gcagcgtgaaagtgtcctgcaaggccagcggcgacaccttcatccggtac
agcttcacatgggtccgacaggcccctgggcagggcctggaatggatggg
ccggatcatcaccatcctggacgtggcccactacgccccacatctgcagg
gcagagtgaccatcaccgccgacaagagcaccagcaccgtgtacctggaa
ctgcggaacctgcggagcgacgataccgccgtctacttctgtgccggcgt
gtacgagggcgaggccgatgagggcgagtacgacaacaacggcttcctga
agcactggggccagggcaccctcgtcaccgtgaccagcggcggcggagga
tctggcggaggtggaagtggcggggggaggtagtgagctggaactcaccca
gagccccgccaccctgtccgtgtctccaggcgagagagccaccctgagct
gcagagccagcgagagcgtgtccagcgacctggcctggtatcagcagaag
cccggccaggcccccagactgctgatctacggcgccagcaccagagccac
aggcgtgccagccagattcagcggcagcggtagcggagccgagttcaccc
tgaccatcagcagcctgcagagcgaggactttgccgtgtactactgccag
cagtacaacaactggcccccagatacaccttcggccagggaacccggct
ggaaatcaaggcggccgcaattgaagttatgtatcctcctcttacctag
acaatgagaagagcaatggaaccattatccatgtgaaagggaaacacctt
tgtccaagtccctatttcccggaccttctaagcccttttgggtgctggt
ggtggttggtggagtcctggcttgctatagcttgctagtaacagtggcct
ttattattttctgggtgaggagtaagaggagcaggctcctgcacagtgac
tacatgaacatgactccccgccgcccccgggcccacccgcaagcattacca
gccctatgccccaccacgcgacttcgcagcctatcgctccagagtgaagt
tcagcaggagcgcagacgcccccgcgtaccagcagggccagaaccagctc
tataacgagctcaatctaggacgaagagaggagtacgatgttttggacaa
gagacgtggccgggaccctgagatggggggaaagccgagaaggaagaacc
ctcaggaaggcctgtacaatgaactgcagaaagataagatggcggaggcc
tacagtgagattgggatgaaaggcgagcgccggaggggcaagggggcacga
tggcctttaccagggtctcagtacagccaccaaggacacctacgacgccc
ttcacatgcaggccctgccccctcgctaa.

SEQ ID NO: 7 shows the amino acid sequence of the CD4-10-17b CAR chimeric protein, including the following features:
CD4 (D1, D2)—amino acids 1-208;
$(G_4S)_2$ 10 amino acid linker—amino acids 209-218;
17b scFv—amino acids 219-470, where amino acids 347-361 correspond to a $(G_4S)_3$ linker between the $V_H$ and $V_L$ regions of scFv;
CD28—amino acids 472-580, where amino acids 513-539 correspond to the transmembrane region;
CD3ζ chain—amino acids 581-692.

The amino acid sequence of CD4-10-17b CAR is:

MVRGVPFRHLLLVLQLALLPAATQGKKVVLGKKGDTVELTCTASQKKSIQF
HWKNSNQIKILGNQGSFLTKGPSKLNDRADSRRSLWDQGNFPLIIKNLKIE
DSDTYICEVEDQKEEVQLLVEGLTANSDTHLLQGQSLTLTLESPPGSSPSV
QCRSPRGKNIQGGKTLSVSQLELQDSGTWTCTVLQNQKKVEFKIDIVVLAF
QKASGGGGSGGGGSQVQLLESGAEVKKPGSSVKVSCKASGDTFIRYSFTWV
RQAPGQGLEWMGRIITILDVAHYAPHLQGRVTITADKSTSTVYLELRNLRS
DDTAVYFCAGVYEGEADEGEYDNNGFLKHWGQGTLVTVSGGGGSGGGGSG
GGGSELELTQSPATLSVSPGERATLSCRASESVSSDLAWYQQKPGQAPRLL
IYGASTRATGVPARFSGSGSGAEFTLTISSLQSEDFAVYYCQQYNNWPPRY
TFGQGTRLEIKAAAIEVMYPPPYLDNEKSNGTIIHVKGKHLCPSPLFPGPS
KPFWVLVVVGGVLACYSLLVTVAFIIFWVRSKRSRLLHSDYMNMTPRRPGP
TRKHYQPYAPPRDFAAYRSRVKFSRSADAPAYQQGQNQLYNELNLGRREEY
DVLDKRRGRDPEMGGKPRRKNPQEGLYNELQKDKMAEAYSEIGMKGERRRG
KGHDGLYQGLSTATKDTYDALHMQALPPR.

SEQ ID NO: 8 shows the nucleic acid sequence of CD4-DDY3 CAR, including the following features:
CD4 (D1, D2)—nucleotides 1-624;
$(G_4S)_7$ 35 amino acid linker—nucleotides 625-729;
DDY3 scFv—nucleotides 730-1,458, where nucleotides 1,072-1,116 correspond to a $(G_4S)_3$ linker between the $V_H$ and $V_L$ regions of scFv;
CD28—nucleotides 1,462-1,788, where nucleotides 1,585-1,665 correspond to the transmembrane region;
CD3ζ chain—nucleotides 1789-2127.
The nucleic acid sequence of CD4-DDY3 CAR is:

atggttcgaggcgtgcccttccggcatctgctgctggtgctgcagctggct
ctcctgcctgccgccacccagggcaagaaagtggtgctgggcaaaaagggc
gacaccgtggaactgacctgcaccgccagccagaagaagtccatccagttc
cactggaagaacagcaaccagatcaagatcctgggcaaccagggcagcttc
ctgaccaagggccccagcaagctgaacgacgggccgatagccggcggagc
ctgtgggaccagggcaatttcccactgatcatcaagaacctgaagatcgag
gacagcgacacctacatctgcgaggtcgaagatcagaaagaagaggtgcag
ctgctggtgttcggcctgaccgccaactccgacacccatctgctgcagggc
cagagcctgaccctcaccctggaaagcccccctggcagcagcccagcgtg
cagtgcagaagcccagaggcaagaacatccagggcggcaagaccctgagc
gtgtcccagctggaactgcaggactccggcacctggacctgtaccgtgctg
cagaaccagaaaaaggtcgagttcaagatcgacatcgtggtgctggccttc
cagaaggcctctggcggcggaggatctggcggaggtggaagtggcggggga
ggtagtggcggaggcggatcaggtggcggaggttcaggcggtggcggaagc
ggaggcggtggatctgaagtgcagctggtgcagtctggcgccgaagtgaag
aaacctggcgccaccgtgaagatcagctgcaaggtgtccggctacaccttc
accgactacatgcactgggtgcagcaggcccctggcaagggcctggaa
tggatgggactggtggaccccgaggacggcgagacaatctacgccgagaag ttccagggcagagtgaccatcaccgccgataccagcaccgacaccgcctac
atggaactgagcagcctgcggagcgaggacaccgccgtgtactactgtgcc
accgagcggaccgattactggggccagggaacactcgtgaccgtgtcaagt
ggcggcggaggatctggcggaggtggaagtggcggggaggtagtgagatc
gtgctgacccagagccccctgtccctgtctgtgacacctggcgagcctgcc
agcatctcctgcagaagcagccagagcctgctggactccgacgacggcaac
acctacctggactggtatctgcagaaacccggccagtcccccagctgctg
atctacgaggtgtccaaccggttcagcggcgtgcccgatagatttccggc
tctggcagcggcaccgacttcaccctgaagattagccgggtggaagccgag
gacgtgggcgtgtactattgcatgcagagcatccagctgccttggaccttc
ggccagggcaccaagctggaaatcaagagagcggccgcaattgaagttatg
tatcctcctccttacctagacaatgagaagagcaatggaaccattatccat
gtgaaagggaaacacctttgtccaagtccctatttcccggaccttctaag
cccttttgggtgctggtggtggaggtggagtcctggcttgctatagcttgc
tagtaacagtggccatattattactgggtgaggagtaagaggagcaggctc
ctgcacagtgactacatgaacatgactccccgccgcccccgggcccacccgc
aagcattaccagccctatgccccaccacgcgacttcgcagcctatcgctcc
agagtgaagttcagcaggagcgcagacgcccccgcgtaccagcagggccag
aaccagctctataacgagctcaatctaggacgaagagaggagtacgatgtt
ttggacaagagacgtggccgggaccctgagatgggggggaaagccgagaagg
aagaaccctcaggaaggcctgtacaatgaactgcagaaagataagatggcg
gaggcctacagtgagattgggatgaaaggcgagcgccggaggggcaaggg
cacgatggcctttaccagggtctcagtacagccaccaaggacacctacgac
gcccttcacatgcaggccctgccccctcgctaa.

SEQ ID NO: 9 shows the amino acid sequence of the CD4-DDY3 CAR chimeric protein, including the following features:
CD4 (D1, D2)—amino acids 1-208;
$(G_4S)_2$ 10 amino acid linker—amino acids 209-243;
DDY3 scFv—amino acids 244-486, where amino acids 358-372 correspond to a $(G_4S)_7$ linker between the $V_H$ and $V_L$ regions of scFv;
CD28—amino acids 487-596, where amino acids 529-555 correspond to the transmembrane region;
CD3ζ chain—amino acids 597-708.
The amino acid sequence of CD4-DDY3 CAR is:

MVRGVPFRHLLLVLQLALLPAATQGKKVVLGKKGDTVELTCTASQKKSIQF
HWKNSNQIKILGNQGSFLTKGPSKLNDRADSRRSLWDQGNFPLIIKNLKIE
DSDTYICEVEDQKEEVQLLVEGLTANSDTHLLQGQSLTLTLESPPGSSPSV
QCRSPRGKNIQGGKTLSVSQLELQDSGTWTCTVLQNQKKVEFKIDIVVLAF
QKASGGGGSGGGGSGGGGSGGGGSGGGGSGGGGSEVQLVQSGAEVK
KPGATVKISCKVSGYTFTDYYMHWVQQAPGKGLEWMGLVDPEDGETIYAEK
EQGRVTITADTSTDTAYMELSSLRSEDTAVYYCATERTDYWGQGTLVTVSS
GGGGSGGGGSGGGGSEIVLTQSPLSLSVTPGEPASISCRSSQSLLDSDDGN

-continued

TYLDWYLQKPGQSPQLLIYEVSNRFSGVPDRFSGSGSGTDFTLKISRVEAE

DVGVYYCMQSIQLPWTEGQGTKLEIKRAAAIEVMYPPPYLDNEKSNGTIIH

VKGKHLCPSPLFPGPSK<u>PFWVLVVVGGVLACYSLLVTVAFIIFWV</u>RSKRSR

LLHSDYMNMTPRRPGPTRKHYQPYAPPRDFAAYRSRVKFSRSADAPAYQQG

QNQLYNELNLGRREEYDVLDKRRGRDPEMGGKPRRKNPQEGLYNELQKDKM

AEAYSEIGMKGERRRGKGHDGLYQGLSTATKDTYDALHMQALPPR.

SEQ ID NOs: 10-45 show the amino acid sequences of variable regions of monoclonal antibodies, as follows:

| SEQ ID NO: | Variable chain | Monoclonal antibody | GenBank ID |
|---|---|---|---|
| 10 | light | PG9 | ADA54571 |
| 11 | heavy | PG9 | ADA54566.1 |
| 12 | light | PG16 | ADA54570.1) |
| 13 | heavy | PG16 | ADA54565.1 |
| 14 | light | PGT1 | AEN14419.1 |
| 15 | heavy | PGT1 | AEN14402.1 |
| 16 | light | PGT2 | AEN14420.1 |
| 17 | heavy | PGT2 | AEN14403.1 |
| 18 | light | PGT3 | AEN14421.1 |
| 19 | heavy | PGT3 | AEN14404.1 |
| 20 | light | PGT4 | AEN14422.1 |
| 21 | heavy | PGT4 | AEN14405.1 |
| 22 | light | PGT5 | AEN14423.1 |
| 23 | heavy | PGT5 | AEN14406.1 |
| 24 | light | 48d | AAR88370.1 |
| 25 | heavy | 48d | AAR88369.1 |
| 26 | light | 412d | AAR88380.1 |
| 27 | heavy | 412d | AAR88379.1 |
| 28 | light | 16c | AAR88374.1 |
| 29 | heavy | 16c | AAR88373.1 |
| 30 | light | 23e | AAR88376.1 |
| 31 | heavy | 23e | AAR88375.1 |
| 32 | light | 411G | AAR88372.1 |
| 33 | heavy | 411G | AAR88371.1 |
| 34 | light | 4E10 | 4LLV_L |
| 35 | heavy | 4E10 | 4LLV_H |
| 36 | light | 2F5 | 2P8L-A |
| 37 | heavy | 2F5 | 2P8L-B |
| 38 | light | 2G12 | 1OM3K |
| 39 | heavy | 2G12 | 1OM3:L3 |
| 40 | light | 10E8 | 4G6F:D |
| 41 | heavy | 10E8 | 4G6F:H |
| 42 | light | z13e1 | 3FN0:L |
| 43 | heavy | z13e1 | 3FN0:H |
| 44 | light | x5 | 1RHH:A |
| 45 | heavy | x5 | 1RHH:D |

SEQ ID NO: 46 shows the nucleotide sequence of the CD4-DCSIGN CAR ectodomain. The sequence is:

atggttcgggggtgcccttccgacatctgctgctggtcctgcagctggct ctgctgcctgccgctactcaggggaaaaagtcgtgctggggaagaaaggc gacacagtggagctgacctgcacagcttctcagaagaaaagtatccagttc cactggaagaactctaatcagatcaaaattctgggaaaccagggcagcttt ctgactaagggcccatccaaactgaatgaccgcgcagatagtcggagatca ctgtgggatcaggggaacttcccctgatcattaagaatctgaaaatcgaa gacagtgatacatactttgtgaggtggaagaccagaaggaggaagtgcag ctgctggtctttggactgacagccaactccgatactcatctgctgcaggc cagtctctgactctgaccctggagagtccacctggaagctccccatcagtg cagtgcaggagccctcgaggaaagaacatccagggcgggaaaacctgtca gtcagccagctggaactgcaggactccgggacatggacttgtaccgtgctg cagaatcagaagaaagtcgagttcaagatcgatattgtggtcctggctttt cagaaagcttccggaggcgggggatctatctaccaggagctgactcagctg aaggccgctgtggaaagactgtgccacccatgtccctgggagtggaccttc tttcagggaaactgctatttcatgtccaactctcagaggaattggcatgac tccatcaccgcctgtaaggaagtgggcgctcagctggtggtcatcaagtct gctgaggaacagaacttcctgcagctgcagtctagtcgatcaaatcggttt acctggatgggcctgagcgacctgaaccaggagggcacatggcagtgggtg gatgggagtcctctgctgccttcattcaagcagtattggaatcgaggggaa cctaacaatgtcggagaggaagattgcgcagagttcagcggcaacgggtgg aatgacgataagtgtaatctggccaaattttggatctgcaagaaaagcgca gcctcctgtagtcgggacgaggagcagtttctgagcccagcaccagcaaca cccaacccaccaccagcc SEQ ID NO: 47 shows the amino acid sequence of the CD4-DCSIGN CAR ectodomain, having the following features:
CD4 (D1, D2)—amino acids 1-208 (of which amino acids 1-25 form the leader peptide);
Gly$_4$Ser amino acid linker—amino acids 209-213; and
DCSIGN CRD—amino acids 214-380.
The sequence of the CD4-DCSIGN CAR ectodomain is:

MVRGVPFRHLLLVLQLALLPAATQGKKVVLGKKGDTVELTCTASQKKSIQ

FHWKNSNQIKILGNQGSFLTKGPSKLNDRADSRRSLWDQGNFPLIIKNLK

IEDSDTYICEVEDQKEEVQLLVEGLTANSDTHLLQGQSLTLTLESPPGSS

PSVQCRSPRGKNIQGGKTLSVSQLELQDSGTWTCTVLQNQKKVEFKIDIV

VLAFQKASGGGGSIYQELTQLKAAVERLCHPCPWEWTFFQGNCYFMSNSQ

RNWHDSITACKEVGAQLVVIKSAEEQNFLQLQSSRSNRFTWMGLSDLNQE

GTWQWVDGSPLLPSFKQYWNRGEPNNVGEEDCAEFSGNGWNDDKCNLAKF

WICKKSAASCSRDEEQFLSPAPATPNPPPA

SEQ ID NO: 48 shows the nucleotide sequence of the CD4-LSIGN CAR ectodomain. The sequence is:

atggttcgggggtgcccttccgacatctgctgctggtcctgcagctggc tctgctgcctgccgctactcaggggaaaaagtcgtgctggggaagaaag gcgacacagtggagctgacctgcacagcttctcagaagaaaagtatccag ttccactggaagaactctaatcagatcaaaattctgggaaaccagggcag ctttctgactaagggcccatccaaactgaatgaccgcgcagatagtcgga gatcactgtgggatcaggggaacttcccctgatcattaagaatctgaaa atcgaagacagtgatacatactttgtgaggtggaagaccagaaggagga agtgcagctgctggtctttggactgacagccaactccgatactcatctgc tgcaggccagtctctgactctgaccctggagagtccacctggaagctcc ccatcagtgcagtgcaggagccctcgaggaaagaacatccagggcggaa -continued
```
aaccctgtcagtcagccagctggaactgcaggactccgggacatggactt gtaccgtgctgcagaatcagaagaaagtcgagttcaagatcgatattgtg gtcctggcttttcagaaagcttccggaggcgggggatctatctaccagga gctgaccgacctgaagaccgccttcgagaggctgtgcaggcactgcccca aggactggaccttcttccagggcaactgctacttcatgagcaacagccag aggaactggcacgacagcgtgaccgcctgccaggaggtgagggcccagct ggtggtcatcaagaccgccgaggagcagaacttcctgcagctgcagacca gcaggagcaacaggttcagctggatgggcctgagcgacctgaaccaggag ggcacctggcagtgggtggacggcagcccctgagcccagcttccagag gtactggaacagcggcgagcccaacaacagcggcaacgaggactgcgccg agttcagcggcagcggctggaacgacaacaggtgcgacgtggacaactac tggatctgcaagaagcccgccgcctgcttcagggac
```

SEQ ID NO: 49 shows the amino acid sequence of the CD4-DCSIGNR CAR (CD4-LSIGN CAR) ectodomain.
CD4 (D1, D2)—amino acids 1-208 (of which amino acids 1-25 form the leader peptide);
Gly₄Ser amino acid linker—amino acids 209-213; and
LSIGN portion of last neck domain and CRD (UniProtKB/Swiss-Prot: Q9H2X3.1)—amino acids 214-362 (CRD begins at 229).
The sequence of the CD4-DCSIGNR CAR ectodomain is:

```
MVRGVPFRHLLLVLQLALLPAATQGKKVVLGKKGDTVELTCTASQKKSIQ

FHWKNSNQIKILGNQGSFLTKGPSKLNDRADSRRSLWDQGNFPLIIKNLK

IEDSDTYICEVEDQKEEVQLLVEGLTANSDTHLLQGQSLTLTLESPPGSS

PSVQCRSPRGKNIQGGKTLSVSQLELQDSGTWTCTVLQNQKKVEFKIDIV

VLAFQKASGGGGSIYQELTDLKTAFERLCRHCPKDWTFFQGNCYFMSNSQ

RNWHDSVTACQEVRAQLVVIKTAEEQNFLQLQTSRSNRFSWMGLSDLNQE

GTWQWVDGSPLSPSFQRYWNSGEPNNSGNEDCAEFSGSGWNDNRCDVDNY

WICKKPAACFRD
```

SEQ ID NO: 50 shows the nucleotide sequence of the CD4-Langerin CAR ectodomain. The sequence is:

```
atggttcgggggtgcccttccgacatctgctgctggtcctgcagctggc tctgctgcctgccgctactcaggggaaaaagtcgtgctggggaagaaag gcgacacagtggagctgacctgcacagcttctcagaagaaaagtatccag ttccactggaagaactctaatcagatcaaaattctgggaaaccagggcag ctttctgactaagggcccatccaaactgaatgaccgcgcagatagtcgga gatcactgtgggatcaggggaacttccccctgatcattaagaatctgaaa atcgaagacagtgatacatatttgtgaggtggaagaccagaaggagga agtgcagctgctggtctttggactgacagccaactccgatactcatctgc tgcagggccagtctctgactctgaccctggagagtccacctggaagctcc ccatcagtgcagtgcaggagccctcgaggaaagaacatccagggcgggaa aaccctgtcagtcagccagctggaactgcaggactccgggacatggactt gtaccgtgctgcagaatcagaagaaagtcgagttcaagatcgatattgtg gtcctggcttttcagaaagcttccggaggcggggatctcagaatgatat cctgcaggtggtgagccagggctggaagtacttcaaagggaatttctact atttttccctgattcctaagacatggtattctgccgagcagttctgcgtg tcaaggaacagccacctgacctccgtgacatctgagagtgaacaggagtt tctgtacaagaccgccggcggactgatctattggattgggctgacaaaag ctggaatggagggcgactggagttgggtggacgataccccattcaataag gtgcagtcagtgcggttttggatccccggagaacctaacaatgccggcaa caatgagcattgcgggaacatcaaggctcctagcctgcaggcctggaatg acgctccatgcgataagacattcctgtttatctgtaaaaggccatatgtg ccctccgaacct
```

SEQ ID NO: 51 shows the amino acid sequence of the CD4-Langerin CAR ectodomain.
CD4 (D1, D2)—amino acids 1-208 (of which amino acids 1-25 form the leader peptide);
Gly₄Ser amino acid linker—amino acids 209-213; and
Langerin CRD (GenBank: EAW99793.1)—amino acids 214-354.
The sequence of the CD4-Langerin CAR ectodomain is:

```
MVRGVPFRHLLLVLQLALLPAATQGKKVVLGKKGDTVELTCTASQKKSIQ

FHWKNSNQIKILGNQGSFLTKGPSKLNDRADSRRSLWDQGNFPLIIKNLK

IEDSDTYICEVEDQKEEVQLLVFGLTANSDTHLLQGQSLTLTLESPPGSS

PSVQCRSPRGKNIQGGKTLSVSQLELQDSGTWTCTVLQNQKKVEFKIDIV

VLAFQKASGGGGSQNDILQVVSQGWKYFKGNFYYFSLIPKTWYSAEQFCV

SRNSHLTSVTSESEQEFLYKTAGGLIYWIGLTKAGMEGDWSWVDDTPFNK

VQSVRFWIPGEPNNAGNNEHCGNIKAPSLQAWNDAPCDKTFLFICKRPYV

PSEP
```

SEQ ID NO: 52 shows the nucleotide sequence of the CD4-MBL2 CAR ectodomain. The sequence is:

```
atggttcgggggtgcccttccgacatctgctgctggtcctgcagctggc tctgctgcctgccgctactcaggggaaaaagtcgtgctggggaagaaag gcgacacagtggagctgacctgcacagcttctcagaagaaaagtatccag ttccactggaagaactctaatcagatcaaaattctgggaaaccagggcag ctttctgactaagggcccatccaaactgaatgaccgcgcagatagtcgga gatcactgtgggatcaggggaacttccccctgatcattaagaatctgaaa atcgaagacagtgatacatatttgtgaggtggaagaccagaaggagga agtgcagctgctggtctttggactgacagccaactccgatactcatctgc tgcagggccagtctctgactctgaccctggagagtccacctggaagctcc ccatcagtgcagtgcaggagccctcgaggaaagaacatccagggcgggaa aaccctgtcagtcagccagctggaactgcaggactccgggacatggactt gtaccgtgctgcagaatcagaagaaagtcgagttcaagatcgatattgtg gtcctggcttttcagaaagcttccggaggcggggatctaagcaagtggg
```

-continued
```
aaacaaattctttctgaccaatggcgagattatgacattcgaaaaggtga aagctctgtgcgtcaagtttcaggcctccgtggctaccccctcgaaacgca gccgagaatggggctatccagaacctgattaaggaggaagcattcctggg catcacagacgagaaaactgaaggccagtttgtggatctgacaggaaata ggctgacttacaccaactggaatgaggggggaaccaaacaatgccggttcc gacgaggattgcgtgctgctgctgaagaacggccagtggaatgacgtgcc ctgcagcacctctcacctggctgtctgtgagttccctatt
```

SEQ ID NO: 53 shows the nucleotide sequence of the CD4-MBL2 CAR ectodomain.
CD4 (D1, D2)—amino acids 1-208 (of which amino acids 1-25 form the leader peptide);
Gly$_4$Ser amino acid linker—amino acids 209-213; and
MBL2 CRD (Uniprot: P11226)—amino acids 214-330.
The sequence of the CD4-MBL2 CAR ectodomain is:

```
MVRGVPFRHLLLVLQLALLPAATQGKKVVLGKKGDTVELTCTASQKKSIQ

FHWKNSNQIKILGNQGSFLTKGPSKLNDRADSRRSLWDQGNFPLIIKNLK

IEDSDTYICEVEDQKEEVQLLVFGLTANSDTHLLQGQSLTLTLESPPGSS

PSVQCRSPRGKNIQGGKTLSVSQLELQDSGTWTCTVLQNQKKVEFKIDIV

VLAFQKASGGGGSKQVGNKFFLTNGEIMTFEKVKALCVKFQASVATPRNA

AENGAIQNLIKEEAFLGITDEKTEGQFVDLTGNRLTYTNWNEGEPNNAGS

DEDCVLLLKNGQWNDVPCSTSHLAVCEFPI
```

SEQ ID NO: 54 shows the amino acid sequence of a possible CD8 transmembrane domain for use in a CAR. The sequence is:

```
TTTPAPRPPTPAPTIASQPLSLRPEACRPAAGGAVHTRGLDFACDIYIWA

PLAGTCGVLLLSLVITLYC
```

SEQ ID NO: 55 shows the amino acid sequence of a possible CD28 transmembrane domain for use in a CAR. The sequence is:

```
IEVMYPPPYLDNEKSNGTIIHVKGKHLCPSPLFPGPSKPFWVLVVVGGVL

ACYSLLVTVAFIIFWVR
```

SEQ ID NO: 56 shows the amino acid sequence of a possible zeta signaling domain for use in a CAR. The sequence is:

```
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR),
```

SEQ ID NO: 57 shows the amino acid sequence of a possible CD8 signaling domain for use in a CAR. The sequence is:

```
FVPVFLPAKPTTTPAPRPPTPAPTIASQPLSLRPEACRPAAGGAVHTRGL

DFACDIYIWAPLAGTCGVLLLSLVITLYCNHRNR
```

SEQ ID NO: 58 shows the amino acid sequence of a possible CD28 signaling domain for use in a CAR. The sequence is:

```
SKRSRLLHSDYMNMTPRRPGPTRKHYQPYAPPRDFAAYRS.
```

SEQ ID NO: 59 shows the amino acid sequence of a possible CD137 signaling domain for use in a CAR. The sequence is:

```
RFSVVKRGRKKLLYIFKQPFMRPVQTTQEEDGCSCRFPEEEEGGCEL.
```

DETAILED DESCRIPTION

I. Abbreviations

APC allophycocyanin
CAR chimeric antigen receptor
CARP CAR-expressing cell
CHO Chinese hamster ovary
CIR chimeric immune receptor
CLEC C-type lectin
CRD carbohydrate recognition domain
CTL cytotoxic T lymphocytes
DMEM Dulbecco's Modified Eagle Medium
Env envelope glycoprotein complex of HIV
FACS fluorescence activated cell sorting
FITC fluorescein isothiocyanate
Fv antibody "fragment variable", the variable region of an antibody
gp120 external subunit of the envelope glycoprotein complex of HIV
HIV human immunodeficiency virus
IFN-γ interferon-gamma
LDH lactate dehydrogenase
MAb monoclonal antibody
MTX methotrexate
NK natural killer cells
PBMC peripheral blood mononuclear cells
PBS phosphate buffered saline
PE phycoerythrin
scFv single-chain antibody variable region
TIL tumor-infiltrating lymphocytes

II. Explanation of Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

17b: A monoclonal antibody that specifically binds to a CD4-induced epitope on HIV-1 Env, that is, CD4 binding causes a conformation changes in HIV-1 Env that exposes the 17b epitope. The 17b antibody does not specifically bind to HIV-1 Env in its prefusion mature closed conformation. The person of ordinary skill in the art is familiar with monoclonal antibody 17b and with methods of producing this antibody (see, for example, Kwong et al., *J. Biol. Chem.,* 274, 4115-4123, 1999, which is incorporated by reference herein). The amino acid sequences of the heavy and light variable regions of the 17b antibody are known and have been deposited in GenBank as Nos. 1G9N_H (17b $V_H$) and 1G9N_L (17b $V_L$), each of which is incorporated by reference herein as present in the database on Aug. 22, 2014).

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes. In some examples a disclosed antibody specific for an HIV Env protein or polypeptide, or a nucleic acid encoding the antibody, is administered to a subject.

Agent: Any substance or any combination of substances that is useful for achieving an end or result; for example, a substance or combination of substances useful for inhibiting HIV infection in a subject. Agents include proteins, antibodies, nucleic acid molecules, compounds, small molecules, organic compounds, inorganic compounds, or other molecules of interest. An agent can include a therapeutic agent (such as an anti-retroviral agent), a diagnostic agent or a pharmaceutical agent. In some embodiments, the agent is a polypeptide agent (such as a HIV-neutralizing antibody), or an anti-viral agent. The skilled artisan will understand that particular agents may be useful to achieve more than one result.

Amino acid substitution: The replacement of one amino acid in peptide with a different amino acid.

Animal: Living multi-cellular vertebrate organisms, a category that includes, for example, mammals and birds. The term mammal includes both human and non-human mammals.

Antibody: A polypeptide ligand that specifically binds and recognizes an analyte (antigen), and which comprises at least a light chain or heavy chain immunoglobulin variable region, which specifically recognizes and binds an epitope of an antigen. Antibodies can be composed of a heavy and/or a light chain, each of which has a variable region, termed the variable heavy ($V_H$) region and the variable light ($V_L$) region. Together, the $V_H$ region and the $V_L$ region are responsible for binding the antigen recognized by the antibody. This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). The term also includes recombinant forms such as chimeric antibodies (for example, humanized antibodies) and heteroconjugate antibodies (such as, bispecific antibodies). See also, Pierce Catalog and Handbook, 1994-1995 (Pierce Chemical Co., Rockford, Ill.); Kuby, Immunology, 3rd Ed., W.H. Freeman & Co., New York, 1997.

The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, $2^{nd}$ Ed., Springer Press, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science,* 242:423-426, 1988; Huston et al., *Proc. Natl. Acad. Sci.,* 85:5879-5883, 1988; Ahmad et al., *Clin. Dev. Immunol.,* 2012, doi:10.1155/2012/980250; Marbry, IDrugs, 13:543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the heavy and light chain variable chains have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci.,* 90:6444-6448, 1993; Poljak et al., *Structure,* 2:1121-1123, 1994).

Antibodies also include genetically engineered forms such as chimeric antibodies (such as humanized murine antibodies) and heteroconjugate antibodies (such as bispecific antibodies). See also, *Pierce Catalog and Handbook,* 1994-1995 (Pierce Chemical Co., Rockford, Ill.); Kuby, *Immunology,* $3^{rd}$ Ed., W.H. Freeman & Co., New York, 1997.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6.sup.th ed., W.H.

Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). References to "$V_H$" or "VH" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

Light and heavy chain variable regions contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (*JMB* 273,927-948, 1997; "Chothia" numbering scheme), and Lefranc et al. ("IMGT unique numbering for immunoglobulin and T cell receptor variable domains and Ig superfamily V-like domains," *Dev. Comp. Immunol.*, 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable domain of the heavy chain of the antibody in which it is found, whereas a $V_L$ CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

A "monoclonal antibody" is an antibody produced by a single clone of B-lymphocytes or by a cell into which nucleic acid encoding the light and heavy chains of a single antibody have been transfected, or a progeny thereof. Monoclonal antibodies are produced by methods known to those of skill in the art, for instance by making hybrid antibody-forming cells from a fusion of myeloma cells with immune spleen cells. These fused cells and their progeny are termed "hybridomas." In some examples monoclonal antibodies are isolated from a subject. Monoclonal antibodies can have conservative amino acid substitutions which have substantially no effect on antigen binding or other immunoglobulin functions. (See, for example, Harlow & Lane, *Antibodies, A Laboratory Manual*, 2$^{nd}$ ed. Cold Spring Harbor Publications, New York (2013).)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

Antigen-specific effector cells or target-specific effector cells: Effector cells of the immune system or immune effector cells that are genetically modified to have an effector function. In some embodiments, the effector cells express the multispecific CAR protein disclosed herein by transfer of an expression construct or nucleic acid encoding said CAR multispecific protein.

Anti-retroviral agent: An agent that specifically inhibits a retrovirus from replicating or infecting cells. Non-limiting examples of antiretroviral drugs include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon).

Anti-retroviral therapy (ART): A therapeutic treatment for HIV infection involving administration of at least one anti-retroviral agents (e.g., one, two, three or four anti-retroviral agents) to an HIV infected individual during a course of treatment. Non-limiting examples of antiretroviral agents include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon). One example of an ART regimen includes treatment with a combination of tenofovir, emtricitabine and efavirenz. In some examples, ART includes Highly Active Anti-Retroviral Therapy (HAART). One example of a HAART regimen includes treatment with a combination of tenofovir, emtricitabine and efavirenz.

Biological sample: A sample obtained from a subject. Biological samples include all clinical samples useful for detection of disease or infection (for example, HIV-1) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having a cartilage disorder; for example, a subject having or suspected of having severe short stature.

Bispecific (or multispecific) fusion protein: Proteins that have at least two domains fused together, each domain comprising a binding region capable of forming a specific complex with a target protein. In general, the two domains are genetically fused together, in that nucleic acid molecules that encode each protein domain are functionally linked together, for instance by a linker oligonucleotide, thereby producing a single fusion-encoding nucleic acid molecule. The translated product of such a fusion-encoding nucleic acid molecule is the bispecific fusion protein.

The two binding regions of a bispecific protein may associate with two different binding determinants or epitopes on a single target molecule. One binding domain may bind first to such a target and thereby induce a conformational change in the target such that the binding of the second binding domain to the target is enabled, facilitated, or otherwise increased in affinity. In such an instance, the domain that binds first to the target can be referred to as the inducing-binding domain, while the domain that binds second is the induced-binding domain. These fusion protein domains need not be organized in binding sequence; the amino-proximal binding domain of the fusion protein may be either the induced-binding or the inducing-binding domain; likewise for the carboxy-proximal binding domain.

Multispecific fusion proteins can be further labeled according to the target protein they bind to and neutralize. For instance, a multispecific fusion protein according to the current disclosure that binds to two specific sites on HIV gp120 protein may be referred to as a gp120-targeted bispecific fusion protein.

CD4: Cluster of differentiation factor 4 polypeptide, a T-cell surface protein that mediates interaction with the MHC class II molecule. CD4 also serves as the primary receptor site for HIV on T-cells during HIV infection. The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell* 42:93, 1985).

The term "CD4" includes polypeptide molecules that are derived from CD4 including fragments of CD4, generated either by chemical (e.g. enzymatic) digestion or genetic engineering means. Such a fragment may be one or more entire CD4 protein domains (for example, extracellular domains D1, D2, D3, and D4; see Sakihama et al., *Proc. Natl. Acad. Sci.* 92:6444, 1995; U.S. Pat. No. 6,117,655), as defined in the immunological literature, or a portion of one or more of these well-defined domains. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (CD4 D1D2), though smaller fragments may also provide specific and functional CD4-like binding. The gp120-binding site has been mapped to D1 of CD4, specifically amino acids 1 to 183.

The term "CD4-derived molecules" also encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles, that maintain the ability to functionally bind to a target molecule.

CD4-induced conformational change: A change induced in the three-dimensional conformation of the interacting gp120 protein when CD4 specifically interacts with gp120 to form a complex. One characteristic of such a change is the exposure of at least one induced epitope on the interacting gp120 molecule. An epitope induced by such a change is called a CD4-induced epitope. Such a CD4-induced epitope may for instance include gp120 epitopes at or near the co-receptor-binding region of the protein.

In addition to CD4 binding, the binding of other molecules may induce the exposure of induced epitopes on gp120. Such other inducing molecules are considered CD4-like in terms of their epitope-inducing ability, to the extent that they expose epitopes congruent with or equivalent to those induced epitopes exposed upon the binding of native CD4. These other inducing molecules include, but in no way are limited to, fragments of CD4, for instance sCD4, or a fragment containing the D1 or D1 and D2 domains of native CD4. A mannose-specific lectin may also serve to expose a CD4-induced epitope (see U.S. Pat. No. 5,843,454), as can certain anti-gp120 MAbs.

Chimeric antigen receptor (CAR): A chimeric fusion protein having an extracellular domain that is fused via a transmembrane domain to an intracellular signaling domain capable of activating a T cell. The CAR molecules disclosed herein include an extracellular domain (ectodomain) with two (or more) targeting domains that are functionally different from each other (multispecific CAR) and that bind to two different sites on a target (multi-targeted). For example, one targeting domain of a multispecific CAR can be a cell surface receptor, such as CD4 (i.e., a multispecific CD4-based CAR). In another example, one targeting domain of a multispecific CAR can be a cell surface receptor, such as CD4, and the second targeting domain can be an antibody or a fragment thereof, such as a scFv (i.e. a multispecific CD4-scFv CAR). In some embodiments, the CD4-scFv CAR binds two different target sites (i.e. a multi-targeted CD4-scFv). A monofunctional CAR contains only a single functional element in the targeting extracellular domain. In some particular embodiments, a portion of the CAR's extracellular binding domain is derived from a murine or humanized monoclonal antibody.

The intracellular signaling domain of the CAR molecules disclosed herein includes two different cytoplasmic signaling domains. For example, one signaling domain can be a cytoplasmic effector function signaling domain and the second signaling domain can be a cytoplasmic co-stimulatory signaling domain. Linkers can connect domains to each other (for example, the two targeting domains) or they can connect one domain to another domain (for example, the ligand-binding domain to the transmembrane domain). CARs are also known as chimeric immune receptors, zetakines, and universal T cell receptors.

Chimeric Antigen Receptor (CAR): An engineered T cell receptor having an extracellular antibody-derived targeting domain (such as a scFv) joined to one or more intracellular signaling domains of a T cell receptor. A "chimeric antigen receptor T cell" is a T cell expressing a CAR, and has antigen specificity determined by the antibody-derived targeting domain of the CAR. Methods of making CARs are available (see, e.g., Park et al., *Trends Biotechnol.*, 29:550-557, 2011; Grupp et al., *N Engl J Med.*, 368:1509-1518, 2013; Han et al., *J. Hematol Oncol.*, 6:47, 2013; PCT Pubs. WO 2012/079000, WO 2013/059593; and U.S. Pub. 2012/0213783, each of which is incorporated by reference herein in its entirety.)

Complex (complexed): Two proteins, or fragments or derivatives thereof, are said to form a complex when they measurably associate with each other in a specific manner. Such association can be measured in any of various ways, both direct and indirect. Direct methods may include co-migration in non-denaturing fractionation conditions, for instance. Indirect measurements of association will depend on secondary effects caused by the association of the two proteins or protein domains. For instance, the formation of a complex between a protein and an antibody may be demonstrated by the antibody-specific inhibition of some function of the target protein. In the case of gp120, the formation of a complex between gp120 and a neutralizing antibody to this protein can be measured by determining the degree to which the antibody inhibits gp120-dependent cell fusion or HIV infectivity. Cell fusion inhibition and infectivity assays are discussed further below.

Conditions sufficient to form an immune complex: Conditions which allow an antibody or antigen binding fragment thereof to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Harlow & Lane, infra, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient not infected with HIV. In other embodiments, the control is a positive control, such as a tissue sample obtained from a patient diagnosed with HIV infection. In still other embodiments, the control is a historical control or standard reference value or range of values (such as a previously tested control sample, such as a group of HIV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionuclides (such as $^{35}S$ or $^{131}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance. Methods for using detectable markers and guidance in the choice of detectable markers appropriate for various purposes are discussed for example in Sambrook et al. (Molecular Cloning: A Laboratory Manual, $4^{th}$ ed, Cold Spring Harbor, N.Y., 2012) and Ausubel et al. (In Current Protocols in Molecular Biology, John Wiley & Sons, New York, through supplement 104, 2013).

Detecting: To identify the existence, presence, or fact of something. General methods of detecting are known to the skilled artisan and may be supplemented with the protocols and reagents disclosed herein.

Domain: A discrete structural unit that has its own function.

Effector function: Cell function that has an effect. For example, the engagement of a particular antibody with an Fc receptor on a particular cell triggers an effector function of that cell; phagocytes will phagocytose, mast cells and neutrophils will degranulate, natural killer cells will release cytokines and cytotoxic molecules; that will ultimately result in destruction of the invading microbe. In another example, antibodies coating a pathogen stimulate effector functions against the pathogen in cells that recognize the Fc region of the antibody.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples a disclosed antibody specifically binds to an epitope on HIV-1 Env.

Expressed: Translation of a nucleic acid into a protein. Proteins may be expressed and remain intracellular, become a component of the cell surface membrane, or be secreted into the extracellular matrix or medium.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

Exposing an induced epitope: The process by which two proteins interact specifically to form a complex (an inducing complex), thereby causing a conformational change in at least one of the two proteins (the target protein) such that at least one previously poorly accessible epitope (an induced epitope) is made accessible to intramolecular interaction. The formation of such an inducing complex will generally cause the exposure of more than one induced epitope, each of which may be thereby rendered accessible for intramolecular interaction.

HIV coreceptor: A cell-surface protein other than CD4 involved in the interaction of HIV virus and its subsequent entry into a target cell. These proteins may also be referred to as fusion coreceptors for HIV. Examples of such coreceptor proteins include, for instance, members of the chemokine receptor family (e.g. CXCR4, CCR5, CCR3, and CCR2B).

HIV coreceptor proteins interact with coreceptor binding determinants of gp120. In general, it is believed that some of these determinants are exposed on gp120 only after the specific interaction of gp120 with CD4, and the consequent CD4-induced conformational change in the interacting gp120. Thus certain HIV coreceptor binding determinants are, or overlap with, CD4-induced epitopes.

Neutralization of gp120 can be achieved by the specific binding of neutralizing proteins or protein fragments or domains to one or more coreceptor binding determinants of gp120, thereby blocking interaction between complexed gp120 and the native coreceptor.

HIV neutralizing ability: The measurable ability of a molecule to inhibit infectivity of HIV virus, either in vivo or in vitro. The art is replete with methods for measuring the neutralizing ability of various molecules. Techniques include in vitro peripheral blood mononuclear cell (PBMC) based assays (D'Souza et al., 1997); measurement of virion attachment (Mondor et al., *J. Virol.* 72:3623-3634, 1998); neutral red dye uptake and antigen capture assays (U.S. Pat. No. 5,695,927); vaccinia-based reporter gene cell fusion assay (Nussbaum et al., *J. Virol.* 68:5411-5422, 1994) (standard and sCD4 activated assays); productive infection assays (measuring gag antigen p24 or RT synthesis) (Karn, *HIV: a practical approach*. Oxford Univ. Press, Cambridge, 1995); and infectivity titer reduction assays (Karn, 1995).

In addition, physical interaction between gp120 and CD4 or other CD4-like molecules can be examined by various methods. See, for instance U.S. Pat. No. 5,843,454 (measuring conformational changes of gp120 on binding of various proteins by virus release and susceptibility of gp120 to thrombin-mediated cleavage of the V3 loop). Alternately, the ability of the CD4-like molecule to compete for binding to gp120 with either native CD4 or antibody that recognizes the CD4 binding site on gp120 (CD4BS) can be measured. This will allow the calculation of relative binding affinities through standard techniques.

The disclosure also includes analogs, derivatives or mimetics of the components of the disclosed CAR proteins, and which have HIV neutralizing ability. Such molecules can be screened for HIV neutralizing ability by assaying a protein similar to the disclosed fusion protein, in that it has one or more conservative amino acid substitutions, or analogs, derivatives or mimetics thereof, and determining whether the similar protein, analog, derivative or mimetic provides HIV neutralization. The HIV neutralization ability and gp120 binding affinity of these derivative compounds can be measured by any known means, including those discussed in this application.

Human Immunodeficiency Virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV).

HIV Envelope protein (Env): The HIV envelope protein is initially synthesized as a precursor protein of 845-870 amino acids in size, designated gp160. Individual gp160 polypeptides form a homotrimer and undergo glycosylation within the Golgi apparatus as well as processing to remove the signal peptide, and cleavage by a cellular protease between approximately positions 511/512 to generate separate gp120 and gp41 polypeptide chains, which remain associated as gp120/gp41 promoters within the homotrimer. The ectodomain (that is, the extracellular portion) of the HIV-1 Env trimer undergoes several structural rearrangements from a prefusion mature (cleaved) closed conformation that evades antibody recognition, through intermediate conformations that bind to receptors CD4 and co-receptor (either CCR5 or CXCR4), to a postfusion conformation.

Mature gp120 includes approximated HIV-1 Env residues 31-511, contains most of the external, surface-exposed, domains of the HIV-1 Env trimer, and it is gp120 which binds both to cellular CD4 receptors and to cellular chemokine receptors (such as CCR5). A mature gp120 polypeptide is an extracellular polypeptide that interacts with the gp41 ectodomain to form an HIV-1 Env protomer that trimerizes to form the HIV-1 Env trimer.

The numbering used in HIV-1 Env proteins and fragments thereof is relative to the HXB2 numbering scheme as set forth in Numbering Positions in HIV Relative to HXB2CG Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex., which is incorporated by reference herein in its entirety.

Immune complex: The binding of antibody or antigen binding fragment (such as a scFv) to a soluble antigen forms an immune complex. The formation of an immune complex can be detected through conventional methods known to the skilled artisan, for instance immunohistochemistry, immunoprecipitation, flow cytometry, immunofluorescence microscopy, ELISA, immunoblotting (for example, Western blot), magnetic resonance imaging, CT scans, X-ray and affinity chromatography. Immunological binding properties of selected antibodies may be quantified using methods well known in the art.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Injectable composition: A fluid composition comprising at least one active ingredient, e.g. a cell expressing a CAR disclosed herein. The active ingredient is usually suspended in an acceptable carrier, and the composition can additionally comprise minor amounts of one or more non-toxic auxiliary substances, such as preservatives, pH buffering agents and the like. Such injectable compositions that are useful for use with the CARs disclosed herein are conventional; formulations are well known in the art.

Isolated: An "isolated" biological component (such as a nucleic acid molecule, protein, cell, or organelle) is one that has been substantially separated or purified away from other biological components in the cell of the organism in which the component naturally occurs, i.e., other chromosomal and extra-chromosomal DNA and RNA, proteins, cells, and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Lectin: Carbohydrate-binding proteins; macromolecules that are highly specific for sugar moieties. Lectins perform recognition on the cellular and molecular level and play numerous roles in biological recognition phenomena involving cells, carbohydrates, and proteins. Lectins also mediate attachment and binding of bacteria and viruses, as well as, mediate the first-line defense against invading microorganisms with MBL, the mannan-binding lectin in the innate immune system. It is hypothesized that some hepatitis C viral glycoproteins attach to C-type lectins on the host cell surface (liver cells) for infection.

Carbohydrate recognition domain (CRD): The domain of a lectin protein that mediates binding to a carbohydrate. Lectins can be classified by their type of CRD: c-type (requires $Ca^{2+}$ to activate binding; exemplified by mannose-binding protein (MBP)); p-type (recognize a phosphorylated saccharide, such as mannose-6-phosphate); and I-type (contain an immunoglobulin-like domain; exemplified by sialoadhesin, which binds to sialic acid; SIGLECs). An alternative classification divides lectins into those having c- and s-domains; the c-lectin domain is a carbohydrate binding domain that contains a number of invariant cysteine residues in disulfide bonds and requires calcium ions for binding, while the S-lectin domain contains cysteine residues as free thiols and does not require divalent cations for binding (Drickamer et al., *J. Biol. Chem*, 23:9557-9560, 1988).

Linker: A peptide, usually between two and 150 amino acid residues in length that serves to join two protein domains in a multi-domain fusion protein, such as the CAR molecules disclosed herein. Examples of specific linkers can be found, for instance, in Hennecke et al. (*Protein Eng.* 11:405-410, 1998); and U.S. Pat. Nos. 5,767,260 and 5,856,456.

Depending on the domains being joined, and their eventual function in the fusion protein, linkers may be from about two to about 150 amino acids in length, though these limits are given as general guidance only.

Linkers may be repetitive or non-repetitive. One classical repetitive linker used in the production of single chain Fvs (scFvs) is the $(Gly_4Ser)_3$ (or (GGGGS, residues 372-376 of SEQ ID NO: 5)$_3$ or $(G_4S)_3$) linker. Non-repetitive linkers also have been produced, and methods for the random generation of such linkers are known (Hennecke et al., *Protein Eng.* 11:405-410, 1998). In addition, linkers may be chosen to have more or less secondary character (e.g. helical character, U.S. Pat. No. 5,637,481) depending on the conformation desired in the final fusion protein. The more secondary character a linker possesses, the more constrained the structure of the final fusion protein will be. Therefore, substantially flexible linkers that are substantially lacking in secondary structure allow flexion of the fusion protein at the linker.

Motif: Short, conserved regions that are the most conserved regions of a domain. Motifs are critical for the activity of the domain.

Neutralizing antibodies: An antibody that is able to specifically bind to a target protein in such a way as to inhibit the subsequent biological functioning of that target protein is said to be neutralizing of that biological function. In general, any protein that can perform this type of specific blocking activity is considered a neutralizing protein; antibodies are therefore a specific class of neutralizing protein. The complex formed by binding of a neutralizing protein to a target protein is called a neutralizing complex. In some examples, an antibody that is specific for HIV-1 Env neutralizes the infectious titer of HIV. A "broadly neutralizing antibody" is an antibody that binds to and inhibits the function of related antigens, such as antigens that share at least 85%, 90%, 95%, 96%, 97%, 98% or 99% identity antigenic surface of antigen. With regard to an antigen from a pathogen, such as a virus, the antibody can bind to and inhibit the function of an antigen from more than one class and/or subclass of the pathogen.

Antibodies that bind to viruses and bacteria and thereby prevent the binding of these pathogens to target host cells are said to neutralize the pathogen. Therefore, antibodies that bind to HIV proteins and measurably reduce the ability of the virus to bind to or enter target cells (e.g., T-cells or macrophages) are HIV-neutralizing antibodies. In general, HIV neutralizing antibodies can be broken down into several different classes dependent on what region of the viral envelope protein the antibody binds to. Broad classes of such antibodies include anti-gp120 antibodies. There are several antigenic regions on the gp120 protein that provide epitopes for the natural or laboratory generation of HIV neutralizing antibodies (see WO 98/36087). Broadly cross-reactive neutralizing antibodies usually interact with relatively invariant regions of Env.

A primary source of neutralizing antibodies is the peripheral blood of patients infected with the HIV virus. Such primary isolates can be cloned and/or immortalized using standard techniques. In addition to the isolation of naturally-occurring neutralizing antibodies, procedures specifically directed toward their production are known in the art. See U.S. Pat. Nos. 5,843,454; 5,695,927; 5,643,756; and 5,013,548 for instance.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Oligonucleotide: A linear polynucleotide sequence of between six and 300 nucleotide bases in length.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

ORF (open reading frame): A series of nucleotide triplets (codons) coding for amino acids without any internal termination codons. These sequences are usually translatable into a peptide.

Parenteral: Administered outside of the intestine, e.g., not via the alimentary tract. Generally, parenteral formulations are those that will be administered through any possible mode except ingestion. This term especially refers to injections, whether administered intravenously, intrathecally, intramuscularly, intraperitoneally, or subcutaneously, and various surface applications including intranasal, intradermal, and topical application, for instance.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed antibodies.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended in a unit dosage form containing one or more measured doses of the composition suitable to induce the desired anti-HIV immune response. It may also be accompanied by medications for its use for treatment purposes. The unit dosage form may be, for example, in a sealed vial that contains sterile contents or a syringe for injection into a subject.

Polypeptide: A polymer in which the monomers are amino acid residues that are joined together through amide bonds. When the amino acids are alpha-amino acids, either the L-optical isomer or the D-optical isomer can be used, the L-isomers being preferred in nature. The term polypeptide or protein as used herein encompasses any amino acid sequence and includes, but may not be limited to, modified sequences such as glycoproteins or amidated proteins. The term polypeptide is specifically intended to cover naturally occurring proteins, as well as those that are recombinantly or synthetically produced.

Substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl.

Variant amino acid sequences may, for example, be 80, 90 or even 95 or 98% identical to the native amino acid sequence. Programs and algorithms for determining percentage identity can be found at the NCBI website.

Polypeptide modifications: Polypeptides can be modified by a variety of chemical techniques to produce derivatives having essentially the same activity and conformation as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups.

Purified: The term purified does not require absolute purity; rather, it is intended as a relative term. Thus, for example, a purified fusion protein preparation is one in which the fusion protein is more enriched than the protein is in its generative environment, for instance within a cell or in a biochemical reaction chamber. In some embodiments, a preparation of fusion protein is purified such that the fusion protein represents at least 50% of the total protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is a protein encoded by a heterologous, non-naturally occurring (for example, recombinant) nucleic acid that has been introduced into a host cell, such as a bacterial or eukaryotic cell. The nucleic acid can be introduced, for example, on an expression vector having signals capable of expressing the recombinant protein encoded by the introduced nucleic acid or the nucleic acid can be integrated into the host cell chromosome. A recombinant cell includes a recombinant nucleic acid molecule or protein.

Sequence identity: The similarity between two nucleic acid sequences, or two amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs of the CAR protein will possess a relatively high degree of sequence identity when aligned using standard methods.

Methods of alignment of sequences for comparison are well known in the art. Various programs and alignment algorithms are described in: Smith and Waterman (Adv. Appl. Math. 2: 482, 1981); Needleman and Wunsch (J. Mol. Biol. 48: 443-453, 1970); Pearson and Lipman (Proc. Natl. Acad. Sci., USA 85:2444-2448, 1988); Higgins and Sharp (Gene, 73:237-244, 1988); Higgins and Sharp (CABIOS 5:151-153, 1989); Corpet et al. (Nuc. Acids Res. 16: 10881-10890, 1988); Huang et al. (Comp. Appls. Biosci. 8:155-165, 1992); and Pearson et al. (Methods in Molecular Biology 24: 307-331, 1994). Altschul et al. (Nature Genet., 6:119-129, 1994) presents a detailed consideration of sequence alignment methods and homology calculations.

The alignment tools ALIGN (Myers and Miller, CABIOS 4:11-17, 1989) or LFASTA (Pearson and Lipman, Proc. Natl. Acad. Sci., USA 85:2444-2448, 1988) may be used to perform sequence comparisons (Internet Program © 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet.

Orthologs of the disclosed CAR proteins are typically characterized by possession of greater than 75% sequence identity counted over the full-length alignment with the amino acid sequence of the CAR protein using ALIGN set to default parameters.

The NCBI Basic Local Alignment Search Tool (BLAST) (Altschul et al., *J Mol Biol.* 1990 215:403-410, 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI BLAST website. A description of how to determine sequence identity using this program is also available at the NCBI website BLAST tutorial.

For comparisons of amino acid sequences of greater than about 30 amino acids, the "Blast 2 sequences" function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 90%, at least 92%, at least 94%, at least 95%, at least 97%, at least 98%, or at least 99% sequence identity. In addition, sequence identity can be compared over the full length of one or both binding domains of the disclosed fusion proteins. In such an instance, percentage identities will be essentially similar to those discussed for full-length sequence identity.

When significantly less than the entire sequence is being compared for sequence identity, homologs will typically possess at least 80% sequence identity over short windows of 10-20 amino acids, and may possess sequence identities of at least 85%, at least 90%, at least 95%, or at least 99% depending on their similarity to the reference sequence. Sequence identity over such short windows can be determined using LFASTA; methods are described on the Internet. One of skill in the art will appreciate that these sequence identity ranges are provided for guidance only; it is entirely possible that strongly significant homologs could be obtained that fall outside of the ranges provided. The present disclosure provides not only the peptide homologs that are described above, but also nucleic acid molecules that encode such homologs.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found in Sambrook et al. (In *Molecular Cloning: A Laboratory Manual*, Cold Spring Harbor, N.Y., 1989) and Tijssen (*Laboratory Techniques in Biochemistry and Molecular Biology* Part I, Ch. 2, Elsevier, New York, 1993). Nucleic acid molecules that hybridize under stringent conditions to the disclosed CAR protein sequences will typically hybridize to a probe based on either the entire fusion protein encoding sequence, an entire binding domain, or other selected portions of the encoding sequence under wash conditions of 0.2×SSC, 0.1% SDS at 65° C.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences, each encoding substantially the same protein.

Specific binding agent: An agent that binds substantially only to a defined target. Thus a gp120-specific binding agent binds substantially only the gp120 protein. As used herein, the term "gp120-specific binding agent" includes anti-gp120 antibodies and other agents that bind substantially only to a gp120 protein.

Anti-gp120 antibodies may be produced using standard procedures described in a number of texts, including Harlow and Lane (*Using Antibodies, A Laboratory Manual*, CSHL, New York, 1999, ISBN 0-87969-544-7). In addition, certain techniques may enhance the production of neutralizing antibodies (U.S. Pat. Nos. 5,843,454; 5,695,927; 5,643,756; and 5,013,548). The determination that a particular agent binds substantially only to gp120 protein may readily be made by using or adapting routine procedures. One suitable in vitro assay makes use of the Western blotting procedure (described in many standard texts, including Harlow and Lane, 1999). Western blotting may be used to determine that a given protein binding agent, such as an anti-gp120 monoclonal antibody, binds substantially only to the MSG protein. Antibodies to gp120 are well known in the art.

Shorter fragments of antibodies can also serve as specific binding agents. For instance, FAbs, Fvs, and single-chain Fvs (scFvs) that bind to gp120 would be gp120-specific binding agents.

Subject: Living multi-cellular vertebrate organisms, a category that includes human and non-human mammals. In an example, a subject is a human.

In an additional example, a subject is selected that is in need of inhibiting of an HIV-1 infection. For example, the subject is either uninfected and at risk of HIV-1 infection or is infected in need of treatment.

T Cell: A white blood cell critical to the immune response. T cells include, but are not limited to, $CD4^+$ T cells and $CD8^+$ T cells. A $CD4^+$ T lymphocyte is an immune cell that expresses CD4 on its surface. These cells, also known as helper T cells, help orchestrate the immune response, including antibody responses as well as killer T cell responses. Th1 and Th2 cells are functional subsets of helper T cells. Th1 cells secrete a set of cytokines, including interferon-gamma, and whose principal function is to stimulate phagocyte-mediated defense against infections, especially related to intracellular microbes. Th2 cells secrete a set of cytokines, including interleukin (IL)-4 and IL-5, and whose principal functions are to stimulate IgE and eosinophil/mast cell-mediated immune reactions and to downregulate Th1 responses.

T lymphocyte effector function: Requires two biochemically distinct signals delivered through engagement of unique cell surface membrane receptors, usually one delivered through the T cell's specific antigen receptor (TCR) and the other via a co-stimulatory receptor. Engagement of the co-stimulatory molecule together with the TCR is necessary for optimal levels of cytokine production, such as IL-2, proliferation and clonal expansion, and generation of effector functions such as the production of immunoregulatory cytokines, induction of antibody responses from B cells, and induction of cytolytic activity. More importantly, engagement of the TCR in the absence of the co-stimulatory signal results in a state of non-responsiveness, called anergy. Anergic cells fail to become activated upon subsequent stimulation through the TCR, even in the presence of co-stimulation, and in some cases may be induced to die by a programmed self-destruct mechanism.

Therapeutic agent: Used in a generic sense, it includes treating agents, prophylactic agents, and replacement agents. A therapeutic agent is used to ameliorate a specific set of conditions in a subject with a disease or a disorder.

Therapeutically effective amount of a cell expressing CAR: A quantity of cells expressing a CAR protein sufficient to achieve a desired effect in a subject being treated. For instance, this can be the amount necessary to kill a cell infected with virus, to inhibit viral proliferation, or to measurably neutralize disease organism binding mechanisms. In general, this amount will be sufficient to measurably inhibit virus (e.g. HIV) replication or infectivity.

An effective amount of CAR-expressing cells may be administered in a single dose, or in several doses, for example daily, during a course of treatment. However, the effective amount of the CAR-expressing cells will be dependent on the cells and/or the CAR, the subject being treated, the severity and type of the affliction, and the manner of administration. For example, a therapeutically effective amount of a CAR-expressing cell can vary from about 0.01 mg/kg body weight to about 1 g/kg body weight. In another embodiment, a therapeutically effective amount of a CAR-expressing cell can vary from about $0.1 \times 10^8$ cells to about $100 \times 10^8$ cells per administration.

The CAR-expressing cells disclosed in the present disclosure have equal application in medical and veterinary settings. Therefore, the general term "subject being treated" is understood to include all animals (e.g. humans, apes, dogs, cats, horses, and cows) that are or may be infected with a virus or other disease-causing microorganism that is susceptible to treatment with the cells.

Transformed: A transformed cell is a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Under conditions sufficient for: A phrase that is used to describe any environment that permits a desired activity. In one example the desired activity is formation of an immune complex. In particular examples the desired activity is treatment or inhibition of HIV-1 infection.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

III. Overview of Several Embodiments

Provided herein in a first embodiment is a multispecific chimeric antigen receptor protein comprises an N-terminal extracellular targeting segment comprising a first targeting domain comprising a CD4 derived domain (for instance, the D1 or D1D2 segment of CD4) that binds to HIV Env, and a second targeting domain comprising a carbohydrate recognition domain (CRD) derived from a human C-type lectin that binds to HIV Env. In examples of such a protein, the carbohydrate recognition domain is derived from L-SIGN, DC-SIGN, Langerin or MBL2. The first and second targeting domains bind to different sites on HIV Env, and the multispecific chimeric antigen receptor protein binds to HIV Env. In some embodiments, the multispecific chimeric antigen receptor comprises a linker connecting the first targeting domain to the second targeting domain. In additional embodiments, the CD4 derived domain and the carbohydrate recognition domain (CRD) of the multispecific chimeric antigen receptor protein bind to different sites on HIV Env. In additional embodiments, the multispecific chimeric antigen receptor protein further comprises a linker connecting the extracellular targeting moiety to a transmembrane domain, the transmembrane domain, a cytoplasmic co-stimulatory signaling domain, and a cytoplasmic effector function signaling domain.

In examples of the provided multispecific chimeric antigen receptor proteins, the targeting segment optionally further comprises a linker connecting the CD4 derived domain to the CRD.

In examples of the provided multispecific chimeric antigen receptor proteins, the transmembrane domain is from CD28; and/or the cytoplasmic co-stimulatory signaling domain is from CD28; and/or the cytoplasmic effector function signaling domain is from CD3 zeta.

Specific example multispecific chimeric antigen receptor proteins provided herein comprise the sequence provided in SEQ ID NO: 47 (CD4-DCSIGN CAR ectodomain), SEQ ID NO: 49 (CD4-LSIGN CAR ectodomain), SEQ ID NO: 51 (CD4-Langerin CAR ectodomain), or SEQ ID NO: 53 (CD4-MBL2 CAR ectodomain), or a sequence at least 80% identical to one of these ectodomains.

Also provided herein are multispecific chimeric antigen receptor proteins that are expressed on a cell (such as a T cell) bearing a CD4 and/or a CD8 receptor. An additional embodiment is a method of administering such a multispecific chimeric antigen receptor protein to a subject, wherein the cell bearing the CD4 and/or CD8 receptor is found naturally in that subject.

Also provided are methods of administering any of these multispecific chimeric antigen receptor proteins to a subject, for instance concurrent with or after administration of an antiviral drug to the subject. In yet another embodiment of this administration method, the multispecific chimeric antigen receptor protein is administered to the subject indirectly by administering to the subject or a cell from the subject a heterologous nucleic acid molecule encoding the recombinant protein.

In another embodiment, there is provided a multispecific chimeric antigen receptor protein comprises an N-terminal extracellular targeting segment comprising a first targeting domain comprising a CD4 derived domain that binds to gp120, and a second targeting domain comprising a scFv or derivative thereof that specifically binds to a CD4-induced epitope of HIV Env (such as scFv17b derived domain) that binds to gp120. The first and second targeting domains of the multispecific chimeric antigen receptor protein bind to different sites on gp120. Additionally, the first targeting domain can be connected to the second targeting domain by a linker that is sufficiently short so that the first and second targeting domains do not bind to the same gp120 protein molecule simultaneously. In additional embodiments, the multispecific chimeric antigen receptor protein further comprises a transmembrane domain, a cytoplasmic co-stimulatory signaling domain, and a cytoplasmic effector function signaling domain. In several embodiments, the linker connecting the first targeting domain to the second targeting domain is no more than 20 amino acids long (for instance, the linker can be about 10 amino acids long).

Specific examples of such multispecific chimeric antigen receptor proteins comprise an amino acid sequence at least 80% identical to the extracellular targeting segment of the amino acid sequence set forth as SEQ ID NO: 7.

In examples of such multispecific chimeric antigen receptor proteins, the transmembrane domain is from CD28; and/or the cytoplasmic co-stimulatory signaling domain is from CD28; and/or the cytoplasmic effector function signaling domain is from CD3 zeta.

Also provided are nucleic acid molecules that encode a multispecific chimeric antigen receptor protein as described herein. By way of non-limiting example, such a nucleic acid molecule may comprise the sequence of SEQ ID NO: 6, SEQ ID NO: 46, SEQ ID NO: 48, SEQ ID NO: 50, or SEQ ID NO: 52, or a sequence at least 80% identical to such nucleic acid sequence. Vectors comprising such nucleic acid molecules are also contemplated and enabled herein, as are recombinant cells expressing such vectors. Such recombinant cells, in various examples, are human cells such as human T cells. Also provided are compositions that comprise at least one such recombinant cell and a carrier.

Another embodiment is a method for binding an effector cell to an HIV-infected cell, the method comprising: introducing a nucleic acid molecule encoding a multispecific chimeric antigen receptor protein as described herein into a host cell under conditions sufficient for expression of the encoded multispecific chimeric antigen receptor protein in the host cell to produce an effector cell; and contacting the effector cell expressing the multispecific chimeric antigen receptor protein with an HIV-infected cell expressing gp120, thereby binding an effector cell to an HIV-infected cell. In examples of this embodiment, the host cell is an immune cell, for instance, a CD8+ T cell. Also contemplated are such methods, wherein the host cell expressing the multispecific chimeric antigen receptor is not susceptible to HIV infection.

Another embodiment is method of killing HIV-infected cells, the method comprising: introducing a nucleic acid molecule encoding a multispecific chimeric antigen receptor protein as described herein into a host cell under conditions sufficient for expression of the encoded multispecific chimeric antigen receptor protein in the host cell; and contacting the host cell expressing the chimeric antigen receptor protein with an HIV-infected cell expressing gp120, thereby killing the HIV-infected cells.

Another method provided herein is a method of reducing the level of HIV infected cells in a subject infected with HIV, comprising administering to the subject a composition comprising a recombinant cell expressing a multispecific CAR protein as described herein, thereby treating the subject infected with HIV. By way of example, in such a method in some instances the recombinant cell in the composition is a T cell that is not susceptible to HIV infection.

Yet another embodiments provides a method of generating a recombinant T cell with reduced susceptibility to HIV infection, the method comprising: introducing a nucleic acid molecule encoding a multispecific chimeric antigen receptor protein into a host T cell under conditions sufficient for expression of the encoded multispecific chimeric antigen receptor protein in the host cell, wherein the multispecific chimeric antigen receptor protein comprises, in the N-terminal to C-terminal order: an extracellular targeting segment comprising at least two different targeting domains that bind to two different targets, wherein the first targeting domain is from CD4 and the second targeting domain is an immunoglobulin or a carbohydrate recognition domain (CRD), and wherein the first targeting domain is separated from the second targeting domain by a linker; a transmembrane domain; a cytoplasmic co-stimulatory signaling domain; and a cytoplasmic effector function signaling domain; contacting the host T cell expressing the encoded chimeric antigen receptor protein with an HIV-infected cell expressing gp120 or with an HIV virus particle; and detecting a reduced level of HIV infection in the host T cell expressing the encoded chimeric antigen receptor protein, compared to a T cell that is not expressing the encoded chimeric receptor protein or that is expressing a monofunctional CD4 chimeric antigen receptor, thereby generating the recombinant T cell with reduced susceptibility to HIV infection.

IV. Chimeric Antigen Receptors

Major efforts are underway to develop strategies that allow for the cessation of antiretroviral therapy without viral rebound in blood and tissues, and consequent immune system demise. One promising approach involves adoptive transfer of autologous T cells genetically modified for targeted killing of HIV-infected cells. The genetic engineering of T cells through the introduction of a CAR allows for generation of antigen- or ligand-targeted T cells. Once expressed by T cells, CARs combine antigen- or ligand-specificity with T cell activation in a single fusion molecule.

Generally, CARs are comprised of an antigen- or ligand-binding targeting segment, a transmembrane domain and an intracellular (cytoplasmic) signaling domain for effector functions resulting in T cell activation after antigen or ligand binding. The CARs disclosed herein have a multispecific targeting segment (having two or more targeting domains) and demonstrate superior activity in killing HIV-1 infected cells and in rendering transduced CD8+ cells less susceptible to HIV-1 infection, compared to CARs with a monofunctional targeting segment (having a single targeting domain, for example a CD4-CAR). The CAR disclosed herein is expressed on cells obtained from a subject (e.g. by transduction of CD8+ T cells from an HIV-infected person) and the resultant genetically modified cells are adoptively transferred back to the subject where they can provide persistent targeted killing of HIV infected cells in the body, including cells that arise upon activation of latently infected cells. CAR-expressing CD8+ T cells recognize target cells in an MHC-independent fashion thereby circumventing the restriction to MHC allotype as well as HIV-mediated down modulation of MHC.

Thus, disclosed herein in a first embodiment are novel chimeric antigen/immune receptor proteins, nucleic acid sequences encoding the receptors, vectors containing the nucleic acid sequences encoding the receptors, and host cells expressing the receptors. In addition, genetically engineered, redirected immune cells and their use for cellular immunotherapy are also disclosed herein. Also disclosed herein are methods of rendering transduced CD8+ cells less susceptible to HIV infection.

Another embodiment provides a novel bifunctional targeting moiety (CD4-CRD) of an anti-HIV CAR, which includes a region of human CD4 capable of binding to HIV gp120, attached by a polypeptide linker to a carbohydrate recognition domain (CRD) of a human of a human lectin known to interact with glycans on Env, particularly gp120. One example CD4-CRD is herein designated CD4-DC-SIGN, comprising the first two extracellular domains of human CD4 linked to the CRD derived from the human C-type lectin called DC-SIGN. DC-SIGN is naturally expressed on mucosal dendritic cells and certain macrophages, where it can bind to the abundant high-mannose glycans displayed on the surface of gp120; this interaction has been proposed to enhance DC transmission of HIV particles to adjacent CD4 T cells, and possibly also to contribute to HIV antigen presentation on DCs. Native DC-SIGN is a homo-tetrameric protein, with each type 2 membrane subunit containing an N-terminal cytoplasmic domain, a transmembrane domain, several extracellular repeat sequences involved in oligomerization, and the C-terminal CRD; this targeting moiety is in turn attached to sequences representing a hinge, a transmembrane domain, and intracellular signaling motifs that provide effector and persistence functions to the transduced T cells. Also contemplated are analogous CARs bearing targeting motifs containing CD4 regions linked to alternative CRDs from other human carbohydrate-binding proteins that interact with glycans on HIV Env, including the closely related DC-SIGNR (high sequence homology to DC-SIGN), mannose-binding protein and langerin (all recognizing high mannose glycans on Env), as well as CRDs of galactose-binding lectins such as galectin-1.

Also contemplated are CARs that use of 2nd or 3rd generation intracellular domains (developed in the cancer field), coupled to the herein described novel CD4-based targeting motif (CD4-CRD). Compared to a "standard" CD4 CAR (that is, one bearing only a CD4 domain as the extracellular component), the CD4-CRD CARs taught herein display enhanced potency for HIV inhibition. In addition, they are completely devoid of the undesired activity observed with "standard" CD4 CARs of rendering the transduced CD8 T cells (which also express coreceptors) susceptible to HIV infection. Moreover, it is believed that the CD4-CRD CARs will be less immunogenic since all components (except linkers) are human-derived and non-variable. This is in contrast to, for instance, a CAR including an antibody fragment as part of the extracellular targeting domain, which may elicit anti-idiotypic antibodies against variable regions of the scFv. This phenomenon has been observed with anti-cancer CARs.

A. Selection of Component Domains.

Disclosed herein is a recombinant multispecific targeting segment for a chimeric antigen receptor (CAR) designed to selectively kill cells infected with HIV-1. Novel CAR/CIRs are provided containing a multispecific targeting segment (multispecific extracellular domain), a transmembrane domain, and a cytoplasmic signaling domain that do not naturally exist together as a single receptor protein.

1. Targeting Domains

The multispecific targeting segment of the CAR contains two or more different targeting domains. In some embodiments, the two or more different targeting domains bind to different sites on a single target protein. Optionally, the targeting domains are separated by a linker or hinge. In some embodiments, one of the targeting domains is a CD4 polypeptide, such as a fragment of CD4 and another is an antibody or the binding domain or other functional fragment thereof. In another embodiment, one of the targeting domains is a CD4 polypeptide, such as a fragment of CD4 and another is a carbohydrate binding domain of a human lectin.

A target protein can be any protein that has a binding site that can be bound by a CAR multispecific targeting segment. In one embodiment, a target protein has a single binding site. In other embodiments, a target protein has two or more different binding sites. In one specific, non-limiting example of a target protein with two binding sites one of the two binding sites is exposed/induced (also referred to as an induced binding site) by the binding of a CAR targeting domain (as referred to as the inducing-binding domain) to a different binding site (the inducing-binding site) on the same target protein (see U.S. Pat. Nos. 7,115,262 and 8,420,099, incorporated herein by reference). The choice of targeting domain for incorporation into the disclosed multispecific targeting segment of the CAR will be dictated by the target protein or proteins chosen. In particular embodiments the target protein is a protein (either completely or partially) exposed on the surface of a cell. Such target proteins include proteins naturally present at the extracellular surface of a cell or proteins which are expressed at the cell surface as a result of genetic engineering or infection by a virus, such as HIV. In some embodiments, the target protein is an HIV envelope glycoprotein, for example HIV-1 gp120 expressed on the surface of an HIV infected cell, such as an infected T cell.

The specific fragments used to construct the multispecific targeting segment of the CAR should be chosen so that the conformation of the targeting segment provides functional binding, or functional and inducing binding to gp120; this can be assayed either directly (e.g., affinity measurements) or indirectly (e.g., neutralization assays).

In some embodiments, the targeting segment may include cell surface receptors as one or more CAR targeting domains, including cluster of differentiation (CD) molecules such as CD4 or CD8, cytokine receptors, or hormone receptors. The cell surface receptor may be responsive to a natural ligand, an antibody or fragment thereof, a synthetic molecule, or any other agent which is capable of inducing a signal.

In certain embodiments, a binding site on the target protein is the CD4 binding site on gp120. As such, the targeting domain of the disclosed multispecific targeting segment can be a particular binding fragment of CD4, for instance soluble CD4 (sCD4) or any fragment that contains the CD4 D1D2 domains. Alternately, any other molecule that specifically interacts with gp120 in such a way as to bind to gp120, or to bind to and expose one or more induced epitopes on gp120, would also serve as a targeting domain.

Non-CD4-derived CD4 mimics may also be employed as targeting domains in the CARs disclosed herein. In particular embodiments, antibodies that bind to the gp120 CD4-binding site or another epitope of gp120, or antibodies that bind to the gp120 CD4-binding site or another epitope of gp120 and induce a CD4-like conformational change on the target protein bound to the CAR, can also be used.

Non-peptide CD4 analogs can also be used as targeting domains in the disclosed multispecific targeting segments, such as an organic or non-organic structural analog of the gp120-interacting domain(s) of the CD4 molecule.

In other embodiments, the targeting segment may include one or more immunoglobulin (Ig) molecules, or portions or modifications thereof, as targeting domains. Specific, non-limiting examples of Ig molecules, or portions or modifications thereof, include a full-length Ig heavy chain, a full-length Ig light chain, a variable heavy chain (VH), a variable light chain (VL), a single chain variable fragment (scFv), or the like. In some embodiments, the Ig is fused to a cytoplasmic signaling domain, such as a co-stimulatory cytoplasmic signaling domain, via a transmembrane domain. Depending on the function of the antibody, the entire chain may be used or a truncated chain may be used, where all or a part of the CH1, CH2 or CH3 domains may be removed or all or part of the hinge region may be removed. Specific, non-limiting examples of Ig molecules directed against gp120 that can be used as a targeting moiety of the disclosed CARs include PG9, PG16, PGT141, PGT142, PGT143, PGT144, PGT145, HGN194, and 2G12 (Walker et al., *Science* 326:285-289, 2009; Walker et al., *Nature* 477:466-470, 2011; Watkins et al., *PLoS ONE* 2011; 6: e18207; Trkola et al., *J Virol* 69:6609-6617, 1995).

scFvs, in which the C-terminus of one variable domain (VH or VL) is joined to the N-terminus of the other (VL or VH, respectively) via a linker, can be synthesized without significantly disrupting antigen binding or the specificity of the binding of the antigen. Thus, in some embodiments of the disclosed CARs, at least one of the targeting domains is a scFv. In particular embodiments, the scFvs may be of two types depending on the relative order of the VH and VL domains: VH-L-VL or VL-L-VH (where "L" represents the linker). These scFvs lack the constant regions (Fc) present in the heavy and light chains of the native antibody. In other embodiments, the scFvs may be fused to all or a portion of the constant domains of the heavy chain. In further embodiments, the multispecific targeting segment is joined to the CAR cytoplasmic domain via an appropriate transmembrane domain. The resulting CARs differ from the scFvs in that upon binding of antigen they initiate signal transduction via the CAR cytoplasmic signaling domain.

In particular embodiments, a targeting domain, such as an induced-binding domain of a gp120-targeted CAR, will include antibodies (or fragments thereof) that recognize induced epitopes of the gp120 molecule bound to a first targeting domain. In some embodiments, such antibodies are broadly cross-reactive against diverse HIV-1 isolates. Induced epitopes include all of those referred to as CD4-induced (CD4i) epitopes, and in particular those which overlap with co-receptor-binding determinants of gp120. Previously identified neutralizing monoclonal antibodies can be used, and include but are not limited to human monoclonal antibodies 17b, 48d, CG10, 412d, X5, 21C, 19e, 47E, E51, 16 c, 23e, 411G, 31H, ED47, and ED49 (Thali et al. *J. Virol* 67:3978-3988, 1993; Gershoni et al. *FASEB J.* 7:1185-1187, 1993; Farzan et al. *J. Virol.* 79:6068-77, 2005; Moulard et al., *PNAS* 99:6913-6918, 2002; Salzwedel et al., *J. Virol.,* 74:326-333, 2000; Reeves et al., *J. Virol.,* 79:4991-4999, 2005; and Nora et al., *Retrovirol.,* 5:1-16, 2008). CG10 is also described in U.S. Pat. No. 6,329,202 and was deposited on Feb. 4, 1993 at the European Collection of Animal Cell Culture (ECACC), Porton Down, Salisbury, Wiltshire, SP4 OJG, United Kingdom.

Thus, in one specific, non-limiting example of a targeting segment, the first targeting domain is an extracellular portion of CD4 that binds to HIV-1 gp120 and is attached by a polypeptide linker to a neutralizing scFv. In other embodiments, targeting domains of the disclosed targeting segments can be non-peptide molecules, for instance organic or non-organic structural analogs of scFv(17b).

In some embodiments, two or more antigen-binding domains from antibodies of different specificities, two or more different ligand-binding domains, or a combination of these domains can be connected to each other by oligo- or polypeptide linkers or hinges to create multispecific targeting segments. These targeting segments can be used to create the disclosed multispecific CARs which will respond to two or more different binding sites on one or more target proteins. In embodiments where the targeting segment contains more than two targeting domains, linkers or hinges may separate all, some, or none of the targeting domains.

Figure 12A:
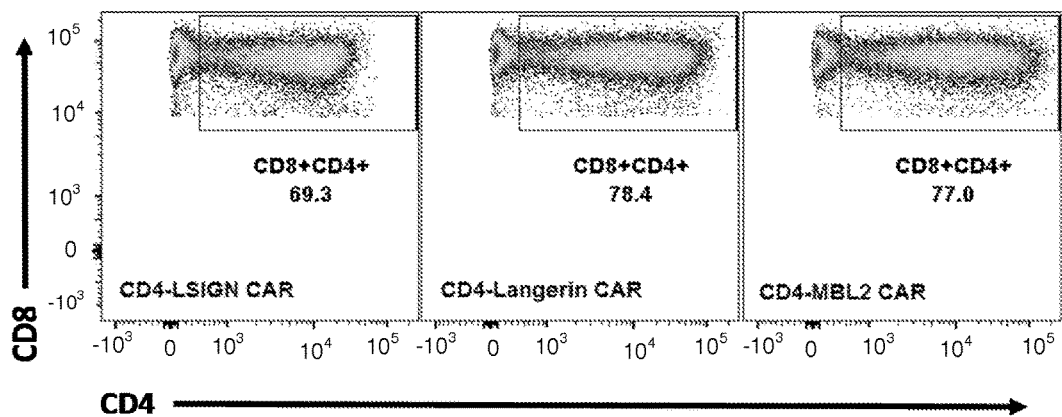
FIG. 12A shows expression of CD4-based CARs with CRDs from other human C-type lectins. Gated on CD8+ cells. CD4-based CAR expression was evaluated by staining for CD8 and CD4.
Figure 12B:
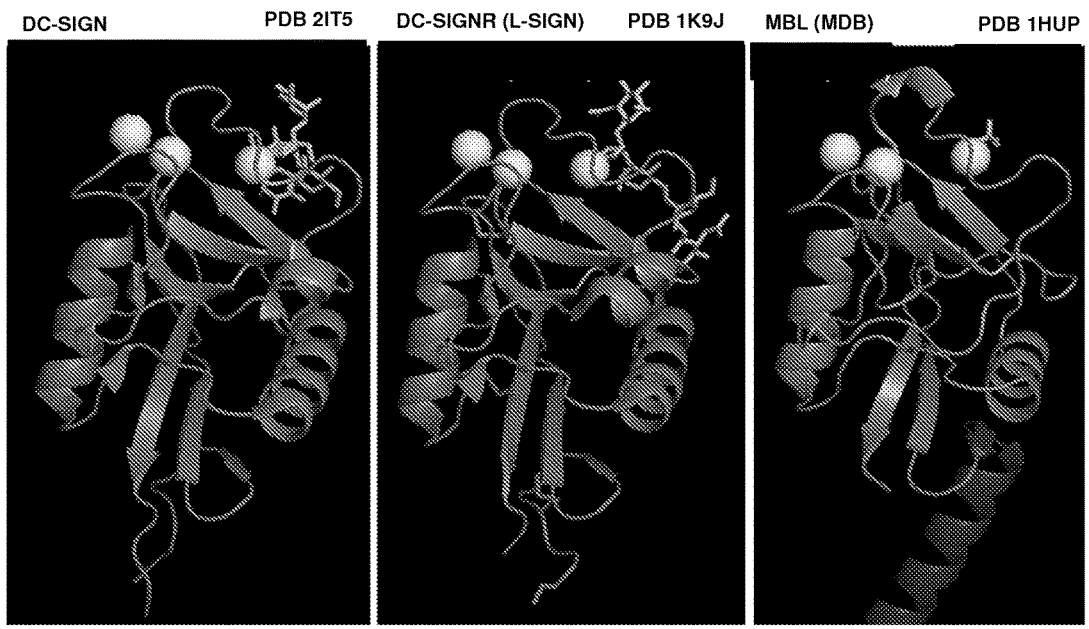
FIG. 12B shows the crystal structures of CRDs of closely related human mannose-binding lectins DC-SIGN, DC-SIGNR, and MBL (PDB Acc. Nos. 2IT5, 1K9J, and 1HUP, respectively).

In certain embodiments, the CAR ectodomain includes a carbohydrate recognition domain (CRD) from a lectin, for instance a human lectin such as a human c-type lectin (CLEC). The human genome encodes a number of lectins with various glycan specificities. Among these are several mannose-binding lectins that have been demonstrated to bind to HIV-1, including DC-SIGN and DC-SIGN's close relative DC-SIGNR (also designated L-SIGN, expressed on endothelial cells), as well as a serum protein called mannose binding lectin (MBL, or MBP), a protein on Langerhans cells called Langerin, etc. Crystal structures have been reported for many of these, and they are closely related as shown in FIG. 12B (also Langerin, not shown). There are subtle differences in the carbohydrate specificities of these lectins, and their reactivities with pathogens and host glycans. Thus, CD4-DCSIGN as demonstrated herein is considered a prototype of this class of CAR targeting moieties; variant CARs with CD4 linked to these other CRDs (e.g., LSIGN, Langerin, MBL2) have also been expressed and examined for functionality herein.

CLEC CRDs such as those from DC-SIGN, LSIGN, Langerin, and MBL2, are modular in nature, have decreased affinity for their ligands in monomeric form, and are principally involved in pathogen binding—all of which makes them suitable for incorporation into a CAR.

The choice of linker or hinge between different targeting domains will also be influenced by the target protein and binding sites chosen. In general, the linker used in any multispecific targeting segment will be of a length short enough to prevent simultaneous binding of multiple targeting domains from the same CAR molecule to binding sites on the same target protein. In some embodiments, the linker is about 10 amino acids long, for example, the linker is about 1 amino acid, 2 amino acids, 3 amino acids, 4 amino acids, 5 amino acids, about 6 amino acids, about 7 amino acids, about 8 amino acids, about 9 amino acids, about 11 amino acids, about 12 amino acids, about 13 amino acids, about 14 amino acids, about 15 amino acids, about 16 amino acids, about 17 amino acids, about 18 amino acids, about 19 amino acids, or about 20 amino acids long.

A targeting domain, such as an antibody-derived extracellular domain, may be connected at its C-terminal end to a membrane hinge region, such as one found on membrane-bound immunoglobulin molecules. In some embodiments, a transmembrane domain is attached to the C-terminal end of the membrane hinge. It is also contemplated that membrane hinge sequences may be used to connect non-antibody derived targeting domains to CAR transmembrane domains.

2. Transmembrane Domain

With respect to the transmembrane domain, the CAR can be designed to comprise a transmembrane domain that is fused to the extracellular domain of the CAR. In one embodiment, the transmembrane domain that naturally is associated with one of the domains in the CAR is used.

The transmembrane domain may be derived either from a natural or from a synthetic source. Where the source is natural, the domain may be derived from any membrane-bound or transmembrane protein. Exemplary transmembrane domains for use in the disclosed CARs can include at least the transmembrane region(s) of) the alpha, beta or zeta chain of the T-cell receptor, CD28, CD3 epsilon, CD45, CD4, CD5, CDS, CD9, CD 16, CD22, CD33, CD37, CD64, CD80, CD86, CD 134, CD137, CD154. Alternatively the transmembrane domain may be synthetic, in which case it will comprise predominantly hydrophobic residues such as leucine and valine. In several embodiments, a triplet of phenylalanine, tryptophan and valine will be found at each end of a synthetic transmembrane domain.

Optionally, a short oligo- or polypeptide linker, preferably between 2 and 10 amino acids in length may form the linkage between the transmembrane domain and the intracellular T cell signaling domain and/or T cell costimulatory domain of the CAR. A exemplary linker sequence includes one or more glycine-serine doublets.

In some embodiments, the transmembrane domain comprises the transmembrane domain of a T cell receptor, such as a CD8 transmembrane domain. Thus, the CAR can include a CD8 transmembrane domain including or consisting of SEQ ID NO: 54:

TTTPAPRPPTPAPTIASQPLSLRPEACRPAAGGAVHTRGLDFACDIYIWA

PLAGTCGVLLLSLVITLYC.

In another embodiment, the transmembrane domain comprises the transmembrane domain of a T cell costimulatory molecule, such as CD137 or CD28. Thus, the CAR can include a CD28 transmembrane domain including or consisting of SEQ ID NO: 55:

IEVMYPPPYLDNEKSNGTIIHVKGKHLCPSPLFPGPSKPFWVLVVVGGVL

ACYSLLVTVAFIIFWVR.

In some embodiments, the transmembrane domain is an extension of the portion of the protein contributing the cytoplasmic domain, an extension of the portion of the protein contributing a targeting domain, or a portion of a completely different protein. In some embodiments, the transmembrane domain is naturally associated with the targeting segment or the cytoplasmic domain. In some embodiments, the transmembrane domain is obtained from the zeta, eta, or FcεR1δ chains or related proteins, or of a co-stimulatory protein, for example CD28 or CTLA-4. In some embodiments, the transmembrane domain will be selected to minimize interactions with other members of a cell surface receptor complex. In other embodiments, it will be desirable to employ the transmembrane domain of zeta, eta, FcεR1 δ1 or the co-stimulatory protein, in order to retain physical association with other cell surface receptors or proteins.

3. Intracellular Region

The intracellular region of the CAR includes one or more intracellular T cell signaling domains responsible for activation of at least one of the normal effector functions of a T cell in which the CAR is expressed or placed in. Exemplary T cell signaling domains are provided herein, and are known to the person of ordinary skill in the art.

While an entire intracellular T cell signaling domain can be employed in a CAR, in many cases it is not necessary to use the entire chain. To the extent that a truncated portion of the intracellular T cell signaling domain is used, such truncated portion may be used in place of the intact chain as long as it transduces the relevant T cell effector function signal.

Examples of intracellular T cell signaling domains for use in the CAR include the cytoplasmic sequences of the T cell receptor (TCR) and co-stimulatory molecules that act in concert to initiate signal transduction following antigen receptor engagement, as well as any derivative or variant of these sequences and any synthetic sequence that has the same functional capability.

T cell receptor signaling domains regulate primary activation of the T cell receptor complex either in a stimulatory way, or in an inhibitory way. The disclosed CARs can include primary cytoplasmic signaling sequences that act in a stimulatory manner, which may contain signaling motifs that are known as immunoreceptor tyrosine-based activation motifs or ITAMs. Examples of ITAM containing primary cytoplasmic signaling sequences that can be included in a disclosed CAR include those from CD3 zeta, FcR gamma, FcR beta, CD3 gamma, CD3 delta, CD3 epsilon, CDS, CD22, CD79a, CD79b, and CD66d proteins. In several embodiments, the cytoplasmic signaling molecule in the CAR includes an intracellular T cell signaling domain from CD3 zeta.

The intracellular region of the CAR can include the ITAM containing primary cytoplasmic signaling domain (such as CD3-zeta) by itself or combined with any other desired cytoplasmic domain(s) useful in the context of a CAR. For example, the cytoplasmic domain of the CAR can include a CD3 zeta chain portion and an intracellular costimulatory signaling domain. The costimulatory signaling domain refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40 (CD134), CD30, CD40, PD-1, ICOS, lymphocyte function-associated antigen 1 (LFA-1), CD2, CD7, LIGHT, NKG2C, and B7-H3. An additional example of a signaling domain that can be included in a disclosed CARs is a Tumor necrosis factor receptor superfamily member 18 (TNFRSF18; also known as glucocorticoid-induced TNFR-related protein, GITR) signaling domain.

In some embodiments, the CAR can include a CD3 zeta signaling domain, a CD8 signaling domain, a CD28 signaling domain, a CD137 signaling domain or a combination of two or more thereof. In one embodiment, the cytoplasmic domain includes the signaling domain of CD3-zeta and the signaling domain of CD28. In another embodiment, the cytoplasmic domain includes the signaling domain of CD3 zeta and the signaling domain of CD137. In yet another embodiment, the cytoplasmic domain includes the signaling domain of CD3-zeta and the signaling domain of CD28 and CD137. The order of the one or more T cell signaling domains on the CAR can be varied as needed by the person of ordinary skill in the art.

Exemplary amino acid sequences for such T cell signaling domains are provided. For example, the CD3 zeta signaling domain can include or consist of the amino acid sequence set forth as SEQ ID NO: 56 (RVKFSRSADAPAYQQGQNQ-LYNELNLGRREEYDVLDKRRGRDPEMGGKPRRKN-PQEGLY NELQKDKMAEAYSEIGMKGERRRGKGH-DGLYQGLSTATKDTYDALHMQALPPR), the CD8 signaling domain can include or consist of the amino acid sequence set forth as SEQ ID NO: 57 (FVPVFLPAKPTTT- PAPRPPTPAPTIASQPLSLRPEACR-PAAGGAVHTRGLDFACDIYIWAPLAGTCGV-LLLSLVITLYCNHRNR), the CD28 signaling domain can include or consist of the amino acid sequence set forth as SEQ ID NO: 58 (SKRSRLLHSDYMNMTPRRPGP-TRKHYQPYAPPRDFAAYRS), the CD137 signaling domain can include or consist of the amino acid sequences set forth as SEQ ID NO: 59 (RFSVVKRGRKKLLY-IFKQPFMRPVQTTQEEDGCSCRFPEEEEGGCEL) or positions 6-47 of SEQ ID NO: 59.

The cytoplasmic signaling sequences within the cytoplasmic signaling portion of the CAR of the invention may be linked to each other in a random or specified order. Optionally, a short polypeptide linker, preferably between 2 and 10 amino acids in length may form the linkage. A glycine-serine doublet provides a particularly suitable linker. Further, between the signaling domain and the transmembrane domain of the CAR, there may be a spacer domain, which includes a polypeptide sequence. The spacer domain may comprise up to 300 amino acids, preferably 10 to 100 amino acids and most preferably 25 to 50 amino acids.

The cytoplasmic domain of the disclosed CAR proteins may be derived from a protein which is known to activate one or more messenger systems or to activate one or more effector functions in a cell. In one specific, non-limiting example, the cytoplasmic domain of the CAR may be derived from a signal transducing molecule. The protein from which the cytoplasmic domain is derived need not have ligand binding capability by itself, it being sufficient that such a protein may associate with another protein providing such capability. In particular embodiments, the cytoplasmic domain is a signal transduction domain from a co-stimulatory molecule. Specific, non-limiting examples of co-stimulatory molecules from which cytoplasmic regions can be obtained include CD28, CTLA-4, CD2, CD5, ICAM-1, Leukocyte Functional Antigen (LFA-1) (CD11a/CD18), or Heat Soluble Antigen (HSA), or other cytoplasmic regions capable of transmitting a co-stimulatory signal as a result of interacting with other proteins that bind to a ligand. In some embodiments, an entire cytoplasmic region will be employed. In other embodiments, variants or a portion of an entire cytoplasmic region, for example functional fragments or mutants thereof, is used. In particular embodiments the functional fragments of a cytoplasmic region may range from about 50 amino acids to about 500 amino acids in length.

In some embodiments, one cytoplasmic domain is linked to a second cytoplasmic domain. In other embodiments, one cytoplasmic domain is linked to two or more other cytoplasmic domains. The cytoplasmic domains can be the same or different. For example, the cytoplasmic domain of a co-stimulatory molecule can be linked to the cytoplasmic domain of one or more of the CD3 chains of the T cell receptor, for example to one or more of the zeta, eta, delta, gamma or epsilon CD3 chains of the T cell receptor. In other embodiments, the cytoplasmic domain of a co-stimulatory molecule a tyrosine kinase, such as a member of the Syk tyrosine kinase family which activates cytolysis, Syk or ZAP-70, where the cytoplasmic domain is capable of activating effector function in a host cell.

In a particular, non-limiting example, the C-terminus of a CD28 receptor is joined to the N-terminal residue of the cytoplasmic domain of CD3 zeta (i.e., linked head-to-tail), resulting in a CAR with targeting (extracellular) and transmembrane segments linked to the cytoplasmic domains of CD3-zeta and CD28. In another specific, non-limiting example of a CAR, a CD4 extracellular domain (CD4 targeting segment) is linked to the cytoplasmic domains of CD3-zeta and CD28 via a transmembrane domain. In yet another specific, non-limiting example of a CAR, a targeting (extracellular) domain containing two targeting domains (CD4 and scFv) is linked to the cytoplasmic domains of CD3-zeta and CD28 via a transmembrane domain. In a further specific, non-limiting example of a CAR, an extracellular domain containing two targeting domains (CD4 and scFv17b) is linked to the cytoplasmic domains of CD3-zeta and CD28 via a transmembrane domain. In some embodiments of the CARs disclosed herein, the cytoplasmic signaling domain is a combined cytoplasmic domain comprising an effector function signaling domain, e.g. zeta, linked to a co-stimulatory signaling domain such as CD28. Thus, binding of the appropriate ligand, e.g. gp120, to an extracellular domain (for example, CD4 or scFv) results in the transduction of both a primary activation signal and a co-stimulatory signal simultaneously, in an MHC-independent manner.

In some embodiments, a cytoplasmic domain is connected to the transmembrane domain by oligo- or polypeptide linkers or hinges. In particular embodiments, two or more cytoplasmic domains can be connected to each other by oligo- or polypeptide linkers or hinges to create a CAR cytoplasmic signaling domain.

B. Chimeric Antigen Receptor Sequence Variants

The binding characteristics and therefore neutralizing activity of the CAR fusion proteins disclosed herein lies not in the precise amino acid sequence, but rather in the three-dimensional structure inherent in the amino acid sequences encoded by the DNA sequences. It is possible to recreate the binding characteristics of any of these proteins or protein domains of this disclosure by recreating the three-dimensional structure, without necessarily recreating the exact amino acid sequence. This can be achieved by designing a nucleic acid sequence that encodes for the three-dimensional structure, but which differs, for instance by reason of the redundancy of the genetic code. Similarly, the DNA sequence may also be varied, while still producing a functional neutralizing protein.

Variant CAR proteins include proteins that differ in amino acid sequence from the disclosed sequence, but that share structurally significant sequence homology with any of the provided proteins. Variation can occur in any single domain of the fusion protein (e.g. the first or second targeting domain, or the linker). Variation can also occur in more than one of such domains in any particular variant CAR protein. Such variants may be produced by manipulating the nucleotide sequence of the CAR protein using standard procedures, including site-directed mutagenesis or PCR. The simplest modifications involve the substitution of one or more amino acids for amino acids having similar biochemical properties. These so-called conservative substitutions are likely to have minimal impact on the activity of the resultant protein, especially when made outside of the binding site of each domain.

Variant binding domain or CAR protein-encoding sequences may be produced by standard DNA mutagenesis techniques, for example, M13 primer mutagenesis. Details of these techniques are provided in Sambrook (In *Molecular Cloning: A Laboratory Manual*, Cold Spring Harbor, N.Y., 1989), Ch. 15. By the use of such techniques, variants may be created which differ in minor ways from the bispecific fusion protein-encoding sequences disclosed. DNA molecules and nucleotide sequences which are derivatives of those specifically disclosed herein and that differ from those disclosed by the deletion, addition, or substitution of nucleotides while still encoding a protein that binds the target protein, are comprehended by this disclosure. In their most simple form, such variants may differ from the disclosed sequences by alteration of the coding region to fit the codon usage bias of the particular organism into which the molecule is to be introduced.

Alternatively, the coding region may be altered by taking advantage of the degeneracy of the genetic code to alter the coding sequence such that, while the nucleotide sequence is substantially altered, it nevertheless encodes a protein having an amino acid sequence substantially similar to the disclosed CAR fusion sequences. Based upon the degeneracy of the genetic code, variant DNA molecules may be derived from the cDNA and gene sequences disclosed herein using standard DNA mutagenesis techniques as described above, or by synthesis of DNA sequences.

The present disclosure includes biologically active molecules that mimic the action of the CAR fusion proteins, or one or more of the domains encompassed therewith, of the present disclosure, and specifically neutralize HIV Env (gp120). The proteins of the disclosure include synthetic embodiments of naturally-occurring proteins described herein, as well as analogues (non-peptide organic molecules), derivatives (chemically functionalized protein molecules obtained starting with the disclosed peptide sequences) and variants (homologs) of the disclosed proteins. Each protein of the disclosure is comprised of a sequence of amino acids, which may be either L- and/or D-amino acids, naturally occurring and otherwise.

Proteins may be modified by a variety of chemical techniques to produce derivatives having essentially the same activity as the unmodified proteins, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the protein, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the protein side chains may be converted to $C_1$-$C_{16}$ alkoxy or to a $C_1$-$C_{16}$ ester using well-recognized techniques. Phenyl and phenolic rings of the protein side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the protein side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the proteins of this disclosure to select and provide conformational constraints to the structure that result in enhanced stability.

It also may be advantageous to introduce one or more disulfide bonds to connect the frameworks of the heavy and light chains in a scFv domain. This modification often enhances the stability and affinity of scFvs (Reiter et al., *Protein Engineering* 7:697-704, 1994). X-ray crystal structure containing the 17 FAb (Kwong et al., *Nature* 393:648-659, 1998) can be used to assess optimal sites for engineering cysteine residues of the heavy and light chains.

Peptidomimetic and organomimetic embodiments are also within the scope of the present disclosure, whereby the three-dimensional arrangement of the chemical constituents of such peptido- and organomimetics mimic the three-dimensional arrangement of the protein backbone and component amino acid side chains in the bispecific neutralizing fusion protein, resulting in such peptido- and organomimetics of the proteins of this disclosure having measurable or enhanced neutralizing ability. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press: Buffalo Grove, Ill., pp. 165-174 and *Principles of Pharmacology* Munson (ed.) 1995, Ch. 102, for descriptions of techniques used in CADD.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, a-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, oc-aminocycloheptane carboxylic acid, -(2-amino-2-norbornane)-carboxylic acid, γ-diaminobutyric acid, α,β-diaminopropionic acid, homophenylalanine, and α-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

It will be appreciated that the protein domains of the current disclosure may be combined to produce fusion protein molecules without necessarily splicing the components in the same place. It is believed to be possible to use shorter or longer fragments of each component domain, linked by a functional linker. For instance, any component which is spliced within about 10 amino acid residues of the residue specified, and which still provides a functional binding fragment, comprises about the same domain. However, domains of substantially longer or substantially shorter length can be used.

C. Assembly.

The construction of chimeric molecules, such as CARs, from domains of known proteins is well known. In general, a nucleic acid molecule that encodes the desired protein domains are joined using standard genetic engineering techniques to create a single, operably linked fusion oligonucleotide. Molecular biological techniques may be found in Sambrook et al. (*In Molecular Cloning: A Laboratory Manual*, Cold Spring Harbor Laboratory Press, New York, 2000). Specific examples of genetically engineered multi-domain proteins, especially those based on molecules of the immunoglobulin superfamily, joined by various linkers, can be found in the following patent documents:

U.S. Pat. No. 5,856,456 ("Linker for linked fusion polypeptides");

U.S. Pat. No. 5,696,237 ("Recombinant antibody-toxin fusion protein");

U.S. Pat. No. 5,767,260 ("Antigen-binding fusion proteins");

U.S. Pat. No. 5,587,455 ("Cytotoxic agent against specific virus infection"); and WO 98/36087 ("Immunological tolerance to HIV epitopes").

Specific examples of CARs can be found in U.S. Pat. No. 5,712,149 ("Chimeric receptor molecules for delivery of co-stimulatory signals") and U.S. Pat. No. 6,103,521 ("Multispecific chimeric receptors").

Non-peptide analogs of the protein domains disclosed herein can be linked to another domain of the chimeric molecules using known chemical linking techniques, including chemical cross-linking. Cross-linkers are well known, and examples of molecules used for cross-linking can be found, for instance, in U.S. Pat. No. 6,027,890 ("Methods and compositions for enhancing sensitivity in the analysis of biological-based assays").

D. Expression.

One skilled in the art will understand that there are myriad ways to express a recombinant protein such that it can be expressed on a cell surface. In general, an expression vector carrying the nucleic acid sequence that encodes the desired protein will be transformed into a microorganism for expression. Such microorganisms can be prokaryotic (bacteria) or eukaryotic (e.g., yeast). One example species of bacteria that can be used is *Escherichia coli* (*E. coli*), which has been used extensively as a laboratory experimental expression system. A eukaryotic expression system can be used where the protein of interest requires eukaryote-specific post-translational modifications such as glycosylation. Also, protein can be expressed using a viral (e.g., vaccinia) based expression system.

Protein can also be expressed in animal cell tissue culture, and such a system can be used where animal-specific protein modifications are desirable or required in the recombinant protein.

The expression vector can include a sequence encoding a signal peptide, positioned in such a way as to be fused to the coding sequence of the CAR molecule. This allows the CAR protein to be targeted to specific membrane or sub-cellular locations. Various prokaryotic and eukaryotic signal peptides, and nucleic acid molecules encoding such, are known. In a prokaryotic expression system, a signal peptide can be used to secrete the newly synthesized protein. In a eukaryotic expression system, the signal peptide would specify targeting of the disclosed CAR to one or more specific sub-cellular compartments, or to be expressed on the surface of the cell, depending on which signal peptide is chosen.

Vectors suitable for stable transformation of cultured cells are also well known. Typically, such vectors include a multiple-cloning site suitable for inserting a cloned nucleic acid molecule, such that it will be under the transcriptional control of 5' and 3' regulatory sequences. In addition, transformation vectors include one or more selectable markers; for bacterial transformation this is often an antibiotic resistance gene. Such transformation vectors typically also contain a promoter regulatory region (e.g., a regulatory region controlling inducible or constitutive expression), a transcription initiation start site, a ribosome binding site, an RNA processing signal, and a transcription termination site, each functionally arranged in relation to the multiple-cloning site.

A wide variety of promoters have been described in the literature, which are constitutive or inducible, where induction may be associated with a specific cell type or a specific level of maturation. For production of large amounts of recombinant proteins, an inducible promoter can be used. This permits selective production of the recombinant protein, and allows both higher levels of production than constitutive promoters, and enables the production of recombinant proteins that may be toxic to the expressing cell if expressed constitutively. Alternatively, any one of a number of viral promoters may be used. Promoters of interest include the .beta.-actin promoter, SV40 early and late promoters, immunoglobulin promoter, human cytomegalovirus promoter, and the Friend spleen focus-forming virus promoter. In some embodiment, enhancers are associated with the promoters. The enhancers may be naturally associated with the particular promoter or associated with a different promoter.

The CAR construct may be introduced into a host cell in any method known in the art, which include calcium phosphate or DEAE-dextran mediated DNA transfection, electroporation, protoplast fusion, liposome fusion, biolistics using DNA-coated particles, transfection, and infection, where the chimeric construct is introduced into an appropriate virus, e.g. retrovirus, adenovirus, adeno-associated virus, Herpes virus, Sindbis virus, papilloma virus, particularly a non-replicative form of the virus, or the like. In addition, direct injection of naked DNA or protein- or lipid-complexed DNA may also be used to introduce DNA into cells.

In addition to these general guidelines, protein expression/purification kits are produced commercially. See, for instance, the QIAEXPRESS™ expression system from QIAGEN (Chatsworth, Calif.) and various expression systems provided by INVITROGEN (Carlsbad, Calif.). Depending on the details provided by the manufactures, such kits can be used for production and purification of the disclosed bispecific fusion proteins.

In some embodiments, the nucleic acid molecule encodes a CAR as provided herein for expression in a T cell to generate a chimeric antigen receptor T cell. The nucleic acid molecule encoding the chimeric antigen binding receptor can be included in a vector (such as a lentiviral vector) for expression in a host cell, such as a T cell. Exemplary cells include a T cell, a Natural Killer (NK) cell, a cytotoxic T lymphocyte (CTL), and a regulatory T cell. Methods of generating nucleic acid molecules encoding chimeric antigen receptors and T cells including such receptors are known in the art (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; PCT Pub. WO2012/079000, WO2013/126726; and U.S. Pub. 2012/0213783, each of which is incorporated by reference herein in its entirety.)

V. Carbohydrate Recognition Domain-Containing CARs

Certain embodiments, namely the targeting moiety of the CD4-CRD CARs, provide a superior CAR than the "standard" CD4 CAR, in terms of far superior potency at inhibiting HIV-1 infection, and absence of the undesired activity of rendering transduced CD8 T cells susceptible to HIV-1 infection. These improvements are similar to those reported for the targeting moiety of the CD4-10-17b CAR (described in Examples 1-3), in which superior potency was observed only when the linker between the CD4 and 17b moieties was too short to enable simultaneous binding of both to the same gp120 molecule. These results are interpreted in terms of the enhancement achieved by "serial triggering", which is impaired if the binding affinity between effector and target molecules is too high. In addition to the repetitive "on-off" associated with serial triggering, it is proposed that with the CD4-10-17b CAR, a single gp120 molecule is engaged by two separate CAR molecules, thereby amplifying the signal that would be achieved by engaging only a single CAR molecule.

For the present embodiments, the CD4-CRD CARs have been designed with only a very short linker ($Gly_4Ser$, i.e. five amino acids) between the CD4 and the CRD moieties; such spacing does not enable simultaneous binding of both moieties to a single gp120 molecule, and we therefore believe that serial triggering is enabled with this CAR construct.

For a CAR to be an effective component of an HIV functional cure, the transduced cells must persist in active form for extremely long periods, most likely for the life of the infected person. This raises several obvious concerns, and suggests two predicted advantages of the CD4-DCSIGN CAR over the CD4-10-17b CAR. In both cases, the two targeting moieties recognize highly conserved features of HIV-1 gp120. Both recognize the CD4 binding site; the 17b moiety recognizes a conserved component of the coreceptor binding site, whereas the CRD of DC-SIGN binds to high-mannose glycans expressed at multiple sites on the gp120 surface.

While 100% of ~4 dozen isolates tested were potently neutralized by sCD4-35-17b, it is possible that a small minority of natural variants are missing the 17b epitope but still retain effective coreceptor interaction; moreover, during long periods in the presence of the CD4-10-17b CAR, escape variants with mutations in the 17b epitope may be selected, thereby compromising CAR function. The analogous problem seems much less likely to occur with the CD4-DCSIGN CAR, since gp120 has evolved a "glycan shield" as a means of protection against neutralizing antibodies; it seems unlikely that the multiple high mannose glycans can be dispensed with. A second issue concerns potential immune reactions against the targeting moiety of the CAR. For both the CD4-10-17b and the CD4-DCSIGN CARs, each of the moieties in the targeting domain is of human origin; the only non-human, non-natural components are the linkers, which are composed of relatively non-immunogenic $Gly_4Ser$ repeats. However the 17b scFv, though containing invariant human framework sequences, also contains its hypervariable sequences of the complementarity determining regions; this raises the possibility of an anti-idiotypic antibody response, an effect that has been reported for an anti-cancer CAR derived from a human antibody. By contrast, the invariant nature of the CRD of DC-SIGN greatly minimizes the chance for an antibody response.

Data provided herein demonstrate that two very different binding modalities, a scFv and C-type lectin (CLEC) CRDs, confer upon linkage to CD4 desirable traits towards an effective CAR molecule in terms of antiviral potency and non-permissiveness to entry via the CD4 component. The first trait is due to the actual binding of these targeting moieties to HIV-Env and the second due to the mere presence of the moieties causing steric hindrance. It is believed that the examples provided herein enable attaching any Env binding protein domain to CD4 for use in an anti-HIV CAR.

VI. Cells Expressing Chimeric Antigen Receptors

The CARs disclosed herein are designed for expression in cells, for example lymphocytes, to augment proliferation and/or effector function of the cells in response to binding of a ligand to the targeting segment of the CAR. In particular embodiments, constructs encoding CARs are introduced into host cells and expressed therein. In one embodiment, the CAR is expressed in T cells, for example $CD8^+$ T cells. In another embodiment, the CAR is expressed in natural killer (NK) cells.

In some embodiments, the CAR expressed in the cell comprises an extracellular targeting segment, a transmembrane domain and a cytoplasmic signaling domain. In particular embodiments, the cytoplasmic signaling domain is a combined cytoplasmic domain comprising an effector function signaling domain, e.g. zeta, linked to a co-stimulatory signaling domain such as CD28. Upon introduction of these novel hybrid co-stimulatory/effector function chimeric receptors into cells, both a primary effector function signal and a co-stimulatory signal can be regulated by addition of a single ligand that binds to the extracellular domain of the hybrid receptor.

In a particular embodiment, genetically modified T cells are produced by transducing cells obtained from a subject, such as an HIV-infected subject, with a construct encoding the CAR. The genetically modified cells are then adoptively transferred back to the subject and, without being bound by theory, the genetically modified cells provide persistent targeted killing of HIV infected gp120-expressing cells in the subject's body. In some embodiments, the genetically modified cells also provide targeted killing of cells that arise upon activation of latently infected cells. In further embodiments, the genetically modified cells have reduced susceptibility to HIV infection.

Cells expressing CAR molecules with two or more targeting domains in the targeting segment, in which one is derived from CD4, are designed to achieve one or both of two distinct enhancements compared to cells expressing previously described monofunctional CD4-based CARs: (i) an increased potency for killing of HIV-1 Env-expressing cells (including HIV-1-infected cells); and (ii) reduced susceptibility to HIV-1 infection.

Methods of generating chimeric antigen receptors, T cells including such receptors, and their use (e.g., for treatment of cancer) are known in the art and further described herein (see, e.g., Brentjens et al., 2010, Molecular Therapy, 18:4, 666-668; Morgan et al., 2010, Molecular Therapy, published online Feb. 23, 2010, pages 1-9; Till et al., 2008, Blood, 1 12:2261-2271; Park et al., *Trends Biotechnol.*, 29:550-557, 2011; Grupp et al., N Engl J Med., 368:1509-1518, 2013; Han et al., J. Hematol Oncol., 6:47, 2013; Tumaini et al., Cytotherapy, 15, 1406-1417, 2013; Haso et al., (2013) *Blood,* 121, 1165-1174; PCT Pubs. WO2012/079000, WO2013/126726; and U.S. Pub. 2012/0213783, each of which is incorporated by reference herein in its entirety). For example, a nucleic acid molecule encoding a disclosed chimeric antigen binding receptor can be included in an expression vector (such as a lentiviral vector) used to transduce a host cell, such as a T cell, to make the disclosed CAR. In some embodiments, methods of using the chimeric antigen receptor include isolating T cells from a subject, transducing the T cells with an expression vector (such as a lentiviral vector) encoding the chimeric antigen receptor, and administering the CAR-expressing T cells to the subject for treatment, for example for treatment of a HIV-1 infection in the subject.

VII. Measuring Chimeric Antigen Receptor Function

The chimeric antigen receptors disclosed herein can be used to increase proliferation and/or effector function (including cytolysis and cytokine secretion) of immune cells.

Increased proliferation can be determined by measuring the incorporation of either tritiated thymidine or orotic acid to measure DNA synthesis following ligand binding to the CAR-expressing cells disclosed herein. The incorporation of bromodeoxyuridine into newly synthesized DNA can be measured by immunological staining and the detection of dyes, or by ELISA (Enzyme-linked immunosorbent assay) (Doyle et al., Cell and Tissue Culture: Laboratory Procedures, Wiley, Chichester, England, (1994)). The mitotic index of cells can be determined by staining and microscopy, by the fraction labeled mitoses method or by fluorescence activated cell sorting (FACS) analysis (Doyle et al., supra; Dean, *Cell Tissue Kinet.* 13:299-308, 1980; Dean, *Cell Tissue Kinet.* 13:672-681, 1980). The increase in cell size which accompanies progress through the cell cycle can be measured by centrifugal elutriation (Faha et al., *J. Virol.* 67:2456-2465, 1993). Increases in the number of cells may also be measured by counting the cells, with or without the addition of vital dyes. In addition, signal transduction can be measured by the detection of phosphotyrosine, the in vitro activity of tyrosine kinases from activated cells, c-myc induction, or calcium mobilization.

One measure of T cell activation is the production of cytokines. In some embodiments, CD28 co-stimulation increases cytokine production by increasing transcription of cytokine genes and stabilizing cytokine mRNAs. In other embodiments, $CD4^+$ T cells and $CD8^+$ T cells expressing the CARs disclosed herein have a greater capacity for cytokine production. Specific, non-limiting examples of cytokines include IL-2, IL-4, and γ-IFN.

In some embodiments, cells expressing the CAR molecules disclosed herein exhibit an increased potency for killing of HIV-1 Env-expressing cells (including HIV-1-infected cells). Increased killing of HIV-infected cells can be measured by suppression of HIV-1 infection in PBMC (i.e. quantification of p24 via ELISA as a measurement of HIV spread within culture). In some embodiments, killing of HIV-infected cells can be measured upon activation from latency. In some embodiments, increased killing of HIV-infected cells is measured in a sample obtained from a subject, for example from a subject being treated with the CAR molecules of the present disclosure.

In some embodiments, cells expressing the CAR molecules disclosed herein exhibit reduced susceptibility to HIV-1 infection. In particular examples, increased killing of HIV-infected cells comprises measuring the level of HIV infected cells in the subject, wherein the administration of the composition reduces the level of HIV-infected cells in the subject, compared to the level of HIV-infected cells in the subject prior to the administration of the composition. Reduced susceptibility can be measured by expressing CAR molecules in cells, for example $CD8^+$ T cells, and mixing the CAR-expressing cells with HIV-1 Env particles or with HIV-1-infected cells to test for susceptibility of the CAR-expressing cells to HIV-1 pseudovirus infection.

VIII. Pharmaceutical Compositions Incorporating Cells Expressing Chimeric Antigen Receptors and Clinical Uses Thereof The unexpectedly superior killing of virus-infected cells exhibited by the disclosed CAR-expressing cells makes them useful for treating viral infections in human and other animal subjects. In some embodiments, susceptible viruses include the immunodeficiency viruses, such as HIV and similar or related viruses in simians and other animals.

Lymphocytes, such as cytotoxic $CD8^+$ T cells (CTLs), which have been engineered with the multi-functional CARs disclosed herein, can be used to augment proliferation and/or killing of cells infected by any one of a variety of viral or parasitic diseases, where the infected cells express the antigens from the pathogen. In particular embodiments, CTLs expressing the multi-functional CARs disclosed herein would be particularly effective against viral diseases where transplanted autologous CTLs have shown some efficacy or where explanted and expanded CTLs continued to have cytolytic activity against virally infected cells, such as HIV. These multi-functional CARs can be constructed with multispecific targeting segments having two or more targeting domains which recognize, or bind to, the viral envelope proteins. For example, antibodies which recognize gp120 or the CD4 extracellular domain which recognizes gp120 can be used to engineer HIV-specific CTLs.

A general strategy for transferring genes into donor cells is disclosed in U.S. Pat. No. 5,529,774, which is incorporated by reference. Generally, a gene encoding a protein, such as a multi-functional CAR, having therapeutically desired effects is cloned into a viral expression vector, and that vector is then introduced into the target organism. In some embodiments, high-titer retroviral producer lines are used to transduce the multi-functional CAR constructs into T-cells, hematopoietic stem cells or other cells through the process of retroviral mediated gene transfer. The virus infects the cells, and produces the CAR protein sequence in vivo. As an alternative to adding the sequences encoding the CAR protein to the DNA of a virus, it is also possible to introduce such a gene into the somatic DNA of cells, by methods that are well known in the art (Sambrook et al., *In Molecular Cloning: A Laboratory Manual*, Cold Spring Harbor, N.Y., 1989). These methods can be used to introduce the herein disclosed multi-functional CAR proteins to human cells to treat and/or provide long-term resistance to HIV-1 infection or AIDS.

In a particular embodiment, genetically modified cells are produced by transducing cells obtained from a subject, such as an HIV-infected subject, with a construct encoding the multi-functional CAR. The genetically modified cells are then adoptively transferred back to the subject and, without being bound by theory, the genetically modified cells provide persistent targeted killing of HIV-infected cells, for example gp120-expressing cells, in the subject's body. In yet another embodiment, allogeneic cells are genetically modified by transducing the cells with a construct encoding the CAR.

In another embodiment, the T cells genetically modified to express a CD4 CAR have reduced susceptibility to HIV infection, for example, when transferred back to the subject, when the CAR is a multispecific CAR. In some embodiments, introducing a nucleic acid molecule encoding a multispecific chimeric antigen receptor protein into a host T cell under conditions sufficient for expression of the encoded multispecific chimeric antigen receptor protein in the host cell, results in a reduced level of HIV infection in the host T cell expressing the chimeric antigen receptor protein, compared to a T cell that is not expressing the encoded chimeric receptor protein or that is expressing a monofunctional CD4 chimeric antigen receptor. Thus, in some embodiments, the introduction of the genetically modified cells do not act as a reservoir of HIV viral particles and thereby reduce the spread of HIV infection in a subject. In particular embodiments, cells with reduced susceptibility to HIV infection express a multi-functional CAR protein having CD4 as the first targeting domain and a CD4i scFV as the second targeting domain. Specific, non-limiting examples of CD4i scFVs include 17b, 48d, CG10, 412d, X5, 21C, 19e, 47E, E51, 16 c, 23e, 411G, 31H, ED47, and ED49 (Thali et al. *J. Virol* 67:3978-3988, 1993; Gershoni et al. *FASEB J.* 7:1185-1187, 1993; Farzan et al. *J. Virol.* 79:6068-77, 2005; Moulard et al., *PNAS* 99:6913-6918, 2002; Salzwedel et al., *J. Virol.*, 74:326-333, 2000; Reeves et al., *J. Virol.*, 79:4991-4999, 2005; and Nora et al., *Retrovirol.*, 5:1-16, 2008). In other embodiments, cells with reduced susceptibility to HIV infection express a multi-functional CAR protein having CD4 as the first targeting domain and any Ig molecule or scFV as the second targeting domain. Specific, non-limiting examples of Ig molecules directed against gp120 that can be used as a targeting moiety of the disclosed CARs include PG9, PG16, PGT141, PGT142, PGT143, PGT144, PGT145, HGN194, and 2G12 (Walker et al., *Science* 326:285-289, 2009; Walker et al., *Nature* 477:466-470, 2011; Watkins et al., *PLoS ONE* 2011; 6: e18207; Trkola et al., Journal Of Virology 69:6609-6617, 1995). Specific, non-limiting examples of Ig molecules directed against gp41 that can be used as a targeting moiety of the disclosed CARs include 10E8, 4E10, 2F5, Z13e1. In yet other specific, non-limiting examples, the Ig molecule is a monoclonal antibody against dengue virus glycoprotein (for example, mAb DDY3), a monoclonal antibody against a breast cancer antigen (for example, mAb 4D5—Herceptin), or a monoclonal antibody against an epidermal growth factor receptor variant III (EGFRvIII) (for example, mAb 139).

A wide variety of host cells may be employed, normally cells from vertebrates, more particularly, mammals, desirably domestic animals or primates, particularly humans. Suitable host cells also include hematopoietic stem cells, which develop into effector cells with both myeloid and lymphoid phenotype including granulocytes, mast cells, basophils, macrophages, natural killer (NK) cells and T and B lymphocytes. CAR proteins disclosed herein can be expressed in effector cells, such as lymphocytes including cytotoxic lymphocytes (CTL), NK cells, tumor-infiltrating lymphocytes (TIL) or other cells which are capable of releasing cytokines or killing target cells when activated. Thus, diseased cells, such as cells infected with HIV, where the diseased cells have a surface marker associated with the diseased state may be made specific targets of the effector cells. By providing a receptor extracellular domain, e.g., CD4, which binds to a surface marker, for example gp120 for HIV, the CAR-expressing cells may serve as therapeutic agents. By modifying the cells further to prevent the expression or translocation of functional Class I and/or II MHC antigens, the cells will be able to avoid recognition by the host immune system as foreign and can therefore be therapeutically employed in any individual regardless of genetic background.

Cells containing the constructs encoding the CAR molecules described herein may be grown in an appropriate nutrient medium for expansion or may be expanded directly in vivo via signaling through the CARs, depending on the cell type, and used in a variety of ways.

Additional types of cells that would benefit from the introduction of the constructs encoding the CARs disclosed herein include cells that have genes previously introduced or simultaneously introduced with a chimeric receptor which may serve in protein production or to correct a genetic defect. Production of proteins may include growth factors, such as, erythropoietin, G-CSF, M-CSF, and GM-CSF, epidermal growth factor, platelet derived growth factor, human growth factor, transforming growth factor, or lymphokines, such as the interleukins.

The cells expressing the constructs expressing the CAR molecules disclosed herein may be administered to humans, or other animals on whose cells (for example, HIV-infected cells) they are effective, in various manners such as orally, intravenously, intramuscularly, intraperitoneally, intranasally, intradermally, intrathecally, and subcutaneously. The particular mode of administration and the dosage regimen will be selected by the attending clinician, taking into account the particulars of the case (e.g., the subject, the disease, and the disease state involved, and whether the treatment is prophylactic or post-infection). Treatment may involve a single administration, daily administration, or multi-daily doses of CAR-expressing cells.

In some embodiments, the level of HIV infected cells in a subject with HIV is measured in a biological sample obtained from the subject to determine if the administration of the CAR-expressing cells to the subject decreases the level of HIV-infected cells in the subject. The biological sample can be obtained from the subject before or after the subject has been administered the CAR-expressing cells. In some embodiments, the administration of the CAR-expressing cells, or a composition comprising the CAR-expressing cells, reduces the level of HIV-infected cells in the subject, compared to the level of HIV-infected cells in the subject prior to the administration of the composition. In particular embodiments, the administration of multispecific CAR-expressing cells, or a composition comprising multispecific CAR-expressing cells, reduces the susceptibility of the CAR-expressing cells in the subject to be infected by HIV. Thus, without being bound by theory, the level of HIV-infected cells in a subject administered multispecific CAR-expressing cells is reduced, compared to the level of HIV-infected cells in a subject administered a monofunctional CAR-expressing cell.

Such CAR-expressing cells may be administered at a dose of between about $10^6$ and $10^{10}$ cells, on one or several occasions. The number of cells will depend on the patient, as well as the CAR and cells chosen to express the protein. The number of CAR-expressing cells administered will be dependent on the subject being treated, the severity of the affliction, and the manner of administration, and is best left to the judgment of the prescribing clinician. Within these bounds, the formulation to be administered will contain a quantity of the genetically engineered cells in an amount effective to achieve the desired effect in the subject being treated.

Pharmaceutical compositions that comprise CAR-expressing cells as described herein as an active ingredient will be formulated depending upon the particular mode of administration chosen. The pharmaceutically acceptable carriers and excipients useful delivering these cells are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate.

Cells expressing CAR proteins, for instance sCD4-scFv (17b)-CAR, CD4-DCSIGN CAR, CD4-LSIGN CAR, CD4-Langerin CAR, or CD-MBL2 CAR, are particularly useful in the prevention of infection during or immediately after HIV exposure (e.g., mother/infant transmission, post-exposure prophylaxis, and as a topical inhibitor). In such instances, one or more doses of the CAR protein are administered before or soon after the triggering event. To prevent or ameliorate mother/infant transmission of viral infection, for instance, it may be beneficial to administer the CAR-expressing cell to the mother during pregnancy, and/or immediately before or following delivery, and/or directly to the newborn immediately after birth. Post-exposure prophylactic treatments may be particularly beneficial where there has been accidental exposure (for instance, a medically related accidental exposure), including but not limited to a contaminated needle-stick or medical exposure to HIV-1 contaminated blood or other fluid.

The present disclosure also includes combinations of cells expressing the CAR proteins disclosed herein with one or more other agents useful in the treatment of disease, e.g. HIV disease. For example, the CAR-expressing cells may be administered, whether before or after exposure to the virus, in combination with effective doses of other anti-virals, immunomodulators, anti-infectives, and/or vaccines. The term "administration in combination" refers to both concurrent and sequential administration of the active agents.

Examples of antiviral agents that can be used in combination with the CAR proteins disclosed herein are: AL-721 (from Ethigen of Los Angeles, Calif.), recombinant human interferon beta (from Triton Biosciences of Alameda, Calif.), Acemannan (from Carrington Labs of Irving, Tex.), gangiclovir (from Syntex of Palo alto, CA), didehydrodeoxythymidine or d4T (from Bristol-Myers-Squibb), EL10 (from Elan Corp. of Gainesville, Ga.), dideoxycytidine or ddC (from Hoffman-LaRoche), Novapren (from Novaferon labs, Inc. of Akron, Ohio), zidovudine or AZT (from Burroughs Wellcome), ribaririn (from Viratek of Costa Mesa, Calif.), alpha interferon and acyclovir (from Burroughs Wellcome), Indinavir (from Merck & Co.), 3TC (from Glaxo Wellcome), Ritonavir (from Abbott), Saquinavir (from Hoffmann-LaRoche), and others.

Examples of immuno-modulators that can be used in combination with the CAR proteins disclosed herein are AS-101 (Wyeth-Ayerst Labs.), bropirimine (Upjohn), gamma interferon (Genentech), GM-CSF (Genetics Institute), IL-2 (Cetus or Hoffman-LaRoche), human immune globulin (Cutter Biological), IMREG (from Imreg of New Orleans, La.), SK&F106528, and TNF (Genentech).

Examples of some anti-infectives with which the CAR proteins can be used include clindamycin with primaquine (from Upjohn, for the treatment of *Pneumocystis pneumonia*), fluconazlone (from Pfizer for the treatment of cryptococcal meningitis or candidiasis), nystatin, pentamidine, trimethaprim-sulfamethoxazole, and many others.

The combination therapies are of course not limited to the lists provided in these examples, but include any composition for the treatment of HIV disease (including treatment of AIDS).

1. Therapeutic Methods

Methods are disclosed herein for the prevention or treatment of an HIV infection, such as an HIV-1 infection. Prevention can include inhibition of infection with HIV-1. The methods include contacting a cell with a therapeutically effective amount of a disclosed CAR or T cell expressing a CAR that specifically binds HIV-1 Env, or a nucleic acid encoding such a CAR. The method can also include administering to a subject a therapeutically effective amount of a CAR or T cell expressing a CAR that specifically binds HIV-1 Env, or a nucleic acid encoding such a CAR, to a subject. In some examples, the CAR, T cell expressing a CAR, or nucleic acid molecule, can be used pre-exposure (for example, to prevent or inhibit HIV infection). In some examples, the, CAR, T cell expressing a CAR, or nucleic acid molecule, can be used in post-exposure prophylaxis. In some examples, the CAR can be used to eliminate or reduce the viral reservoir of HIV-1 in a subject. For example a therapeutically effective amount of a CAR, T cell expressing a CAR, or nucleic acid molecule, can be administered to a subject with HIV-1, such as a subject being treated with anti-viral therapy.

HIV infection does not need to be completely eliminated for the method to be effective. For example, a method can decrease HIV infection by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to HIV infection in the absence of the treatment. In some embodiments, the cell is also contacted with a therapeutically effective amount of an additional agent, such as anti-viral agent. The cell can be in vivo or in vitro. The methods can include administration of one on more additional agents known in the art. In additional embodiments, HIV replication can be reduced or inhibited by similar methods. HIV replication does not need to be completely eliminated for the method to be effective. For example, a method can decrease HIV replication by a desired amount, for example by at least 10%, at least 20%, at least 50%, at least 60%, at least 70%, at least 80%, at least 90%, at least 95%, at least 98%, or even at least 100% (elimination of detectable HIV), as compared to HIV replication in the absence of the treatment.

Methods to assay for neutralization activity include, but are not limited to, a single-cycle infection assay as described in Martin et al. (*Nature Biotech* 21:71-76, 2003). In this assay, the level of viral activity is measured via a selectable marker whose activity is reflective of the amount of viable virus in the sample, and the $IC_{50}$ is determined. In other assays, acute infection can be monitored in the PM1 cell line or in primary cells (normal PBMC). In this assay, the level of viral activity can be monitored by determining the p24 concentrations using ELISA. See, for example, Martin et al. (*Nature Biotech* 21:71-76, 2003).

In one embodiment, administration of a disclosed CAR, T cell expressing a CAR, or nucleic acid molecule, results in a reduction in the establishment of HIV infection and/or reducing subsequent HIV disease progression in a subject. A reduction in the establishment of HIV infection and/or a reduction in subsequent HIV disease progression encompass any statistically significant reduction in HIV activity. In some embodiments, methods are disclosed for treating a subject with an HIV-1 infection. These methods include administering to the subject a therapeutically effective amount of a CAR, T cell expressing a CAR, or nucleic acid molecule, thereby preventing or treating the HIV-1 infection.

Studies have shown that the rate of HIV transmission from mother to infant is reduced significantly when zidovudine is administered to HIV-infected women during pregnancy and delivery and to the offspring after birth (Connor et al., 1994 *Pediatr Infect Dis J* 14: 536-541). Several studies of mother-to-infant transmission of HIV have demonstrated a correlation between the maternal virus load at delivery and risk of HIV transmission to the child. The present disclosure provides CARs, T cells expressing a CAR, and nucleic acid molecules that are of use in decreasing HIV-transmission from mother to infant. Thus, in some examples, a therapeutically effective amount of a CAR, T cell expressing a CAR, or nucleic acid molecule is administered in order to prevent transmission of HIV, or decrease the risk of transmission of HIV, from a mother to an infant. In some examples, a therapeutically effective amount of the CAR, T cell expressing a CAR, or nucleic acid molecule, is administered to mother and/or to the child at childbirth. In other examples, a therapeutically effective amount of the antibody, antigen binding fragment, or nucleic acid encoding the antibody or antigen binding fragment is administered to the mother and/or infant prior to breast feeding in order to prevent viral transmission to the infant or decrease the risk of viral transmission to the infant. In some embodiments, both a therapeutically effective amount of the antibody, antigen binding fragment, or nucleic acid encoding the antibody or antigen binding fragment and a therapeutically effective amount of another agent, such as zidovudine, is administered to the mother and/or infant.

For any application, the CAR, T cell expressing a CAR, or nucleic acid molecule can be combined with anti-retroviral therapy. Antiretroviral drugs are broadly classified by the phase of the retrovirus life-cycle that the drug inhibits. The disclosed antibodies can be administered in conjunction with nucleoside analog reverse-transcriptase inhibitors (such as zidovudine, didanosine, zalcitabine, stavudine, lamivudine, abacavir, emtricitabine, entecavir, and apricitabine), nucleotide reverse transcriptase inhibitors (such as tenofovir and adefovir), non-nucleoside reverse transcriptase inhibitors (such as efavirenz, nevirapine, delavirdine, etravirine, and rilpivirine), protease inhibitors (such as saquinavir, ritonavir, indinavir, nelfinavir, amprenavir, lopinavir, fosamprenavir, atazanavir, tipranavir, and darunavir), entry or fusion inhibitors (such as maraviroc and enfuvirtide), maturation inhibitors, (such as bevirimat and vivecon), or a broad spectrum inhibitors, such as natural antivirals. In some examples, a disclosed antibody or active fragment thereof or nucleic acids encoding such is administered in conjunction with IL-15, or conjugated to IL-15.

In some embodiments, the disclosed methods include isolating T cells from a subject and transducing the T cells with an expression vector (such as a lentiviral vector) encoding the chimeric antigen receptor to make a CAR T cell. The methods can further include administering the CAR-expressing T cells to the subject for treatment, for example for treatment of an HIV-1 infection in the subject.

2. Dosages

A therapeutically effective amount of a CAR (such as sCD4-scFv(17b) CAR, CD4-DCSIGN CAR, CD4-LSIGN CAR, CD4-Langerin CAR, or CD-MBL2 CAR), T cell expressing a CAR, or nucleic acid molecule encoding such molecules, will depend upon the severity of the disease and/or infection and the general state of the patient's health. A therapeutically effective amount is that which provides either subjective relief of a symptom(s) or an objectively identifiable improvement as noted by the clinician or other qualified observer. The CAR, T cell expressing a CAR, or nucleic acid molecule encoding such molecules, can be administered in conjunction with another therapeutic agent, either simultaneously or sequentially.

Single or multiple administrations of a composition including a disclosed CAR, T cell expressing a CAR, or nucleic acid molecule encoding such molecules, can be administered depending on the dosage and frequency as required and tolerated by the patient. Compositions including the CAR, T cell expressing a CAR, or nucleic acid molecule encoding such molecules, should provide a sufficient quantity of at least one of the CAR, T cell expressing a CAR, or nucleic acid molecule encoding such molecules to effectively treat the patient. The dosage can be administered once, but may be applied periodically until either a therapeutic result is achieved or until side effects warrant discontinuation of therapy. In one example, a dose of the antibody or antigen binding fragment is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The therapeutically effective dose can be determined from cell culture assays and animal studies.

In certain embodiments, the CAR, T cell expressing a CAR, or nucleic acid molecule, or vector encoding such a molecule, or a composition including such molecules, is administered at a dose in the range of from about 5 or 10 nmol/kg to about 300 nmol/kg, or from about 20 nmol/kg to about 200 nmol/kg, or at a dose of about 5, 10, 15, 20, 25, 30, 35, 40, 45, 50, 55, 60, 65, 70, 75, 80, 85, 90, 95, 100, 110, 120, 125, 130, 140, 150, 160, 170, 175, 180, 190, 200, 210, 220, 230, 240, 250, 260, 270, 280, 290, 300, 350, 400, 450, 500, 750, 1000, 1250, 1500, 1750 or 2000 nmol/kg, or at a dose of about 5, 10, 20, 30, 40, 50, 60, 70, 80, 90, 100, 110, 120, 130, 140, 150, 160, 170, 180, 190, 200, 250, 300, 350, 400, 450, 500, 550, 600, 650, 700, 750, 800, 850, 900, 950 or 1000 µg/kg, or about 1, 1.25, 1.5, 2, 2.5, 3, 3.5, 4, 4.5, 5, 5.5, 6, 6.5, 7, 7.5, 8, 8.5, 9, 9.5 or 10 mg/kg, or other dose deemed appropriate by the treating physician. The doses described herein can be administered according to the dosing frequency/frequency of administration described herein, including without limitation daily, 2 or 3 times per week, weekly, every 2 weeks, every 3 weeks, monthly, etc.

In some embodiments, a disclosed therapeutic agent is administered may be administered intravenously, subcutaneously or by another mode daily or multiple times per week for a period of time, followed by a period of no treatment, then the cycle is repeated. In some embodiments, the initial period of treatment (e.g., administration of the therapeutic agent daily or multiple times per week) is for 3 days, 1 week, 2 weeks, 3 weeks, 4 weeks, 5 weeks, 6 weeks, 7 weeks, 8 weeks, 9 weeks, 10 weeks, 11 weeks or 12 weeks. In a related embodiment, the period of no treatment lasts for 3 days, 1 week, 2 weeks, 3 weeks or 4 weeks. In certain embodiments, the dosing regimen of the therapeutic agent is daily for 3 days followed by 3 days off; or daily or multiple times per week for 1 week followed by 3 days or 1 week off; or daily or multiple times per week for 2 weeks followed by 1 or 2 weeks off; or daily or multiple times per week for 3 weeks followed by 1, 2 or 3 weeks off; or daily or multiple times per week for 4, 5, 6, 7, 8, 9, 10, 11 or 12 weeks followed by 1, 2, 3 or 4 weeks off.

3. Modes of Administration

A CAR, T cell expressing a CAR, or nucleic acid molecule encoding such molecules, or a composition including such molecules, as well as additional agents, can be administered to subjects in various ways, including local and systemic administration, such as, e.g., by injection subcutaneously, intravenously, intra-arterially, intraperitoneally, intramuscularly, intradermally, or intrathecally. In an embodiment, a therapeutic agent is administered by a single subcutaneous, intravenous, intra-arterial, intraperitoneal, intramuscular, intradermal or intrathecal injection once a day. The therapeutic agent can also be administered by direct injection at or near the site of disease.

The therapeutic agent may also be administered orally in the form of microspheres, microcapsules, liposomes (uncharged or charged (e.g., cationic)), polymeric microparticles (e.g., polyamides, polylactide, polyglycolide, poly(lactide-glycolide)), microemulsions, and the like.

A further method of administration is by osmotic pump (e.g., an Alzet pump) or mini-pump (e.g., an Alzet mini-osmotic pump), which allows for controlled, continuous and/or slow-release delivery of the therapeutic agent or pharmaceutical composition over a pre-determined period. The osmotic pump or mini-pump can be implanted subcutaneously, or near a target site.

It will be apparent to one skilled in the art that the therapeutic agent or compositions thereof can also be administered by other modes. Determination of the most effective mode of administration of the therapeutic agent or compositions thereof is within the skill of the skilled artisan. The therapeutic agent can be administered as pharmaceutical formulations suitable for, e.g., oral (including buccal and sub-lingual), rectal, nasal, topical, pulmonary, vaginal or parenteral (including intramuscular, intraarterial, intrathecal, subcutaneous and intravenous) administration, or in a form suitable for administration by inhalation or insufflation. Depending on the intended mode of administration, the pharmaceutical formulations can be in the form of solid, semi-solid or liquid dosage forms, such as tablets, suppositories, pills, capsules, powders, liquids, suspensions, emulsions, creams, ointments, lotions, and the like. The formulations can be provided in unit dosage form suitable for single administration of a precise dosage. The formulations comprise an effective amount of a therapeutic agent, and one or more pharmaceutically acceptable excipients, carriers and/or diluents, and optionally one or more other biologically active agents.

4. Compositions

Compositions are provided that include one or more of the CAR, T cell expressing a CAR, or nucleic acid molecule encoding such molecules, that are disclosed herein, in a carrier. The compositions are useful, for example, for example, for the treatment or detection of an HIV-1 infection. The compositions can be prepared in unit dosage forms for administration to a subject. The amount and timing of administration are at the discretion of the treating physician to achieve the desired purposes. The CAR, T cell expressing a CAR, or nucleic acid molecule encoding such molecules can be formulated for systemic or local administration. In one example, the CAR, T cell expressing a CAR, or nucleic acid molecule encoding such molecules, is formulated for parenteral administration, such as intravenous administration.

In some embodiments, the compositions comprise a CAR, T cell expressing a CAR, or nucleic acid molecule encoding such molecules, in at least about 70%, 75%, 80%, 85%, 90%, 95%, 96%, 97%, 98% or 99% purity. In certain embodiments, the compositions contain less than about 10%, 5%, 4%, 3%, 2%, 1% or 0.5% of macromolecular contaminants, such as other mammalian (e.g., human) proteins.

The compositions for administration can include a solution of the CAR, T cell expressing a CAR, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions will be known or apparent to those skilled in the art and are described in more detail in such publications as *Remington's Pharmaceutical Science, 19th ed.*, Mack Publishing Company, Easton, Pa. (1995). In some embodiments, the composition can be a liquid formulation including one or more antibodies, antigen binding fragments (such as an antibody or antigen binding fragment that specifically binds to HIV-1 Env), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antibody binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

One approach to administration of nucleic acids is direct administration with plasmid DNA, such as with a mammalian expression plasmid. The nucleotide sequence encoding the disclosed fusion proteins, can be placed under the control of a promoter to increase expression.

In another approach to using nucleic acids, a disclosed fusion protein can also be expressed by attenuated viral hosts or vectors or bacterial vectors. Recombinant vaccinia virus, adeno-associated virus (AAV), herpes virus, retrovirus, cytomegalovirus or other viral vectors can be used to express the antibody. For example, vaccinia vectors and methods useful protocols are described in U.S. Pat. No. 4,722,848. BCG (*Bacillus* Calmette Guerin) provides another vector for expression of the disclosed antibodies (see Stover, *Nature* 351:456-460, 1991).

In one embodiment, a nucleic acid encoding a disclosed CAR fusion protein, is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

IX. Kits

Kits are also provided. For example, kits for treating a subject with an HIV-1 infection, or for detecting HIV-1 Env in a sample or in a subject. The kits will typically include a CAR, T cell expressing a CAR, or nucleic acid molecule encoding such molecules, or compositions including such molecules. More than one of the disclosed CAR, T cell expressing a CAR, or nucleic acid molecule encoding such molecules, or compositions including such molecules can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, or compositions. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of the antibodies, antigen binding fragments, conjugates, nucleic acid molecules, or compositions included in the kit. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

The following examples are provided to illustrate certain particular features and/or embodiments. These examples are not to be construed to limit the invention to the particular features or embodiments described.

Example 1

Construction and Expression of a CD4-17b Chimeric Antigen Receptor (CAR) and Measuring Activity of CD4-17b CAR-Expressing Cells This example describes representative methods for the construction and expression of a CD4-17b CAR, as well as various in vitro assays that measure the activity of cells expressing a CD4-17b CAR.

PBMCs and Cell Lines

All of the PBMCs used in this study were derived from healthy donors visiting the NIH blood bank. The cells were isolated from buffy-coat by Ficoll-Hypaque gradient separation. Isolated PBMCs were subsequently cultured in AIM-V medium (Life Technologies) supplemented with 5% human AB serum (Valley Biomedical) and 300 IU/ml IL-2 (Chiron). HEK 293T cells (ATCC) and 293GP cells (BD biosciences) were maintained in Dulbecco's Modified Eagle medium (DMEM) containing 10% fetal bovine serum (FBS), 25 mM HEPES, 2 mM glutamine and 1% sodium pyruvate. SupT1-DC-SIGNR cells were grown as suspension in RPMI-1640 medium plus 10% FBS and 2 mM glutamine. Chinese hamster ovary (CHO) cells were cultured in complete DMEM medium containing 10% FBS, 2 mM glutamine, 1% nonessential amino acids and 2 5 mM HEPES buffer. Env15 cells expressing the Env (gp120) protein from HIV-1 isolate $III_B$ were cultured in the same medium with the addition of 50 µM methotrexate (MTX). All cell culture medium contained 100 U/ml penicillin and 100 µg/ml streptomycin. All cell lines and PBMCs were maintained in an environment of 37° C. and 5% $CO_2$.

T Cell Stimulation $5 \times 10^7$ PBMC were thawed and washed once in T cell medium. PBMCs were suspended at a concentration of $2 \times 10^6$ cells/ml in T cell medium containing 50 ng/ml of the anti-CD3 monoclonal antibody OKT3, 300 IU/ml of recombinant human IL-2 and 5% human AB serum. 2 ml of the cell suspension were added to each well in a 24-well plate. Cells were cultured in 5% $CO_2$, 37° C. for 2 days until retroviral transduction was performed.

Generation of Retroviral Constructs

The recombinant plasmids containing the coding sequence for the two-domain CD4 (sCD4), sCD4-10-17b, or sCD4-35-17b was synthesized respectively by Life Technologies. The synthesized DNA fragments were sequence confirmed and subcloned in frame into pMSGV-1-based vector containing CD28 transmembrane and CD28 and CD3 signaling moieties to generate pMSGV-sCD4, pMSGVsCD4-10-17b or pMSGV-sCD4-35-17b. Detailed description of the structure and sequence (including the linker sequence) of these constructs are shown in the sequence listing.

Retrovirus Vector Production and Transduction of T Cells

Retroviruses carrying a CAR transgene were made by transient transfection as described below. Briefly, 293GP cells (BD Biosciences) were co-transfected with retroviral vector plasmid and envelope encoding plasmid RD114 using Lipofectamine 2000 reagent (Life Technologies). Supernatants containing the retrovirus were collected at 48 hours post transfection and stored in −80° C. On the day of transduction, retroviral supernatant was rapidly thawed and diluted 1:1 in serum free RPM1640 medium. 4 ml/well of 1:1 diluted supernatant were added to RetroNectin (Takara)-coated non-tissue culture-treated 6-well plates. After addition of the supernatants, the plates were centrifuged at 2000 g for 2 hours at 32° C. The supernatant was then aspirated from the wells. Subsequently, 1.5 ml of stimulated PBMCs were added into one well with a density of $0.5 \times 10^6$ cells/ml in AIM-V medium containing recombinant human IL-2 (300 IU/ml) and 5% human AB serum. After addition of cells, the plates were centrifuged for 10 minutes at 1000 g. The plates were incubated at 37° C. overnight. A second round of transduction was performed the next day using the same procedures described above. The transduced cells were cultured in 37° C., 5% $CO_2$ until analysis for CAR expression by flow cytometry.

CAR Detection on Transduced T Cells

Approximately $1 \times 10^6$ cells were washed and suspended in FACS buffer (Phosphate-buffered saline plus 0.1% sodium azide and 0.4% BSA, pH 7.0). Fluorescein isothiocyanate (FITC)-labeled anti-CD3 (clone HIT3a), phycoerythrin (PE)-labeled anti-CD4 (clone RPA-T4) and Allophycocyanin (APC)-labeled anti-CD8 (clone SK1) antibodies were then added to the cells following the instructions provided by the manufacturer (BD Biosciences). After a 30 minute incubation at 4° C., cells were washed three times with FACS buffer. After washing with FACS buffer, cells labeled with biotinylated protein L were incubated with PE-labeled streptavidin following the instruction manual (BD Biosciences). Flow cytometry acquisition was performed with a BD FACS Calibur (BD Biosciences), and analysis was performed with FlowJo (Treestar).

Interferon-γ Secretion Enzyme-Linked Immunosorbent Assay (ELISA)

In a well of the 96-well round bottom plate, same amount ($1 \times 10^5$) of target and effector cells were mixed in 200 µl of T cell media without IL-2. In addition, wells containing T cells alone were prepared. The plates were incubated at 37° C. for 18-20 hours. Following the incubation, an IFN-γ ELISA assay was performed using standard methods (Pierce).

Cytotoxicity Assay

A cytotoxicity assay was performed using the radioisotope-free PanToxiLux kit (OncoImmunin, Inc.) following the instruction manual exactly. In a PanToxiLux assay, duplicates of serial two-fold dilutions of the effector T cells were made on a 96-well plate, with the highest cell number of $10^6$ cells/well and the lowest cell number of $2.5 \times 10^5$ cells/well. Target cells were labeled with 1:2000 diluted TFL-4 at 37° C. for 30 minutes. After a complete wash with phosphate buffered saline (PBS), duplicates of $1 \times 10^5$ target cells were added to the wells corresponding to each effector cell dilution. Fluorochrome-labeled caspase substrate was added to the co-culture. After incubation at 37° C. for 2 hours, the cells were washed and analyzed by flow cytometry.

Inhibition of Pseudotyped HIV Production

HEK 293 T cells were transfected with plasmids to generate the luciferase gene-carrying pseudotyped (QH0692) as described previously. Six hours post transfection, $1 \times 10^5$/well transfected cells were mixed with effector CAR-T cells at various E/T ratios. Cell co-culture was incubated at 37° C. for 2 days. Culture supernatants were collected and cleared by centrifugation at 2000 rpm for 5 minutes. On a 96-well round bottom plate, 50 µl of cleared pseudotyped HIV supernatants produced at various E/T ratios were inoculated onto $2 \times 10^5$/well SupT1-DCSIGNR cells in quadruplicates in the presence of 20 µg/ml of DEAE-dextran. 48 hours post-infection, cells were analyzed for infection by luciferase assay, as described previously.

Results

The initial construct generated employed a scFv of the 17b human mAb, which targets a highly conserved CD4-induced epitope on gp120 (the bridging sheet) involved in binding to coreceptor. Previous studies (Lagenaur et al., *Retrovirology* 7:11, 2010; incorporated herein by reference) demonstrated that a soluble construct (designated sCD4-17b) neutralized HIV-1 primary isolate pseudotype viruses with very high potency and breadth (100% of nearly 4 dozen Envs of diverse genetic subtypes). The potency was strictly dependent on linker length, i.e. the linker had to be sufficiently long to enable simultaneous binding of the sCD4 and 17b scFv moieties to a single gp120 subunit. The design was based on the X-ray crystal structure of gp120 core bound to sCD4 and 17b Fab (Kwong, et al. (1998) *Nature* 393:648-659). Variant constructs were designated according to the number of amino acids in the linker. It was determined that constructs with a sufficiently long linker (sCD4-35-17b and sCD4-40-17b) showed potent neutralization due to high affinity associated with simultaneous binding of the sCD4 and 17b scFv moieties to a single gp120 subunit. By contrast, constructs with a shorter linker (sCD4-20-17b and sCD4-5-17b) did not show potent neutralization (Lagenaur et al., *Retrovirology* 7:11, 2010) because the linker was too short to enable simultaneous binding, resulting in lower affinity.

Based on these findings, it was initially expected that a CD4-35-17b CAR would prove much more potent than a monofunctional CD4 CAR tested previously in clinical trials by other groups (Scholler et al. (2012) *Science Translational Medicine* 4(132); Mitsuyasu et al. (2000) *Blood* 96(3):785-793; Deeks, et al. (2002) *Molecular Therapy* 5(6):788-797; Walker et al. (2000) *Blood* 96(2):467-474), since the former targeting moiety would bind with much higher affinity to Env on target cells. Some data in the literature on T cell receptors (TCRs) indicated that higher avidity is associated with greater CTL efficacy ((Snyder et al. (2003) *Curr. HIV Res.* 1(3):287-294), which may be critical for control of HIV infection (Almeida et al. (2009) *Blood* 113(25):6351-6360; Mothe et al. (2012) *Plos One* 7(1)). However results from various in vitro assays indicated that CD4-35-17b CAR was no better than the corresponding CD4 CAR; in fact in some assays the potency was lower (FIGS. 2-5).

Figure 6A:
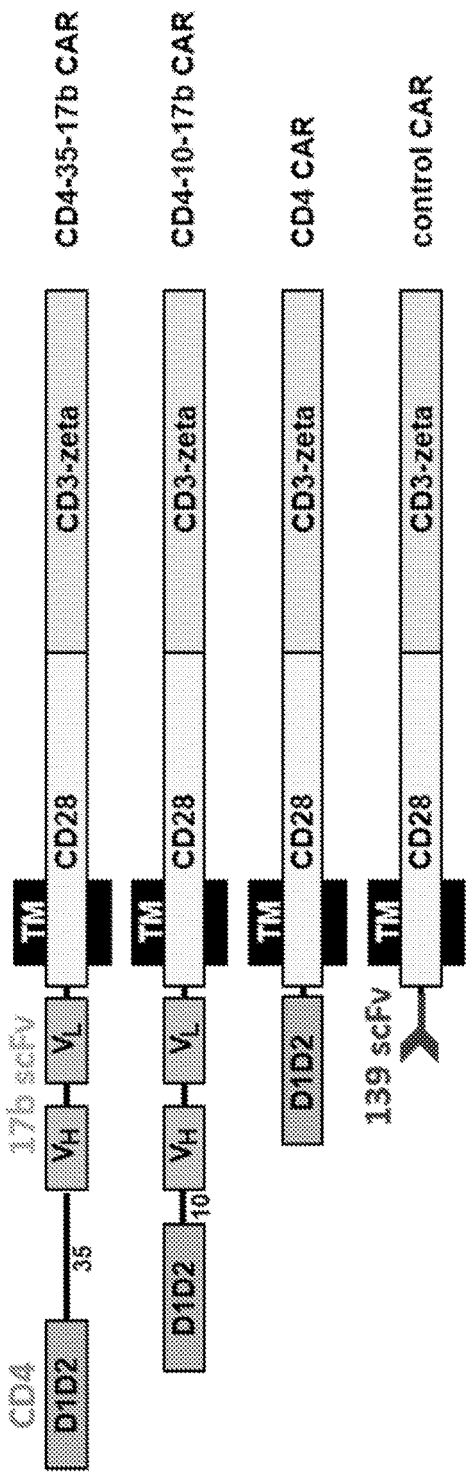
FIG. 6A is a schematic representation of various anti-HIV chimeric antigen receptors (CARs) expressed in a cell. These include CD4-17b constructs with long (CD4-35-17b) or short (CD4-10-17b) linkers between the CD4 and 17b scFv moieties, as well as two controls: the CD4-CAR and a negative control 139 scFv CAR directed against an irrelevant antigen not present in this experimental system (epidermal growth factor receptor variant III (EGFRvIII), Jones et al., *Human Gene Therapy,* 20:630-640, 2009, incorporated herein by reference); transmembrane and intracellular components are identical to those in the CD4-based CARs.
Figure 6B:
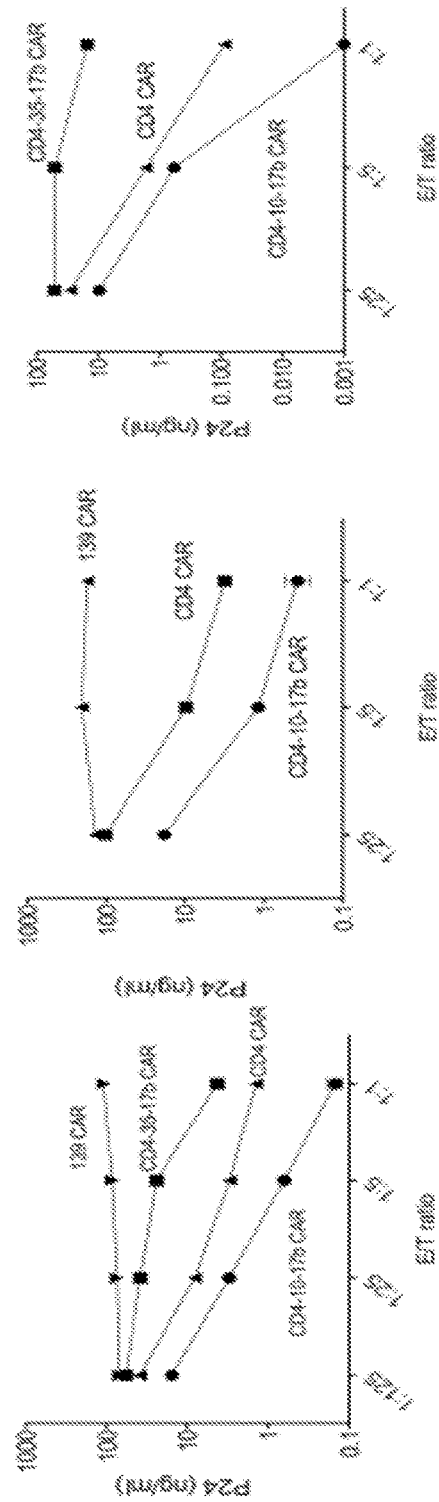
FIG. 6B is a series of line graphs illustrating suppression of HIV-1 infection of $CAR^+$ $CD8^+$ T cells expressing CARs with different CD4-based targeting segments. Monospecific or multispecific $CAR^+$ effector T cells (E) were incubated with HIV-1-infected human PBMC target cells (T) for 8 days. Supernatants were collected and p24 was quantified via ELISA as a measurement of HIV spread within culture. Data are shown for experiments with PBMC from three different donors (donor C, donor F, or donor G). All CD4-based CARs demonstrated suppression of HIV-1 infection; the levels were comparable to those of pseudovirus infection of the HOS-CD4-CCR5 cells (not shown). Based on the dose-response curves (varying E/T ratios), the CD4-10-17b CAR was consistently more potent than the CD4 CAR. By contrast, the CD4-35-17b CAR was consistently less potent than the CD4 CAR or the CD4-10-17b CAR.
Figure 7A:
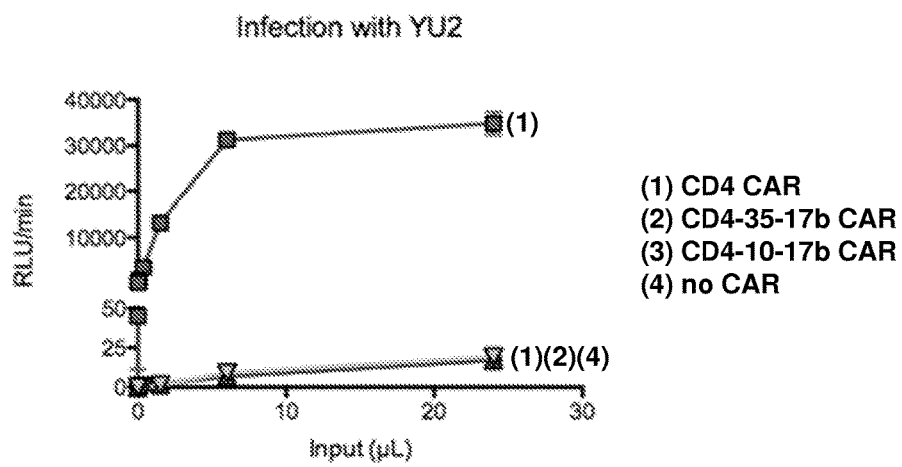
FIGS. 7A and 7B are a series of line graphs illustrating the comparison of different CD4-based CARs in rendering $CCR5^+$ cells susceptible to HIV-1 pseudovirus infection. $CCR5^+$ human osteosarcoma (HOS-CCR5) were transduced to express CD4 CAR, CD4-35-17b or CD4-10-17b CAR and mixed with the indicated pseudotyped HIV-1 Env particles (YU2 or Ba-L) to test for susceptibility to HIV-1 pseudovirus infection. The CD4 CAR renders CCR5-expressing cells susceptible to HIV-1 pseudotype infection (both isolates tested); by contrast, the CD4-35-17b and CD4-10-17b CARs did not render the CCR5-expressing cells susceptible to infection. The latter result was also obtained with a CAR composed of CD4 linked to an irrelevant scFV, i.e. no infection was observed. These results indicate that the scFv moiety intervening between the CD4 moiety and the membrane-proximal external region of the CAR construct prevented the CD4 moiety of the CAR from functioning as an HIV-1 entry receptor.
Figure 7B:
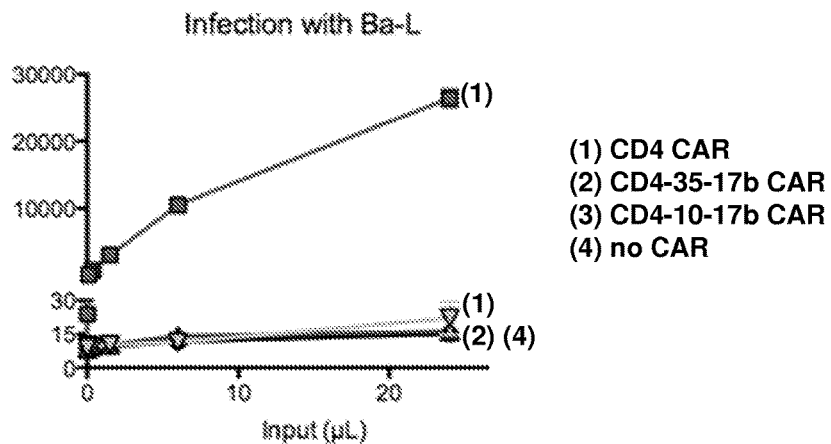
Figure 8:
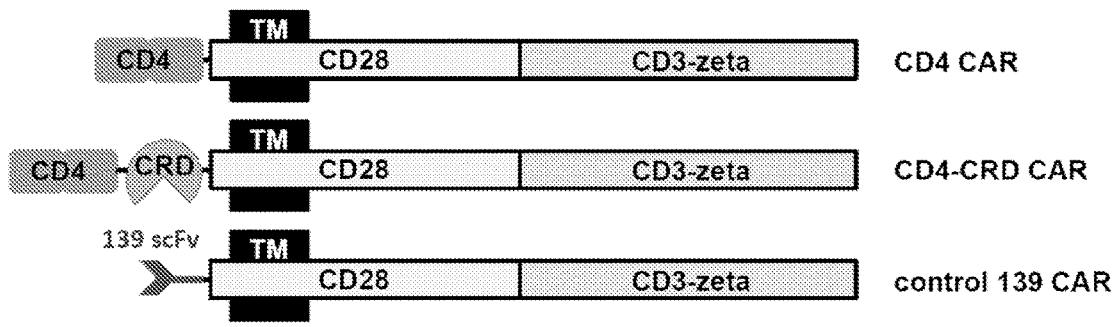
FIG. 8 is a schematic representation of additional CD4-based and control CAR constructs. As a variant of a previously known CD4 CAR (top), CD4-CRD CARs (middle) were designed that contain an N-terminal bifunctional targeting motif with the D1D2 segment of CD4, attached by a short polypeptide linker to the carbohydrate recognition domain (CRD) of a human lectin, for instance the CRD is derived from human DC-SIGN. A CAR in which the targeting motif is a scFv from mAb 139 (which recognizes an antigen not expressed on any of the cells used in our studies) was used as a negative control.
Figure 9:
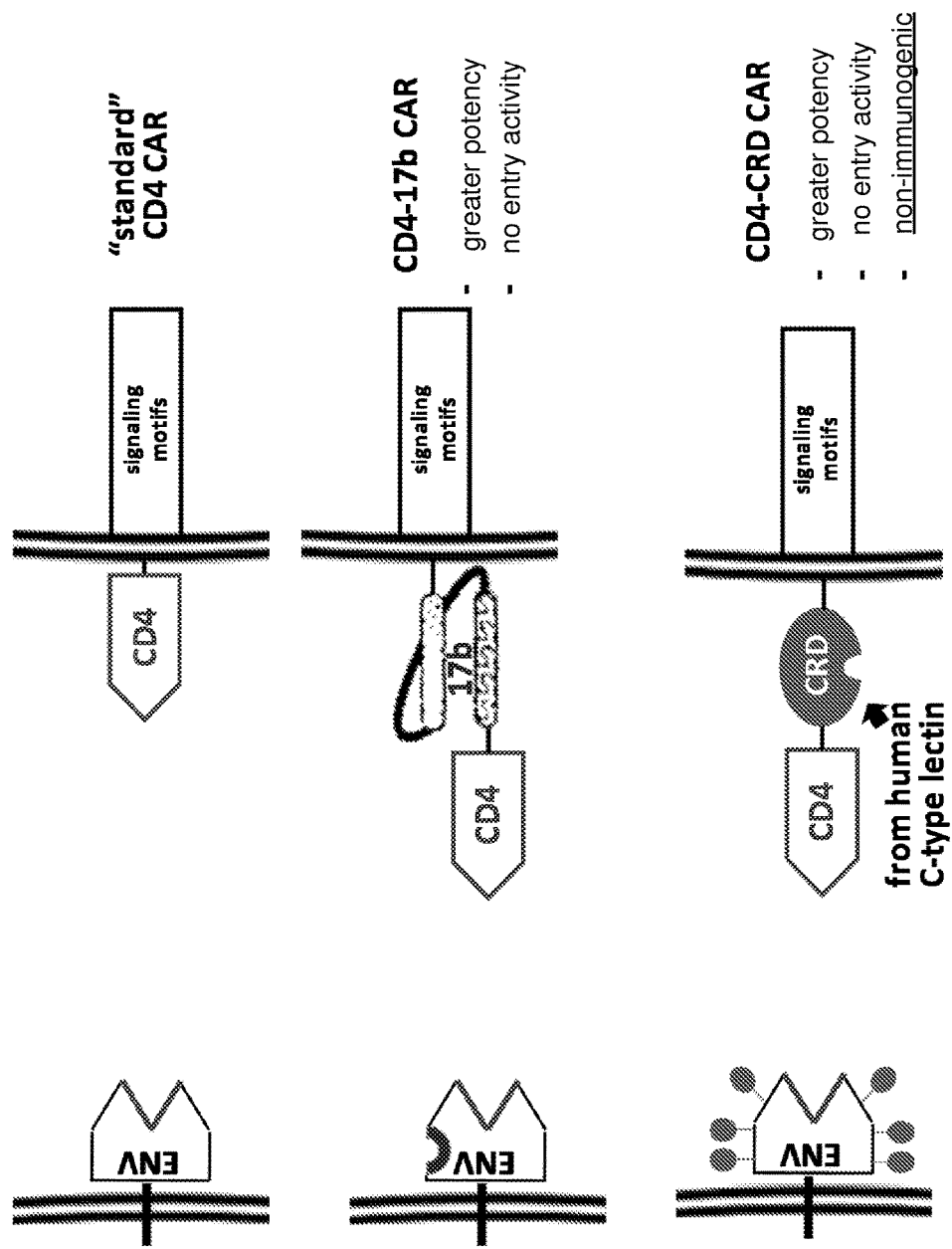
FIG. 9 is a schematic comparison of three CARs against HIV: a "standard" CD4 CAR, a CD4-mAb CAR (illustrated with CD4-17b CAR) and a CD4-CRD CAR (illustrated with a CRD from a human C-type lectin, such as DCSIGN).
Figure 10:
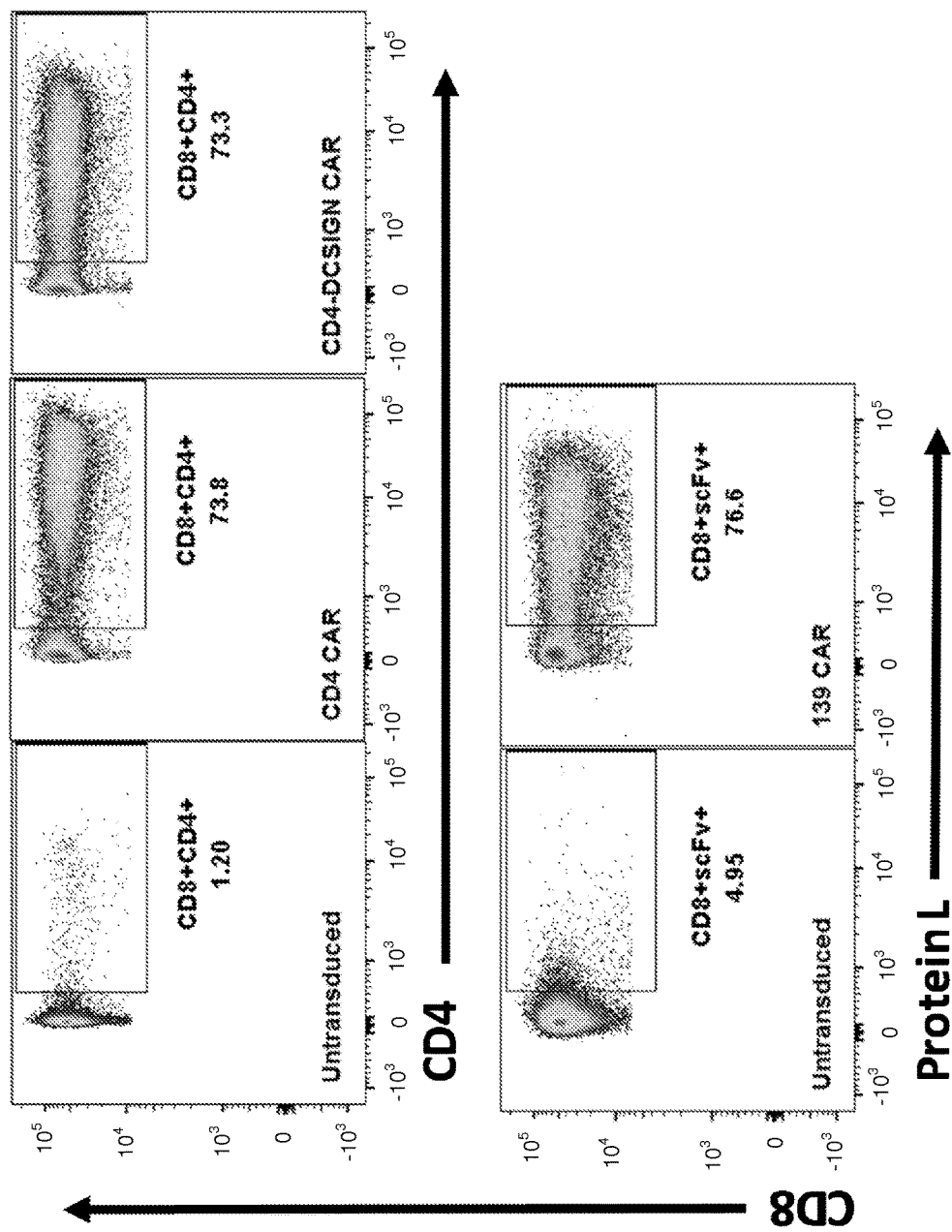
FIG. 10 shows expression of indicated CARs on CD8+ T cells. CD8+ T cells isolated from PBMC of healthy donors were transduced with retroviral vectors encoding the indicated CAR constructs. After expansion, the cells were characterized by flow cytometry, with untransduced cells as controls. CD4-based CAR expression was evaluated by staining for CD8+ and CD4. 139 CAR was detected by staining with Protein L-biotin followed by Streptavidin-PE. Upper panels: Both the CD4 CAR and the CD4-DCSIGN CAR were efficiently expressed on the CD8+ T cells (>73-86% in this experiment; staining on X axis with anti-CD4 mAb RPA-T4). Lower panels: Similar transduction efficiency was obtained with the control 139 CAR (80%; staining on X axis with Protein L).
Figure 11A:
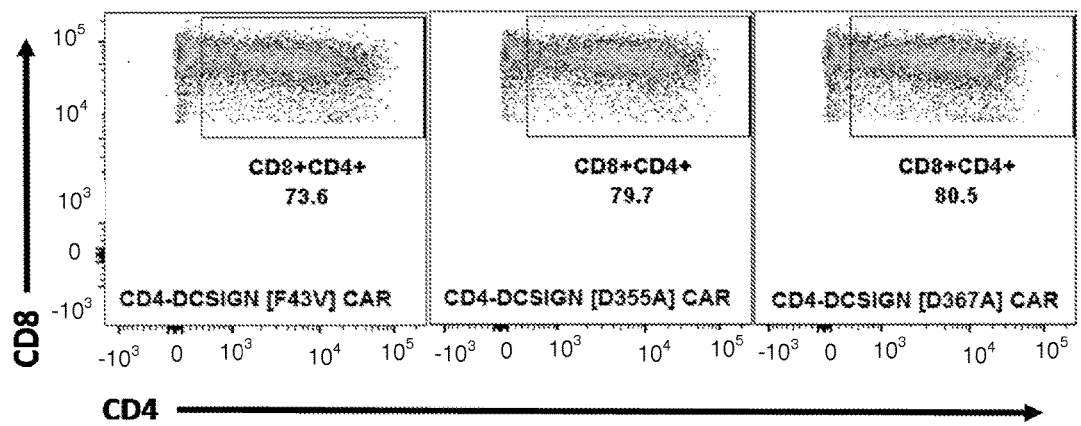
FIG. 11A shows expression of CD4-DCSIGN CAR mutants. Gated on CD8+ cells. CD4-based CAR expression was evaluated by staining for CD8 and CD4.
Figure 11B:
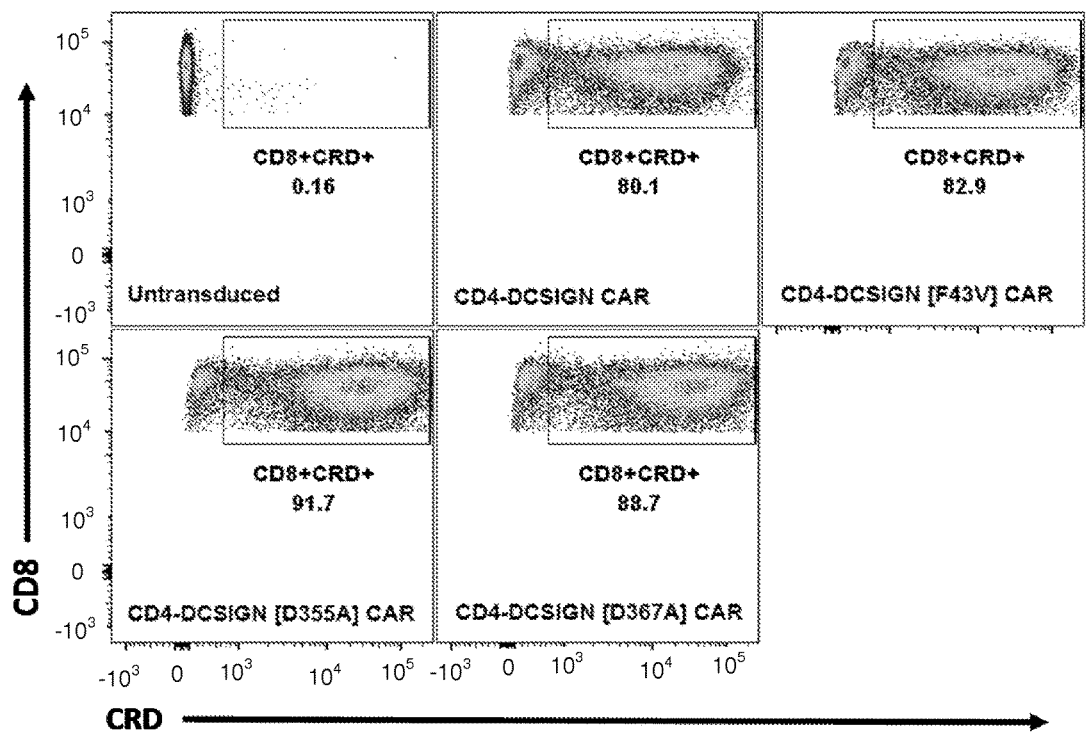
FIG. 11B shows expression of CD4-DCSIGN CAR using mAb 120526 against DCSIGN CRD. Gated on CD8+ cells. CAR expression was evaluated by staining for CD8 and DCSIGN-CRD.

High affinity binding may be detrimental to CAR potency, since the tight binding prevents the receptor disengagement and rebinding; such "serial triggering" may be critical for optimal function of TCRs and may also apply to CARs. Thus, the CD4-17b construct was redesigned in which the linker was deliberately too short to enable simultaneous binding of the sCD4 and 17b moieties. A CD4-10-17b CAR was engineered. In repeat assays of suppression of HIV infection of PBMC, the CD4-10-17b CAR proved significantly more potent than the CD4 CAR and the CD4-35-17b CAR (FIG. 6).

Figure 13A:
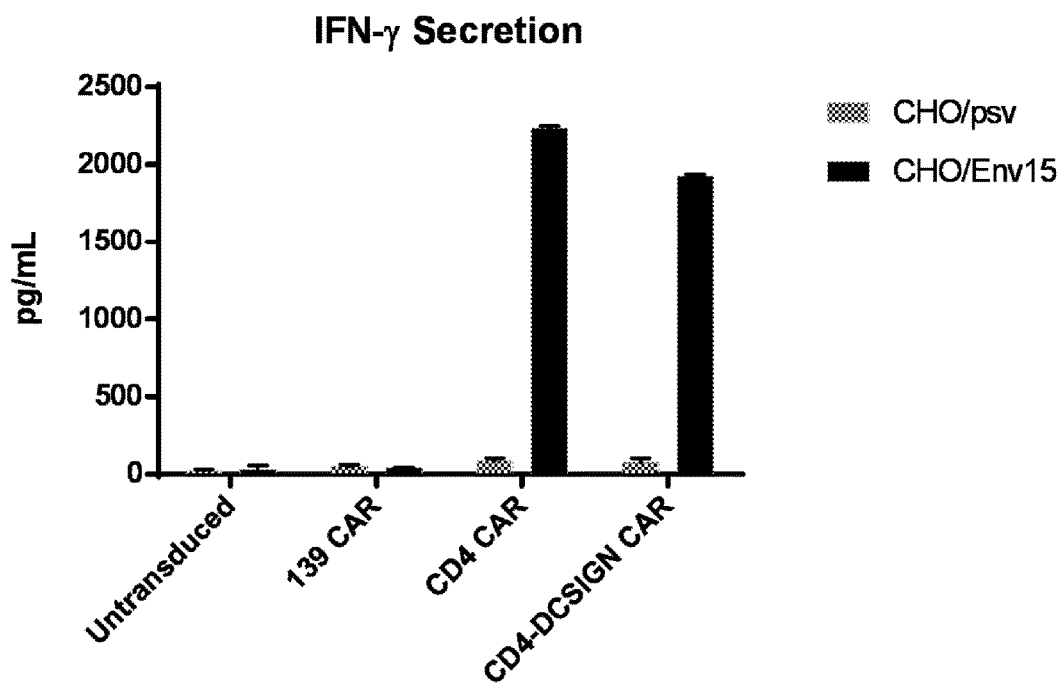
FIG. 13A shows stimulation of IFN-γ from T cells expressing different CARs and dependence on antigen expression on target cells. The HIV-1 Env-expressing stable transfectant target cells (CHO/Env) stimulated efficient IFN-γ secretion during coculture with T cells expressing the CD4 and CD4-DCSIGN CARs, but not with control T cells (untransduced or expressing the 139 CAR). The control Env-negative parental target cells (CHO/psv) had no effect. Thus both CD4-based CARs mediated potent antigen-induced cytokine secretion responses.
Figure 13B:
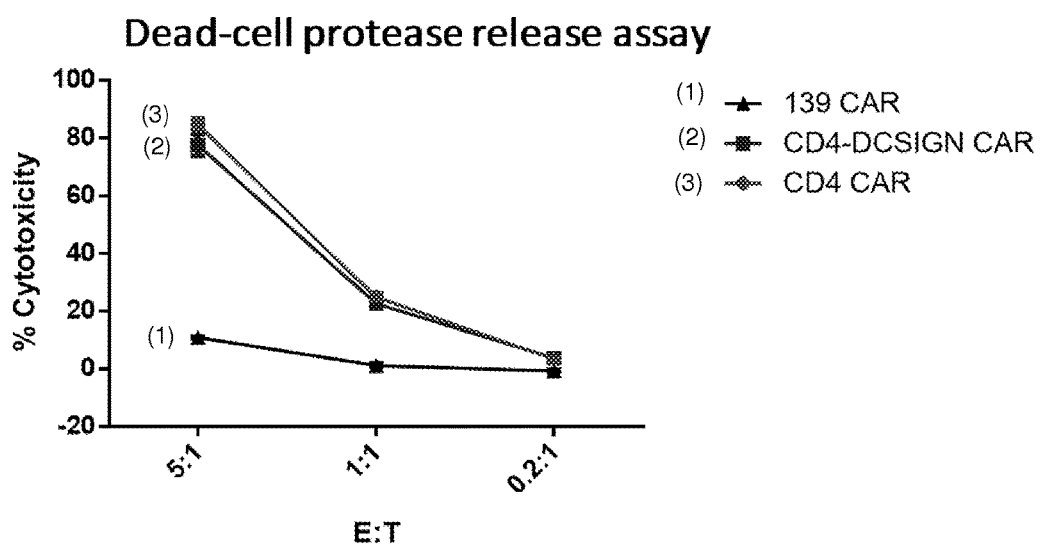
FIG. 13B shows direct killing of HIV-1 Env-expressing target cells by CAR-expressing T cells. CHO/Env15 target cells were co-cultured for 4 hr with T cells expressing the indicated CAR. Cytotoxicity was assessed by measuring protease activity released from lysed target cells (Promega CytoTox-Glo™ cytotoxicity assay kit). The CD4 and CD4-DCSIGN CARs mediated potent killing of the Env-expressing target cells; minimal killing occurred with the control 139 CAR.

Thus, in the optimal CAR construct, the CD4 and M2 elements should each bind to sites on Env, but not simultaneously. In this way, as the CD4 moiety of one CAR molecule and the M2 moiety of a different CAR molecule bind, only one moiety is binding on each CAR molecule, resulting in more opportunity to disengage and re-bind (serial triggering). Moreover, a single gp120 subunit can simultaneously be engaged by two separate CAR molecules, one via CD4 and the other via the 17b moiety.

Example 2

Ability of Different CD4-Based CARs in Rendering $CCR5^+$ Cells Susceptible to HIV-1

This example describes an in vitro assay to measure the susceptibility of $CCR5^+$ cells to cells expressing a CD4-17b CAR.

Inhibition of Primary HIV-1 Spreading Infection by CAR-T Cells

Frozen autologous PBMCs were rapidly thawed and suspended with a density of $2\times10^6$ cells/ml in RPMI-1640 medium containing 20% FBS, 32 IU/ml IL-2 and 50 μg/ml PHA. 2 ml of cell suspension were added to each well on a 24 well plate and incubated at 5% $CO_2$, 37° C. overnight. The next day, cells were collected and resuspended with fresh medium without PHA. After 2-3 day of culture, cells were resuspended in RPMI-1640 medium (containing 20% FBS, 32 IU/ml IL-2) at a $5\times10^6$/ml and were transferred to a T25 flask. 1 ml of HIV virus (isolate BX08, 150 ng/ml P24) was then added. After addition of virus, cells were incubated at 37° C., 5% $CO_2$ overnight. Infected cells were spun down at 300 g for 10 minutes. After removal of the supernatant, 20 ml of medium was added to wash the cells. After washing three times, cells were resuspended in complete medium (RPMI-1640, 20% FBS and 32 IU/ml IL-2) with a density of $1.5\times10^6$ cells/ml. Subsequently, 100 μl of infected PBMCs were mixed with 100 μl of CAR-T cells at various E/T ratios in quadruplicate. Co-culture was carried on in the 96-well round bottom plate at 37° C., 5% CO2 for 8 days. Supernatants were then collected and the production of progeny virions was measured by p24 ELISA (Perkin Elmer).

Results $CD8^+$ cells naturally express the CCR5 co-receptor, suggesting the possibility that expression of a monofunctional CD4 CAR might render them sensitive to HIV infection, particularly since during their proposed killing function, they become intimately associated with infected cells, creating the optimal condition for enhanced infection at the "virological synapse" (Sattentau *Current Opinion in Virology* 1(5):396-402, 2011). The ability of a monofunctional CD4 CAR versus the CD4-17b CARs to render CCR5-expressing cells susceptible to infection by HIV-1 pseudotype viruses was compared (FIG. 7).

The data in FIG. 7 clearly show that the CD4 CAR rendered transfectant HOS-CCR5 cells susceptible to HIV-1 pseudotype infection. However, the CD4-35-17b CAR was completely devoid of this unwanted activity. This was also the case for CD4-17b CARs with shorter linkers. Similar results were also seen with primary human CD8 T cells. The protective effect of the 17b scFv moiety was also seen with control scFv moieties, indicating non-specific, rather than being due to a gp120 binding/neutralization mechanism.

Example 3

Method for Treating a Subject Having an HIV Infection

This example describes methods that can be used to treat a subject having an HIV infection. However, one skilled in the art will appreciate based on the teachings herein that methods that deviate from these specific methods can also be used to successfully treat a subject having an HIV infection.

In an example, a subject who has been diagnosed with an HIV infection is identified. Following subject selection, a therapeutically effective amount of $CD8^+$ T cells expressing a multispecific CAR is administered to the subject. In one specific, non-limiting example, a therapeutically effective amount of $CD8^+$ T cells expressing a CD4-10-scFv17b CAR is administered to the subject. The amount of the $CD8^+$ T cells expressing a CD4-10-scFv17b CAR administered to treat the HIV infection depends on the subject being treated, the severity of the disorder, and the manner of administration of the therapeutic composition. Ideally, a therapeutically effective amount of $CD8^+$ T cells expressing a CD4-10-scFv17b CAR is the amount sufficient to inhibit the condition (e.g., HIV infection) in a subject without causing a substantial cytotoxic effect in the subject.

A reduction in the clinical symptoms associated with HIV infection, for example, decreased number of cells infected with HIV in the subject, indicates the effectiveness of the treatment.

Example 4

Chimeric Antigen Receptors Based on CD4 Linked to a Carbohydrate-Recognition Domain A highly promising strategy in the cancer field includes targeted killing of cancer cells by ex vivo engineering a patient's T cells to express a chimeric antigen receptor (CAR) targeting an antigen over-expressed on cancer cells. This strategy is potentially readily adaptable to infectious diseases including HIV, using a CAR that targets a virus-encoded molecule (e.g., HIV-Env) that is expressed on the surface of infected cells. Application of CAR strategies to HIV and other infectious diseases has the distinct advantage that the target molecule is specific to the virus, hence avoiding the problem often encountered in cancer applications involving undesired killing of normal cells that express the target molecule, even at lower levels compared to the cancer cells.

A CAR is a genetically engineered single chain construct consisting of a targeting motif (e.g. scFV, ligand) that recognizes the native target molecule expressed on the surface of the infected cell; this is linked to a transmembrane domain and to intracellular signaling motifs derived from the T cell receptor (e.g. from the zeta chain); newer generation CARs also include in the same construct signaling motifs from one or more co-stimulatory molecules (e.g. CD28, 41BB). When $CD8^+$ T cells are transduced with the CAR genes, the CAR molecules recognize the native target molecule on the infected cells, resulting in their killing by the transduced $CD8^+$ T cells.

As described below and herein, CARs have been designed that have an ectodomain containing a novel targeting motif against the HIV Env glycoprotein. Specifically, the targeting motif includes extracellular regions of human CD4 containing the gp120 binding region in domain 1, attached by a polypeptide linker to the carbohydrate recognition domain (CRD)-containing domains of a lectin (such as a human C-type lectin) that recognize glycans displayed on the HIV Env glycoprotein. By way of example, the CRD is derived from human proteins DC-SIGN or L-SIGN, which bind high mannose glycans displayed at multiple sites on the surface of the gp120 subunit of Env; DC-SIGN is thought to be an attachment receptor that facilitates infection by transferring HIV virions from dendritic cells to T cells. Also demonstrated are CARs that include CD4 and the CRD from Langerin or from MBL2. This type of CAR is illustrated schematically in FIG. 9, in comparison to a "standard" CD4 CAR as well as a CD4-scFv CAR such as those described and analyzed in Examples 1-3.

Compared to CARs consisting of CD4 alone as the targeting moiety, CD4-CRD CARs have a number of advantages, including (though these statements are not intended to be limiting):

1. Greater potency, which is proposed to be due to the recognition of Env by two independent moieties that recognize distinct highly conserved sites on Env, i.e., the CD4 binding site on gp120 and high mannose glycans. Based on previous findings with other CARs containing the CD4 moiety linked to scFvs recognizing conserved epitopes on gp120, we believe it is not essential for a single CAR molecule to bind the same gp120 subunit via both the CD4 and CRD motifs; in fact this may be detrimental, since the resulting high-affinity dual binding may prevent "serial triggering" that is known to be important for optimal T cell activation. Hence the linker between the CD4 and the CRD need not be sufficiently long to enable such simultaneous binding to both sites on a single gp120 subunit; instead, if the linker is too short for such simultaneous binding, then a single gp120 will be capable of engaging two or more CAR molecules, and the affinity will be sufficiently modest to enable serial triggering.
2. The presence of the CRD moiety prevents the CD4 motif of the CAR from acting as an entry receptor. "Standard" CD4 CAR renders $CD8^+$ T cells susceptible to HIV-1 infection ($CD8^+$ T cells also express surface CCR5); by contrast, the CD4-DCSIGN CAR does not exhibit this undesirable activity.

Example 5

Expression of CRD-Containing CARs $CD8^+$ T cells isolated from PBMC of healthy donors were transduced with retroviral vectors encoding the indicated CAR constructs shown in FIG. 10. After expansion, the cells were characterized by flow cytometry, with untransduced cells as controls (FIG. 10). CD4-based CAR expression was evaluated by staining for CD8 and CD4 (using anti-CD4 antibody RPA-T4, eBiosciences). 139 CAR was detected by staining with Protein L-biotin followed by Streptavidin-PE. Upper panels of FIG. 10: Both the CD4 CAR and the CD4-DCSIGN CAR were efficiently expressed on the CD8 T cells (>73-86% in this experiment; staining on X axis with anti-CD4 mAb). Lower panels of FIG. 10: Similar transduction efficiency was obtained with the control 139 CAR (80%; staining with Protein L).

FIG. 11A shows expression of CD4-DCSIGN CAR mutants with the following amino acid substitutions: F43V, D355A, and D367A. The FACS analysis was gated on CD8+ cells. CD4-based CAR expression was evaluated by staining for CD8 and CD4 [using the RPA-T4 anti-CD4 antibody]. Good expression was achieved with all three mutants.

FIG. 11B shows expression of CD4-DCSIGN CAR and mutants (as in FIG. 11A) using mAb 120526 against DCSIGN CRD. The FACS analysis was gated on CD8+ cells. CAR expression was evaluated by staining for CD8 and DCSIGN-CRD. DCSIGN-CRD was detected using Clone 120526 (Jameson et al., *J Virol* 76:1866-1875, 2002), obtained through the NIH AIDS Reagent Program, Division of AIDS, NIAID, NIH: DC-SIGN Monoclonal Antibody (Clone 120526). Good expression was achieved with all constructs.

FIG. 12A shows expression of CD4-based CARs with CRDs from other human C-type lectins. The FACS analysis was gated on CD8+ cells. CD4-based CAR expression was evaluated by staining for CD8 and CD4 [RPA-T4]. Very good expression was achieved for all three additional CRD CARs (CD4-LSIGN CAR, CD4-Langerin CAR, and CD4-MBL2 CAR).

FIG. 12B shows the crystal structures of CRDs of closely related human mannose-binding lectins, each of which has been used as a component in a CAR described and characterized herein. (DC-SIGN, PDB 2IT5: Feinberg et al., *J. Biol. Chem.* 282: 4202-4209, 2007; DC-SIGNR, PDB 1K9J, DC-SIGNR: Feinberg et al., *Science* 294: 2163-2166, 2001; MBL, 1HUP: Sheriff et al., *Nat. Struct. Biol.* 1: 789-794, 1994).

Example 6

Specific Activity of CRD-Containing CARs

The properties of the CD4-DCSIGN CAR and a "standard" CD4 CAR were compared in various assays, using retroviral vectors encoding the corresponding CAR constructs; untransduced cells and/or the 139 scFv CAR served as negative controls. FIG. 8 provides a schematic representation of these three types of CARs. All three constructs are so-called "second generation" CARs, i.e. they are attached to two signaling motifs, in these embodiments the hinge, TM, and intracellular regions of CD28 followed by the intracellular region of the CD3 zeta chain at the C-terminus.

CHO/IFN-γ

Effectors were co-cultured with CHO cells in a 96-well round bottom plate overnight; @ $50\times10^3$ effectors:$50\times10^3$ target cells per well in triplicate. Culture supernatants were diluted 1:5 for the IFN-γELISA using ThermoScientific Prod # EHIFNGS. FIG. 13A shows stimulation of IFN-γ from T cells expressing different CARs and the dependence on antigen expression on target cells. The HIV-1 Env-expressing stable transfectant target cells (CHO/Env) stimulated efficient IFN-γ secretion during coculture with T cells expressing the CD4 and CD4-DCSIGN CARs, but not with control T cells (untransduced or expressing the 139 CAR). The control Env-negative parental target cells (CHO/psv) had no effect. Thus both CD4-based CARs mediated potent antigen-induced cytokine secretion responses.

CHO/CytoTox Glo

Effectors were co-cultured with CHO-Env15 cells over an incubation period of 4 hrs in a white-wall flat bottom 96-well plate. One unit represents 10,000 cells/well. The culture supernate was analyzed for protease release due to cell-mediated cytotoxicity using the Promega CytoTox-Glo™ cytotoxicity assay kit. The assay was performed in triplicate and the values are corrected for spontaneous signal due to media and background protease activity.

FIG. 13B shows direct killing of HIV-1 Env-expressing target cells by CAR-expressing T cells. CHO/Env15 target cells were co-cultured for 4 hrs with T cells expressing the indicated CAR. Cytotoxicity was assessed by measuring protease activity released from lysed target cells (Promega CytoTox-Glo™ cytotoxicity assay kit). The CD4 and CD4-DCSIGN CARs mediated potent killing of the Env-expressing target cells; minimal killing occurred with the control 139 CAR.

HeLa-TetOff/IFN-γ

Figure 14A:
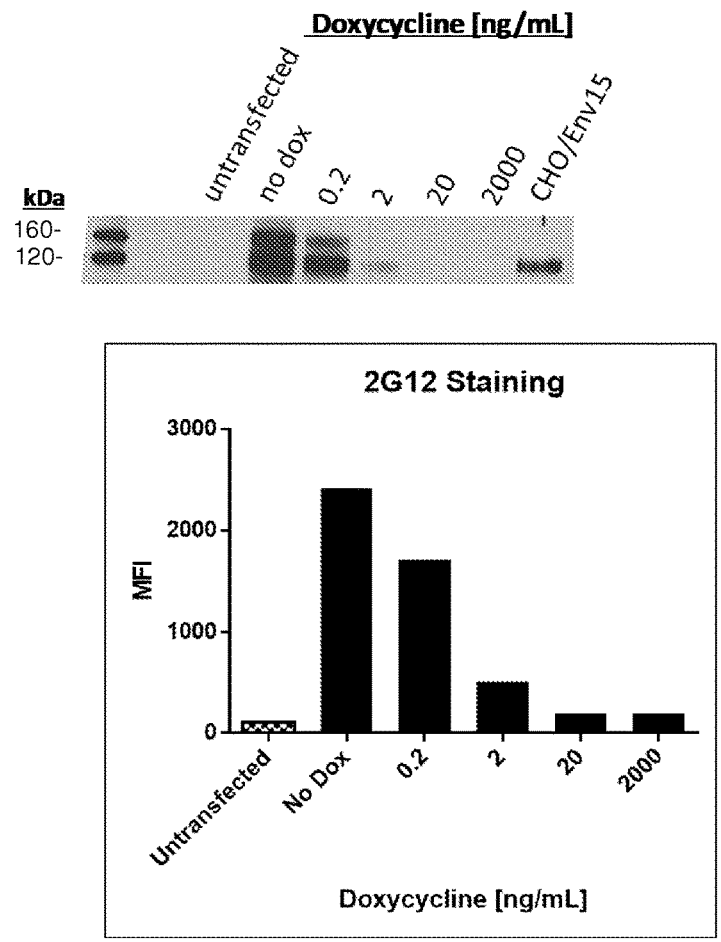
FIGS. 14A and 14B show that CAR-expressing CD8+ T cells are responsive to target cells expressing very low levels of Env, as shown with doxycycline-regulated system.

FIG. 14A shows regulation of HIV-1 Env expression by doxycycline in HeLa-TetOff cells transfected with the inducible Env plasmid pGL4.22-JRFL (Herschhorn et al., *PLoS ONE* 6(11): e26731. doi:10.1371/journal.pone.0026731, 2011). The cells were treated with the indicated amounts of doxycycline and assayed for Env expression by Western blot (FIG. 14A, top panel) and flow cytometry (FIG. 14A, bottom panel) using the Env-specific 2G12 mAb. CAR-expressing $CD8^+$ T cells are responsive to target cells expressing very low levels of Env, as shown with doxycycline-regulated system.

Figure 14B:
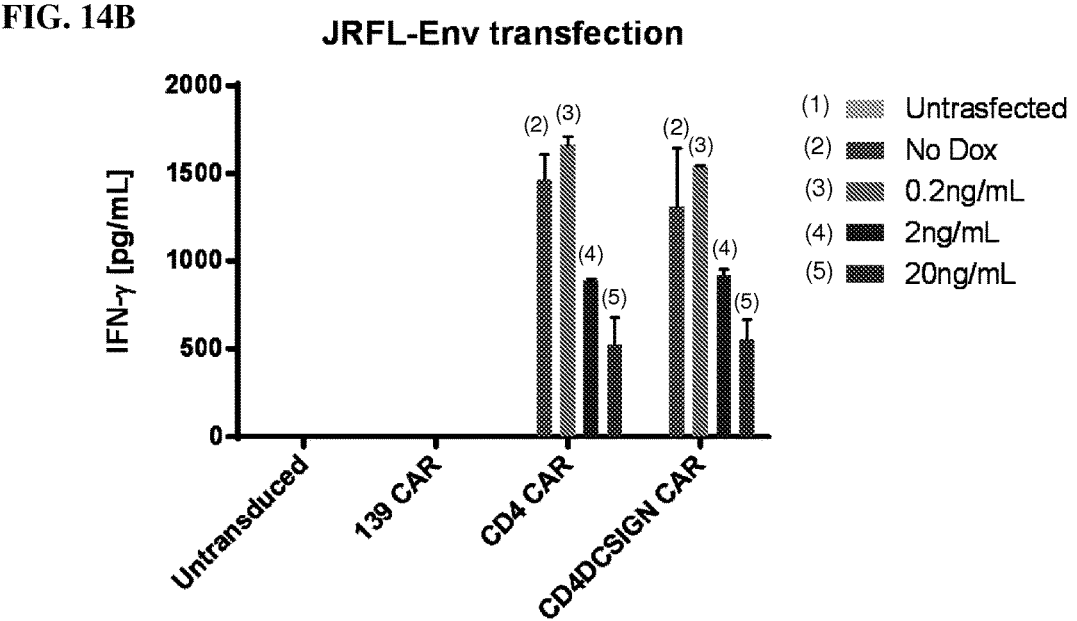

FIG. 14B shows that CD4-based CARs render T cells highly responsive to target cells expressing Env, even at very low levels. The HeLa-Tet-Off system was used to express varying levels of HIV-1 Env (JR-FL) introduced by plasmid transfection followed by incubation for 24 hrs in the presence of the indicated concentrations of doxycycline (which represses Env expression). During a 4 hr coculture, the CD4 and CD4-DCSIGN CARs mediated IFN-γ secretion from target cells expressing varying levels of Env.

At the highest expression level (No Dox), Western blots indicated pronounced gp120 expression whereas at the lowest expression level (20 ng/ml Dox), gp120 was barely detected. The level of IFN-γ secretion was quite robust (~30%) even at the lowest Env expression level, indicating the high responsiveness of the CAR-expressing T cells.

293T/IFN-γ

Figure 15A:
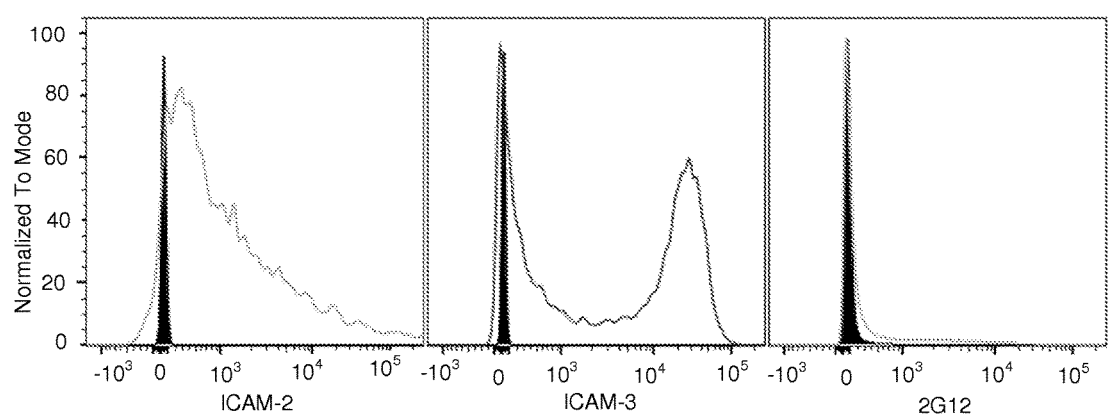
FIGS. 15A and 15B show absence of CAR activity against cells expressing natural DC-SIGN ligands (ICAMs).
Figure 15B:
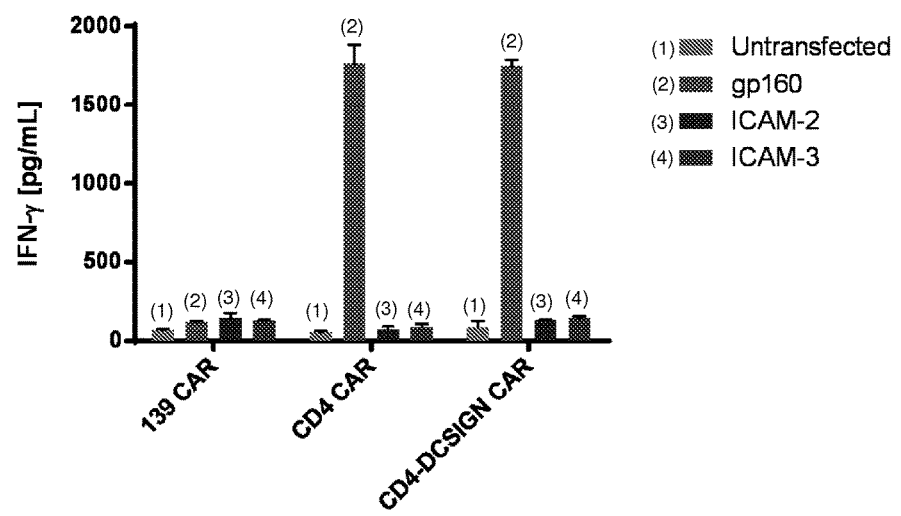

ICAM-2 and ICAM-3 were obtained from Addgene, contributor Timothy Springer, de et al. (*J Exp Med.* 175(1): 185-90, 1992); gp160 was obtained from the AIDS Repository, contributor Beatrice Hahn. 293T cells were individually transfected with expression constructs encoding ICAM-2 (left), ICAM-3 (middle), or HIV-1 Env (gp160, right) and analyzed for surface expression of the transgene by flow cytometry (FIG. 15A). FIG. 15B shows the amount of IFN-γ expressed by transfected 293T cells. 293T cells were seeded at $10^4$/well in a 96-well plate overnight and transfected the following day using FugeneHD with the indicated genes. After two days, the media was aspirated from each well and replaced with 100 μL fresh media containing $10^3$ effectors. The plate was incubated overnight, and the following day the media was analyzed using IFN-γ ELISA (Thermo EHIFNG kit). FIGS. 15A & 15B illustrate the absence of CAR activity against cells expressing natural DC-SIGN ligands (ICAMs).

Example 7

Permissiveness to Infection

Susceptibility of CAR-Transduced CD8 T Cells to Pseudovirus Infection

Figure 16A:
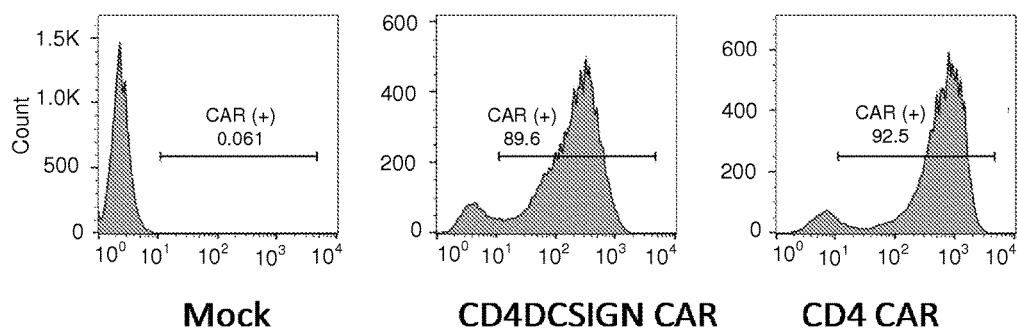
FIGS. 16A and 16B illustrate the susceptibility of CAR-transduced CD8+ T cells to HIV-1 pseudovirus infection.

HOS.CCR5 cells were transduced with the indicated CAR gene and analyzed for CAR surface expression by flow cytometry using anti-CD4 [RPA-T4] (FIG. 16). CAR-transduced HOS.CCR5 cells were cultured in 96-well white wall plates in the presence of varying dilutions of either of two HIV-Luc pseudovirus particles (BaL and YU2 envelopes) and assayed for luciferase activity 48 hrs post-infection. Untransduced HOS.CCR5 and HOS.CD4.CCR5 cells are included as negative and positive controls, respectively.

Figure 16B:
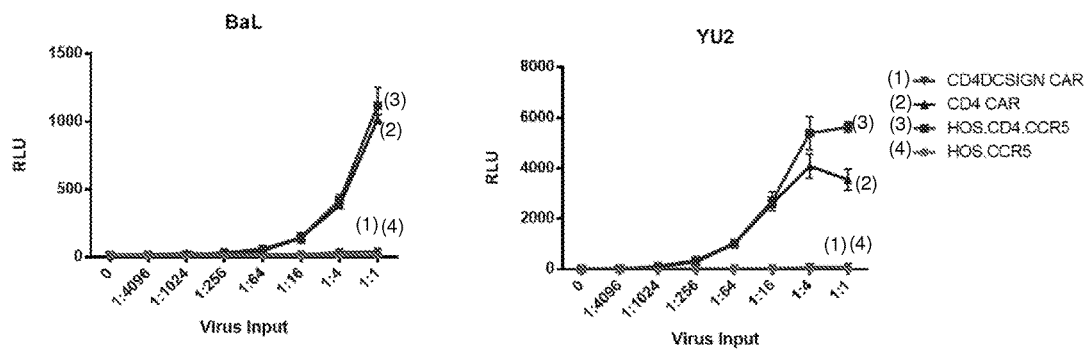

Whether expression of the CD4-based CARs on a stable CCR5 transfectant cell line (HOS-CCR5) rendered the cells susceptible to luciferase-encoding pseudovirus particles displaying HIV-1 Env (FIG. 16B; YU2, left; BaL, right) was tested. The data shown that for both pseudoviruses, the "standard" CD4 CAR indeed rendered the cells highly susceptible, in fact to a degree comparable to the stable HOS-CD4-CCR5 double transfectant cell line. By contrast, the CD4-DCSIGN CAR displayed no such susceptibility, equivalent to the HOS-CCR5 cells not expressing a CAR.

CD4-DCSIGN CAR Expression does not Render Cells Susceptible to HIV-1 Infection

CD4-based CARs, while potentially effective at suppressing HIV infection, may render the expressing effector $CD8^+$ T cells susceptible to HIV infection. The known expression of CCR5 on $CD8^+$ T cells highlights the significance of this concern. We assessed this potential, for both the "standard" CD4 CAR and the CD4-DCSIGN CAR.

Figure 17:
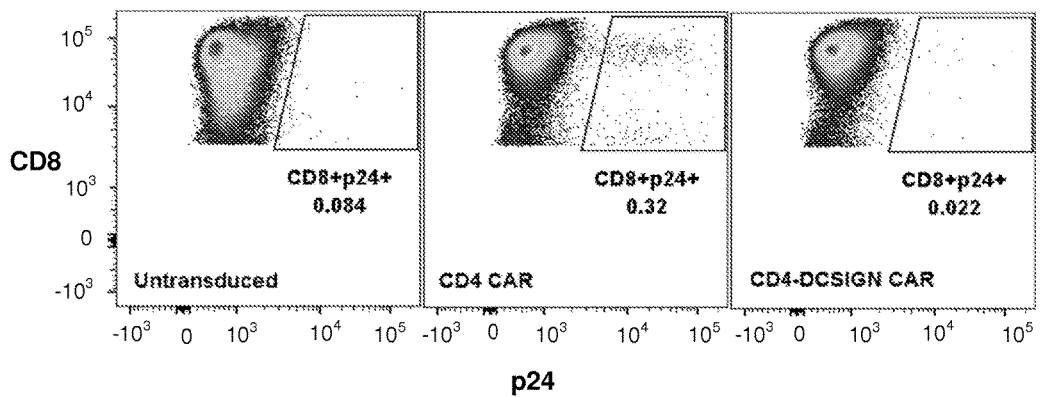
FIG. 17 illustrates permissiveness of CAR-transduced CD8+ T cells to infection by HIV-1. As a second approach, we tested whether expression of CD4-based CARs rendered CD8+ T cells susceptible to HIV-1 infection.

We tested whether expression of CD4-based CARs rendered CD8 T cells susceptible to HIV-1 infection. FIG. 17 shows that the "standard" CD4 CAR did confer HIV-1 susceptibility, whereas the CD4-DCSIGN CAR did not. $CD8^+$ T-cells were isolated from PBMCs by MACS negative selection (Miltenyi Biotec). The cells were activated and transduced with the indicated CAR genes. Cell free HIV (BaL isolate) was added to the cultures and the cells were analyzed for infection by intracellular p24 staining three days later (using anti-HIV-1 Core Antigen Ab clone KC57, Beckman Coulter).

The CD4-DCSIGN CAR was devoid of the undesired activity seen with the "standard" CD4 CAR of rendering coreceptor-positive cells susceptible to HIV-1 infection.

Spreading Infection Assays

Frozen autologous PBMCs were rapidly thawed and suspended at a density of $2\times10^6$/ml in RPMI-1640 medium containing 20% FBS, 32 IU/ml IL-2 and 50 μg/ml PHA. 2 ml of cell suspension were added to each well on a 24 well plate and incubated at 5% CO2, 37° C. overnight. The next day, cells were collected and resuspended with fresh medium without PHA. After 2-3 days of culture, cells were resuspended at 5×106/ml of RPMI-1640 medium (containing 20% FBS, 32 IU/ml IL-2) and transferred to a T25 flask. 1 ml of primary HIV isolate stock (P24 titer of 50-150 ng/ml) was then added to each flask and the cells were incubated at 37° C., 5% $CO_2$ overnight. Infected cells were spun down at 300 g for 10 min. After removal of the supernatant, cells were washed 3 times using 20 ml of medium per wash and the resuspended in complete medium (RPMI-1640, 20% FBS and 32 IU/ml IL-2) at a density of $1.5\times10^6$ cells per ml. Subsequently, 100 μl of infected PBMCs were mixed with 100 μl of serially diluted CAR-transduced T cells to obtain various E/T ratio (as indicated in the figures) in duplicates. Co-cultures were carried on in the 96-well round bottom plate at 37° C., 5% $CO_2$ for 8 days. Supernatants were then collected and the production of progeny virions in each co-culture supernatant was measured by P24 ELISA (Perkin Elmer).

Figure 18A:
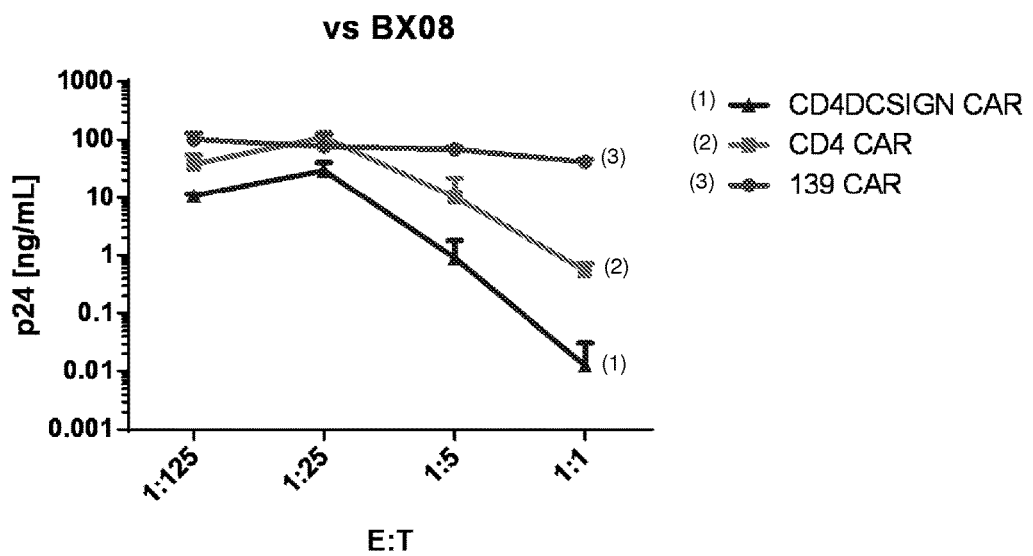
FIGS. 18A and 18B illustrate testing of CARs in PBMC/HIV spreading infection experiments. The data show that the CD4-DCSIGN CAR was effective at suppressing HIV-1 for both the BX08 isolate (FIG. 18A) and the BaL isolate (FIG. 18B); in both cases, the potency was greater than that observed with the "standard" CD4 CAR.
Figure 18B:
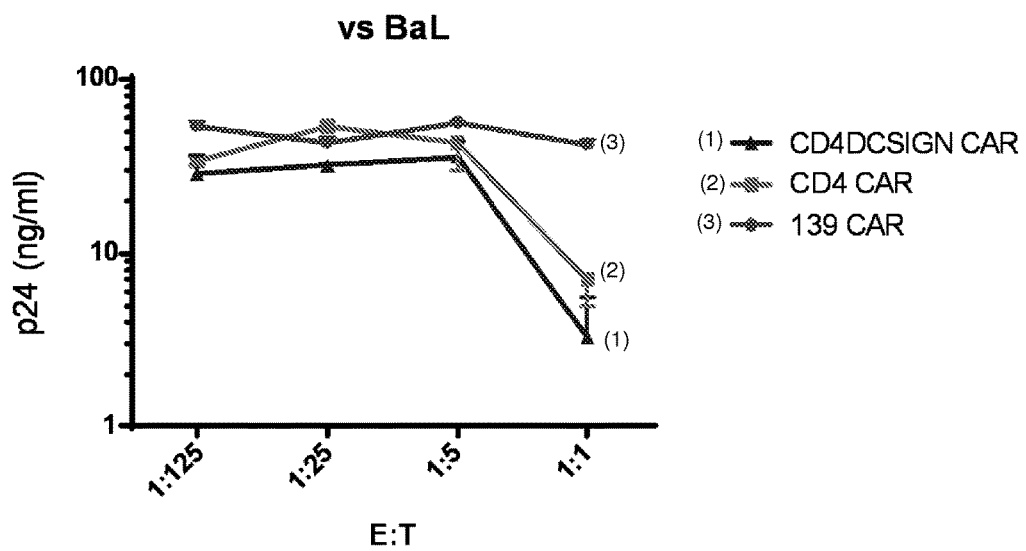

FIGS. 18A & 18B illustrate testing of CARs in PBMC/HIV spreading infection experiments. The data show that the CD4-DCSIGN CAR was effective at suppressing HIV-1 for both the BXO8 isolate (FIG. 18A) and the BaL isolate (FIG. 18B); in both cases, the potency was greater than that observed with the "standard" CD4 CAR.

Mutants

Figure 19A:
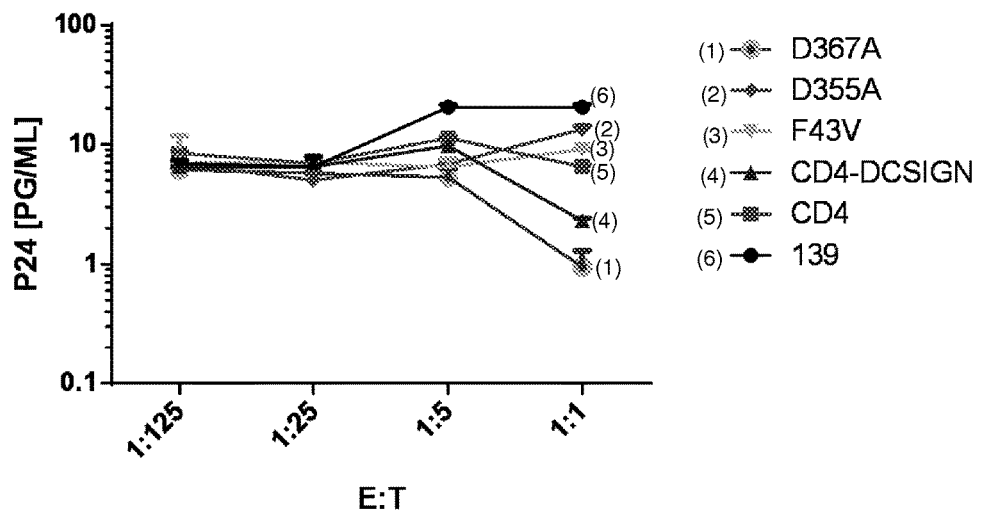
FIGS. 19A and 19B are a pair of graphs illustrating that the CD4 moiety plays a critical role in the function of the CD4-DCSIGN CAR and the enhancing role of the glycan-binding activity of the DCSIGN CRD component. In CD4, the F43V mutation is known to block binding to gp120. The data in FIG. 19 show that this mutation completely abrogates the function of the CD4-DCSIGN CAR for both the BX08 (FIG. 19A) and the BaL (FIG. 19B) isolates. In DC-SIGN, the D355A mutation blocks binding to high mannose glycans, whereas the D367A enhances binding. In the CAR constructs, these mutations inhibited and enhanced CAR function, respectively, for both the BX08 (FIG. 19A) and BaL (FIG. 19B) isolates.
Figure 19B:
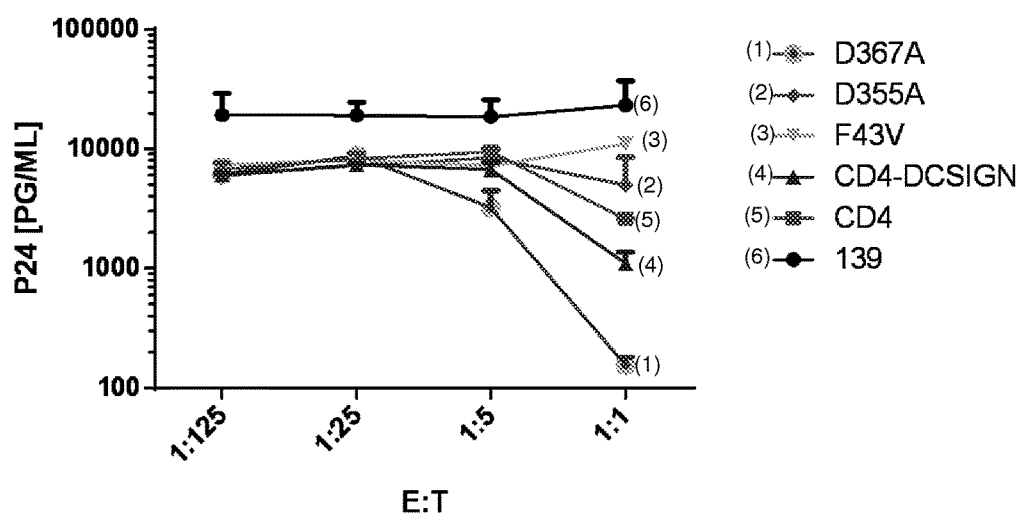

To test the role of each moiety in the function of the CD4-DCSIGN CAR, constructs containing mutations in each moiety were compared. In CD4, the F43V mutation is known to block binding to gp120. The data show that this mutation abrogated the function of the CD4-DCSIGN CAR for both the BX08 (FIG. 19A) and the BaL (FIG. 19B) isolates. In DC-SIGN, the D355A mutation blocks binding to high mannose glycans, whereas the D367A enhances binding. In the CAR constructs, these mutations inhibited and enhanced CAR function, respectively, for both the BX08 (FIG. 19A) and BaL (FIG. 19B) isolates. These results confirm the important role of the CD4 moiety in the function of the CD4-DCSIGN CAR, and demonstrate the enhancing role of the glycan-binding activity of the DCSIGN CRD component.

Example 8

Activity of CARs Comprising a CRD from Other Lectins

Figure 20A:
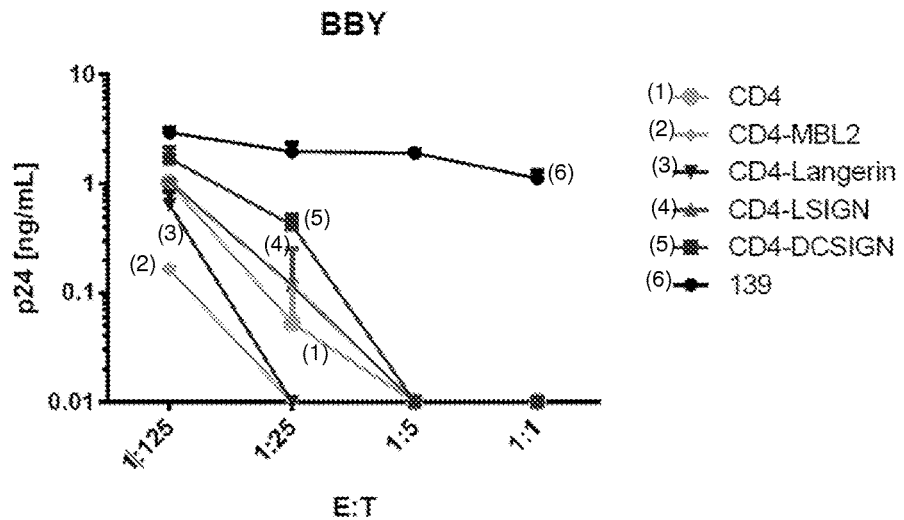
FIGS. 20A-20C are a series of graphs showing that different CD4-Lectin CARs (CD4-LSIGN CAR, CD4-Langerin CAR, and CD4-MBL2 CAR) are effective against several HIV-1 primary isolates. This illustrates that linking CD4 to CRDs from diverse C-type lectins as components of a CAR ectodomain result in potent anti-HIV activity.
Figure 20B:
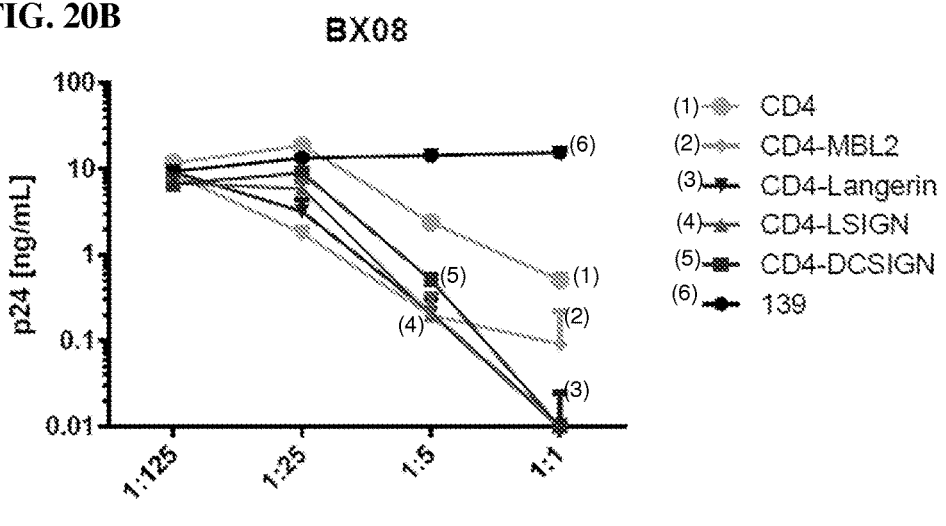
Figure 20C:
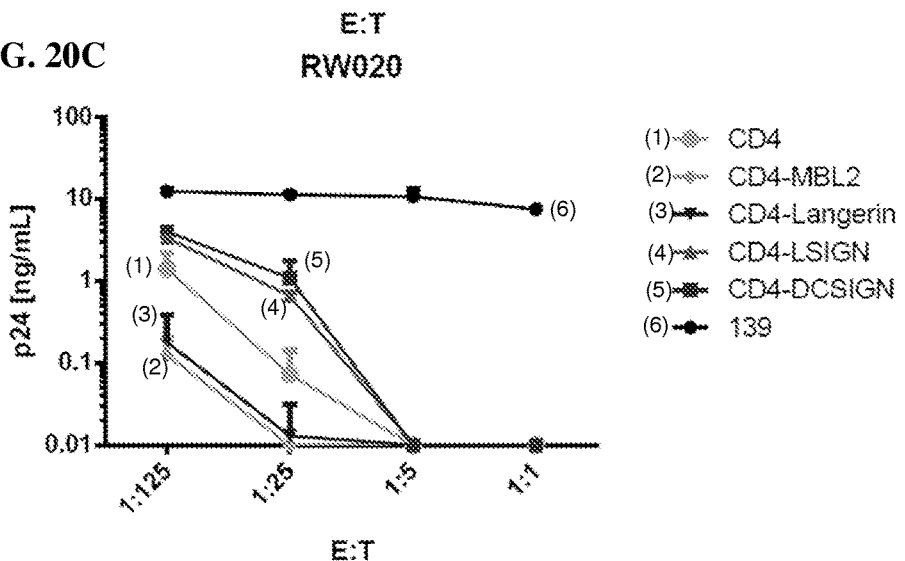

FIG. 20A-20C show that different CD4-Lectin CARs are effective against several HIV-1 primary isolates using the Spreading Infection assays as described in Example 7. The illustrated constructs are: CD4-LSIGN CAR (ectodomain SEQ ID NO: 49), CD4-Langerin CAR (ectodomain SEQ ID NO: 51), and CD4-MBL2 CAR (ectodomain SEQ ID NO: 53). This illustrates that linking CD4 to CRDs from diverse C-type lectins as components of a CAR ectodomain result in potent anti-HIV activity.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A multispecific chimeric antigen receptor protein, comprising:
   an N-terminal extracellular targeting segment comprising:
   a first targeting domain comprising a CD4 domain that binds to HIV Env, wherein the CD4 domain comprises the D1 and D2 extracellular domains of CD4 comprising amino acids 1-208 of SEQ ID NO: 53; and
   a second targeting domain comprising a carbohydrate recognition domain (CRD) from a human C-type lectin that binds to HIV Env, wherein the CRD is selected from the group consisting of a CRD from mannose-binding lectin 2 (MBL2) comprising amino acids 214-330 of SEQ ID NO: 53 and a CRD from Langerin comprising amino acids 214-354 of SEQ ID NO: 51;
   wherein the first and second targeting domains bind to different sites on HIV Env, and wherein the multispecific chimeric antigen receptor protein binds to HIV Env.

2. The multispecific chimeric antigen receptor protein of claim 1, comprising a linker connecting the first targeting domain to the second targeting domain.

3. The multispecific chimeric antigen receptor protein of claim 1, comprising an amino acid sequence selected from the group consisting of the amino acid sequence of SEQ ID NO: 51, and the amino acid sequence of SEQ ID NO: 53.

4. The multispecific chimeric antigen receptor protein of claim 1, further comprising:
   a linker connecting the extracellular targeting segment to a transmembrane domain;
   the transmembrane domain; and
   an intracellular region, comprising:
      a cytoplasmic co-stimulatory signaling domain; and
      a cytoplasmic effector function signaling domain,
   wherein the transmembrane domain is linked or fused to the intracellular region.

5. The multispecific chimeric antigen receptor protein of claim 4, wherein:
   the transmembrane domain is from CD28;
   the cytoplasmic co-stimulatory signaling domain is from CD28; and/or
   the cytoplasmic effector function signaling domain is from CD3 zeta.

6. The multispecific chimeric antigen receptor protein of claim 2, wherein the linker connecting the first targeting domain to the second targeting domain is no more than 20 amino acids long.

7. The multispecific chimeric antigen receptor protein of claim 6, wherein the linker connecting the first targeting domain to the second targeting domain is ten amino acids long.

8. The multispecific chimeric antigen receptor protein of claim 1, comprising:
   the N-terminal extracellular targeting segment comprising:
      the first targeting domain; and
      the second targeting domain, wherein the second targeting domain is a MBL2 domain;
   a transmembrane region from CD28; and
   an intracellular region, comprising:
      a cytoplasmic co-stimulatory signaling domain from CD28; and
      a cytoplasmic effector function signaling domain from CD3 zeta,
   wherein the N-terminal extracellular targeting segment is linked to the transmembrane region and the transmembrane region is linked or fused to the intracellular region.

9. The multispecific chimeric antigen receptor protein of claim 8, wherein:
   the N-terminal extracellular targeting segment comprises the amino acid sequence of SEQ ID NO: 53;
   the transmembrane region from CD28 comprises the amino acid sequence of SEQ ID NO: 55;
   the cytoplasmic co-stimulatory signaling domain from CD28 comprises the amino acid sequence of SEQ ID NO: 58; and
   the cytoplasmic effector function signaling domain from CD3 zeta comprises the amino acid sequence of SEQ ID NO: 56.

10. A T cell comprising the multispecific chimeric antigen receptor protein of claim 1.

11. The T cell of claim 10, wherein the T cell is a CD8$^+$ T cell and/or a CD4$^+$ T cell.

12. The T cell of claim 10, wherein the T cell is not susceptible to HIV infection.

13. A composition, comprising the T cell of claim 10 and a carrier.

14. A method of killing HIV-infected cells, comprising:
   contacting the composition of claim 13 with an HIV-infected cell expressing gp120, thereby killing the HIV-infected cells.

15. A method of reducing the level of HIV infected cells in a subject infected with HIV, comprising:
   administering to the subject a therapeutically effective amount of the composition of claim 13, thereby treating the subject infected with HIV.

16. The method of claim 15, wherein the T cell in the composition is a T cell that is not susceptible to HIV infection.

17. A method of treating a subject with an HIV infection, comprising: administering to the subject a therapeutically effective amount of the composition of claim 13 under conditions sufficient to form an immune complex of the extracellular targeting segment on the chimeric antigen receptor protein and the extracellular domain of an HIV Env protein in the subject.

* * * * *